US011307198B2

(12) United States Patent
Lin et al.

(10) Patent No.: US 11,307,198 B2
(45) Date of Patent: Apr. 19, 2022

(54) COMPOSITIONS AND METHODS FOR ANTIGEN DETECTION INCORPORATING INORGANIC NANOSTRUCTURES TO AMPLIFY DETECTION SIGNALS

(71) Applicant: Washington State University, Pullman, WA (US)

(72) Inventors: Yuehe Lin, Pullman, WA (US); Dan Du, Pullman, WA (US); Yang Song, Pullman, WA (US); Ranfeng Ye, Pullman, WA (US)

(73) Assignee: Washington State University, Pullman, WA (US)

( * ) Notice: Subject to any disclaimer, the term of this patent is extended or adjusted under 35 U.S.C. 154(b) by 178 days.

(21) Appl. No.: 15/495,852

(22) Filed: Apr. 24, 2017

(65) Prior Publication Data

US 2017/0336398 A1   Nov. 23, 2017

Related U.S. Application Data

(60) Provisional application No. 62/327,851, filed on Apr. 26, 2016.

(51) Int. Cl.
| | |
|---|---|
| *G01N 33/543* | (2006.01) |
| *G01N 33/553* | (2006.01) |
| *G01N 33/58* | (2006.01) |
| *C12Q 1/00* | (2006.01) |
| *G01N 33/00* | (2006.01) |

(52) U.S. Cl.
CPC ..... *G01N 33/54346* (2013.01); *G01N 33/553* (2013.01); *G01N 33/581* (2013.01); *G01N 33/587* (2013.01); *C12Q 1/00* (2013.01); *G01N 33/00* (2013.01)

(58) Field of Classification Search
CPC ..... G01N 33/54346; G01N 33/00; C12Q 1/00
See application file for complete search history.

(56) References Cited

U.S. PATENT DOCUMENTS

2014/0271470 A1*  9/2014  Sillerud ............... A61K 31/337
424/1.73

OTHER PUBLICATIONS

Gao et al. ("Intrinsic peroxidase-like acitivty of ferromagnetic nanoparticle", Nature Nanotechnology vol. 2, pp. 577-583, published Sep. 2, 2007) (Year: 2007).*

(Continued)

*Primary Examiner* — Tracy Vivlemore
*Assistant Examiner* — Nam P Nguyen
(74) *Attorney, Agent, or Firm* — Christensen O'Connor Johnson Kindness PLLC

(57) ABSTRACT

The disclosure relates to antigen detection reagents and related methods, systems, and kits. The reagents comprise an antigen-binding molecule conjugated to an inorganic component. In some embodiments, the inorganic component possesses catalytic functionality to provide a detectable signal. In some embodiments, the catalytic inorganic component is or comprises a bimetallic nanoparticle. In other embodiments, the inorganic component is a nanoflowers that provides a physical scaffold onto which the antigen-binding component and a reporter component can be loaded, resulting in augmented antigen-binding and reporting capabilities.

2 Claims, 47 Drawing Sheets

(56) References Cited

OTHER PUBLICATIONS

Zhou et al., "Ultrasensitive immunoassay based on a pseudobienzyme amplifying system of choline oxidase and luminol-reduced Pt @Au hybrid nanoflowers", Chem. Commun. vol. 50, p. 14627-14630, published Aug. 5, 2014) (Year: 2014).*

Zhang et al. ("Manganese(II) phosphate nanoflowers as electrochemical biosensors for the high-sensitivity detection of ractopaime", Sensors and Actuators B, vol. 211, pp. 310-317, published Feb. 3, 2015). (Year: 2015).*

Liu et al. ("Au—Pt nanoparticle-based electrochemiluminescence immunoassay of a cancer biomarker using ZnO nanospheres coated with CdTe quantum dots as labels", Monatsh. Chem. (2014), vol. 145, pp. 121-127) (Year: 2014).*

Zeng et al. ("Preparation of Carbon-Supported Core-Shell Au—Pt Nanoparticles for Methanol Oxidation Reaction: The Promotional Effect of the Au Core", J. Phys. Chem. B 2006, vol. 110, pp. 24606-24611). (Year: 2006).*

Nangia et al. ("Palladium@gold bimetallic nanostructures as peroxidase mimic for development of sensitive fluoroimmunoassay", Analytica Chimica Acta, vol. 751, pp. 140-145, published Sep. 14, 2012) (Year: 2012).*

Hamed et al. ("All-Metal Mesoporous Nanocolloids: Solution-Phase Synthesis of Core-Shell Pd@Pt Nanoparticles with a designed Concave Surface", Angew. Chem. Int. Ed., vol. 52, pp. 13611-13615, published Nov. 15, 2013) (Year: 2013).*

Ataee-Esfahani, H., et al., "All-Metal Mesoporous Nanocolloids: Solution-Phase Synthesis of Core-Shell Pd@Pt Nanoparticles With a Designed Concave Surface," Angewandte Chemie 125(51):13856-13860, Dec. 2013.

Cui, X., et al., "Establishing of a Method Combined Immunomagnetic Separation With Colloidal Gold Lateral Flow Assay and Its Application in Rapid Detection of *Escherichia coli* O157:H7," Chinese Journal of Analytical Chemistry 41(12):1812-1816, Dec. 2013.

Ge, J., et al., "Protein-Inorganic Hybrid Nanoflowers," Nature Nanotechnology 7(7):428-432, Jul. 2012.

Hammock, M.L., et al., "Electronic Readout Enzyme-Linked Immunosorbent Assay With Organic Field-Effect Transistors as a Preeclampsia Prognostic," Advanced Materials 26(35):6138-6144, Sep. 2014.

He, W., et al., "Au@Pt Nanostructures as Oxidase and Peroxidase Mimetics for Use in Immunoassays," Biomaterials 32(4):1139-1147, Feb. 2011.

Hossain, M.F., and J.Y. Park, "Amperometric Glucose Biosensor Based on Pt—Pd Nanoparticles Supported by Reduced Graphene Oxide and Integrated With Glucose Oxidase," Electroanalysis 26(5):940-951, May 2014.

Hu, C., et al., "Enzyme-Labeled Pt@BSA Nanocomposite as a Facile Electrochemical Biosensing Interface for Sensitive Glucose Determination," Applied Materials & Interfaces 6(6):4170-4178, Mar. 2014.

Huang, Y., and D.-H. Kim, "Synthesis and Self-Assembly of Highly Monodispersed Quasispherical Gold Nanoparticles," Langmuir 27(22):13861-13867, Nov. 2011.

Huang, Y., et al., "Self-Assembly of an Organic-Inorganic Hybrid Nanoflower as an Efficient Biomimetic Catalyst for Self-Activated Tandem Reactions," Chemical Communications 51(21):4386-4389, Mar. 2015.

Jing, W., et al., "Development of a Gold-Immunochromatography Test for Rapid Detecting *E. coli* O157," Journal of Hygiene Research 35(4):439-441, Jul. 2006.

Li, X., et al., "Spatial Co-Localization of Multi-Enzymes by Inorganic Nanocrystal-Protein Complexes," Chemical Communications 50(83):12465-12468, Oct. 2014.

Lin, Z., et al., "Facile Synthesis of Enzyme-Inorganic Hybrid Nanoflowers and Its Application as a Colorimetric Platform for Visual Detection of Hydrogen Peroxide and Phenol," Applied Materials & Interfaces 6(13):10775-10782, Jul. 2014.

Lin, Z., et al., "Facile Synthesis of Enzyme-Inorganic Hybrid Nanoflowers and Their Application as an Immobilized Trypsin Reactor for Highly Efficient Protein Digestion," RSC Advances 4:13888-13891, 2014.

Shukla, S., et al., "Immunochromatographic Strip Assay for the Rapid and Sensitive Detection of *Salmonella typhimurium* in Artificially Contaminated Tomato Samples," Canadian Journal of Microbiology 60(6):399-406, Jun. 2014.

Song, C., et al., "Development of a Lateral Flow Colloidal Gold Immunoassay Strip for the Simultaneous Detection of Shigella boydii and *Escherichia coli* O157:H7 in Bread, Milk and Jelly Samples," Food Control 59:345-351, Jan. 2016.

Vousden, K.H., and X. Lu, "Live or Let Die: The Cell's Response to p53," Nature Reviews: Cancer 2(8):594-604, Aug. 2002.

Wang, H., et al., "All-Metal Layer-by-Layer Films: Bimetallic Alternate Layers With Accessible Mesopores forCed Electrocatalysis," Journal of the American Chemical Society 134(26):10819-10821, Jul. 2012.

Wang, L.-J., et al., "High-Throughput Optical Sensing Immunoassays on Smartphone," Analytical Chemistry 88(16):8302-8308, Aug. 2016.

Wu, H., et al., "Facile Synthesis of Pt/Pd Nanodendrites for the Direct Oxidation of Methanol," Nanotechnology 25(19):195702, May 2014, 8 pages.

Xiao, F., et al., "Nonenzymatic Glucose Sensor Based on Ultrasonic-Electrodeposition of Bimetallic PtM (M=Ru, Pd and Au) Nanoparticles on Carbon Nanotubes-Ionic Liquid Composite Film," Biosensors and Bioelectronics 24(12):3481-3486, Aug. 2009.

Xu, C., et al., "Nanotubular Mesoporous Bimetallic Nanostructures With Enhanced Electrocatalytic Performance," Advanced Materials 21(21):2165-2169, Jun. 2009.

Yin, Y., et al., "An Enzyme-Inorganic Hybrid Nanoflower Based Immobilized Enzyme Reactor With Enhanced Enzymatic Activity," Journal of Materials Chemistry B 3(11):2295-2300, 2015.

Yuan, C.-Y., et al., "A New Electrochemical Sensor of Nitro Aromatic Compound Based on Three-Dimensional Porous Pt—Pd Nanoparticles Supported by Graphene-Multiwalled Carbon Nanotube Composite," Biosensors and Bioelectronics 58:85-91, 2014.

Zeng, J., and Y. Xia, "Hybrid Nanomaterials: Not Just a Pretty Flower," Nature Nanotechnology 7(7):415-416, Jul. 2012.

Zhang, H., et al., "Detection of Single-Digit Foodborne Pathogens With the Naked Eye Using Carbon Nanotube-Based Multiple Cycle Signal Amplification," Chemical Communications 50(15):1848-1850, Feb. 2014.

Zhang, Y., et al., "Enhanced Activity of Immobilized or Chemically Modified Enzymes," ACS Catalysis 5(8):4503-4513, Aug. 2015.

Zhu, C., et al., "Kinetically Controlled Synthesis of PdNi Bimetallic Porous Nanostructures With Enhanced Electrocatalytic Activity," Small 11(12):1430-1434, Mar. 2015.

Cheng, N., et al., "Smartphone-Based Dual-Lateral Flow Immunoassays for Simultaneous Detection of *Salmonella* and *Escherichia coli* O157:H7 Using Pt—Pd Nanoparticles as Signal Amplification," draft manuscript, n.d., 30 pages.

Guo, S., and E. Wang, "Noble Metal Nanomaterials: Controllable Synthesis and Application in Fuel Cells and Analytical Sensors," Nanotoday 6(3):240-264, Jun. 2011.

Jiang, T., et al., "Detection of p53 Protein Based on Mesoporous Pt—Pd Nanoparticles With Enhanced Peroxidase-Like Catalysis," ACS Sensors 1(6):717-724, Jun. 2016.

Jiang, T., et al., "Sensitive Detection of *Escherichia coli* O157:H7 Using Pt—Au Bimetal Nanoparticles With Peroxidase-Like Amplification," Biosensors and Bioelectronics 77:687-694, Mar. 2016; plus supplementary data.

Jung, B.Y., et al., "Development of a Rapid Immunochromatographic Strip for Detection of *Escherichia coli* O157," Journal of Food Protection 68(10):2140-2143, Oct. 2005.

Lehoux, A., et al., "Tuning the Porosity of Bimetallic Nanostructures by a Soft Templating Approach," Advanced Functional Materials 22(23):4900-4908, Dec. 2012.

Ma, M., et al., "Peroxidase-Like Catalytic Activity of Cubic Pt Nanocrystals," Colloids and Surfaces A: Physicochemical and Engineering Aspects 373(1-3):6-10, Jan. 2011.

(56) References Cited

OTHER PUBLICATIONS

Maiyalagan, T., et al., "Electrodeposited Pt on Three-Dimensional Interconnected Graphene as a Free-Standing Electrode for Fuel Cell Application," Journal of Materials Chemistry 22(12):5286-5290, Mar. 2012.

Moongkarndi, P., et al., "Evaluation of an Immunochromatographic Assay for Rapid Detection of Salmonella enterica serovars Typhimurium and Enteritidis," Journal of Veterinary Diagnostic Investigation 23(4):797-801, Jul. 2011.

Nasrabadi, H.T., et al., "Bimetallic Nanoparticles: Preparation, Properties, and Biomedical Applications," Artificial Cells, Nanomedicine, and Biotechnology 44(1):376-380,2016.

Shi, Q., et al., "Mesoporous Pt Nanotubes as a Novel Sensing Platform for Sensitive Detection of Intracellular Hydrogen Peroxide," ACS Applied Materials & Interfaces 7(43):24288-24295, Nov. 2015.

Sun, J., et al., "Multi-Enzyme Co-Embedded Organic-Inorganic Hybrid Nanoflowers: Synthesis and Application as a Colorimetric Sensor," Nanoscale 6(1):255-262, Jan. 2014.

Upadhyay, S., et al., "Immobilization of Acetylcholineesterase-Choline Oxidase on a Gold-Platinum Bimetallic Nanoparticles Modified Glassy Carbon Electrode for the Sensitive Detection of Organophosphate Pesticides, Carbamates and Nerve Agents," Biosensors and Bioelectronics 25(4):832-838, Dec. 2009.

Wang, L.B., et al., "A New Nanobiocatalytic System Based on Allosteric Effect With Dramatically Enhanced Enzymatic Performance," Journal of the American Chemical Society 135(4):1272-1275, Jan. 2013.

Wei, T., et al., "An Improved Ultrasensitive Enzyme-Linked Immunosorbent Assay Using Hydrangea-Like Antibody-Enzyme-Inorganic Three-in-One Nanocomposites," ACS Applied Materials & Interfaces 8(10):6329-6335, Mar. 2016; plus supporting information, 2 pages.

Ye, R., et al., "Bioinspired Synthesis of All-in-One Organic-Inorganic Hybrid Nanoflowers Combined With a Handheld pH Meter for On-Site Detection of Food Pathogen," Small 12(23):3094-3100, Jun. 2016; plus supporting information, 8 pages.

Ye, R., et al., "One Pot Bioinspired Synthesis of All-Inclusive Protein-Protein Nanoflowers for Point-of-Care Bioassay: Detection of E. coli O157:H7 From Milk," Nanoscale 8(45): 18980-18986, Dec. 2016.

Zeinhom, M.M.A., et al., "Smart Phone Based Immunosensor Coupled With Nanoflower Signal Amplification for Rapid Detection of Salmonella enteritidis in Dairy Foods and Water," draft manuscript, n.d., 24 pages.

Zhang, W., et al., "Nanomaterial-Based Biosensors for Environmental and Biological Monitoring of Organophosphorus Pesticides and Nerve Agents," TrAC Trends in Analytical Chemistry 54:1-10, Feb. 2014.

Zhu, C., et al., "Electrochemical Sensors and Biosensors Based on Nanomaterials and Nanostructures," Analytical Chemistry 87(1):230-249, Jan. 2015.

\* cited by examiner

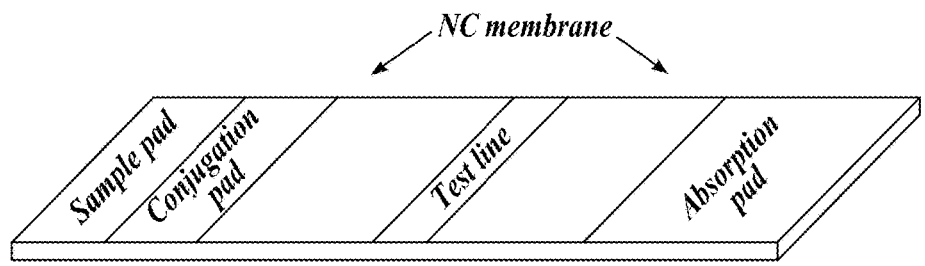
FIG. 1A
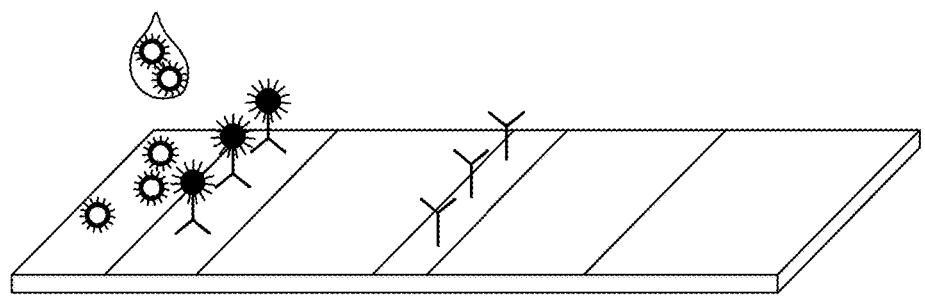
FIG. 1B
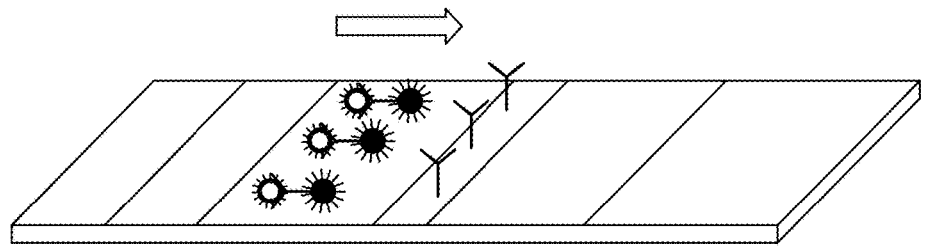
FIG. 1C
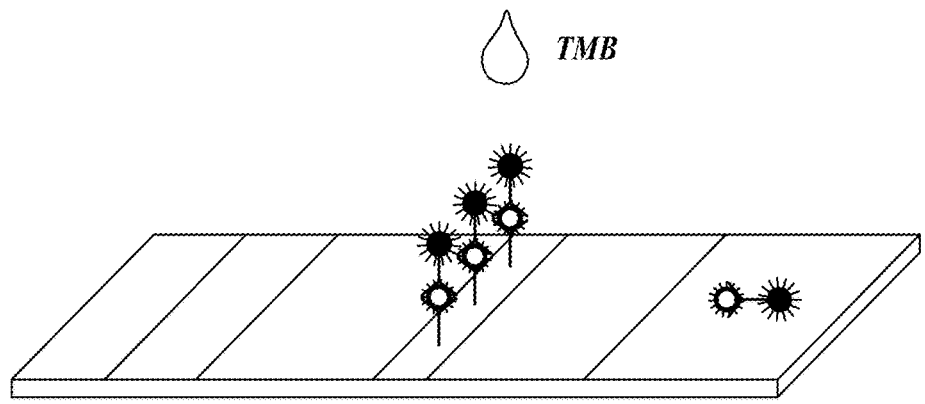
FIG. 1D
 *E. coli*    *Pt-Au Ab1*    *Ab2*

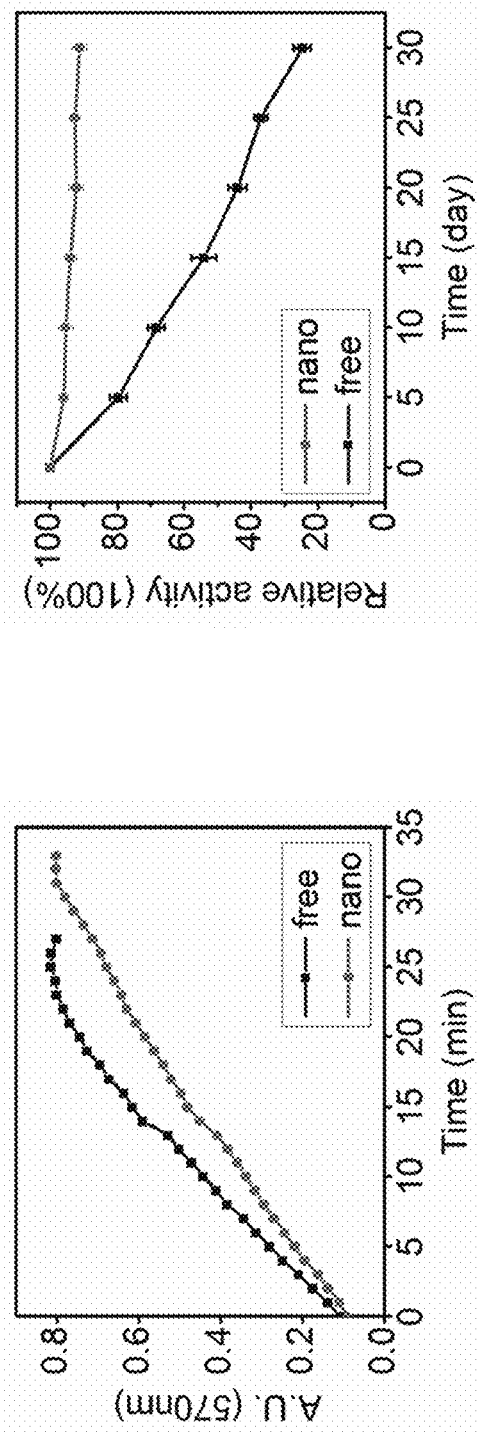
FIG. 37A
FIG. 37B
FIG. 37C
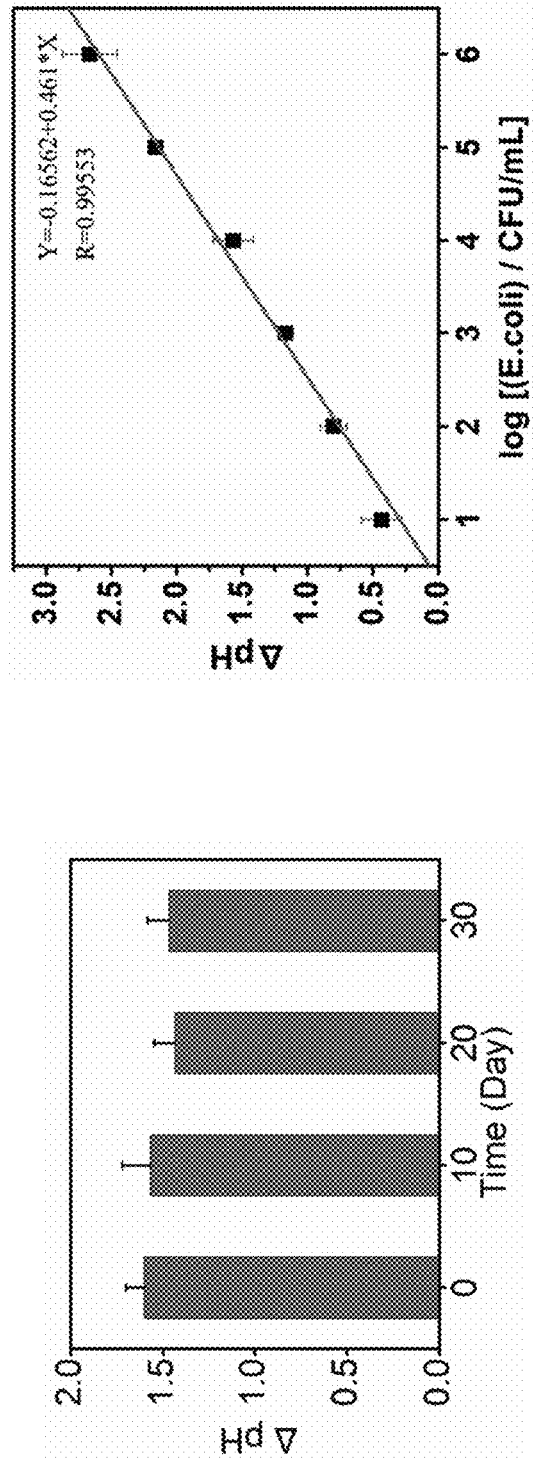
FIG. 38

COMPOSITIONS AND METHODS FOR ANTIGEN DETECTION INCORPORATING INORGANIC NANOSTRUCTURES TO AMPLIFY DETECTION SIGNALS

CROSS-REFERENCE TO RELATED APPLICATION

This application claims the benefit of U.S. Provisional Application No. 62/327,851, filed on Apr. 26, 2016, the entire disclosure of which is incorporated by reference herein.

STATEMENT OF GOVERNMENT LICENSE RIGHTS

This invention was made with Government support under R21 OH010768 awarded by the Centers for Disease Control and Prevention, National Institute for Occupational Safety and Health (CDC/NIOSH). The Government has certain rights in the invention.

BACKGROUND

The accurate and consistent detection of antigens of interest from complex samples such as biological and food samples remains a challenge, especially when attendant costs are contemplated. In fields such as disease monitoring and food quality inspection, efforts have been made to develop sensitive techniques to detect minute quantities of antigens, such as pathogen antigens, from complex samples. Such efforts have included development of technologies to amplify detection signals. However, despite the advances in the art, many pathogen detection strategies require reagents that are difficult or expensive to produce, or otherwise require equipment that is not amenable to point of care or field monitoring. Thus, a need remains for antigen detection reagents that can accurately, inexpensively, and rapidly provide detectable signals for miniscule levels of antigens of interest, e.g., low level infections or contaminations, from complex samples. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides an antigen detection reagent, comprising an antigen-binding molecule conjugated to an inorganic component.

In one embodiment, the inorganic component comprises a bimetallic nanoparticle. In some embodiments, the bimetallic nanoparticle is a platinum (Pt)-gold (Au) bimetallic nanoparticle (Pt/Au NP), a platinum (Pt)-palladium (Pd) bimetallic nanoparticle (Pt/Pd NP), a platinum (Pt)-cobalt (Co) bimetallic nanoparticle (Pt/Co NP), a platinum (Pt)-nickel (Ni) bimetallic nanoparticle (Pt/Ni NP), or a platinum (Pt)-iron (Fe) bimetallic nanoparticle (Pt/Fe NP). In one embodiment, the bimetallic nanoparticle has catalytic activity. In one embodiment, the bimetallic nanoparticle has peroxidase activity.

In one embodiment, the inorganic component is an inorganic nanoflower component. In one embodiment, the inorganic nanoflower component comprises $Cu_3(PO_4)_2$, $Mn_3(PO_4)_2$, or $CaHPO_4$. In one embodiment, the detection reagent further comprises a reporter component conjugated to the inorganic component. In one embodiment, the reporter agent is a reporter enzyme or a bimetallic nanoparticle with catalytic activity. In one embodiment, the reporter enzyme is horseradish peroxidase (HRP), invertase, glucose oxidase (GOx) or alkaline phosphatase (AP).

In one embodiment, the antigen-binding molecule is an antibody, antibody-like molecule, lectin, receptor, aptamer, or a functional antigen-binding domain thereof. In one embodiment, the antibody-like molecule is a single-chain antibody, a bispecific antibody, a Fab fragment, or a $F(ab)_2$ fragment. In one embodiment, the single-chain antibody is a single chain variable fragment (scFv), single-chain Fab fragment (scFab), $V_HH$ fragment, $V_{NAR}$, or nanobody. In one embodiment, the lectin is concanavalin A.

In one embodiment, the Pt/Au NP is covalently conjugated to the antigen binding molecule. In one embodiment, the Pt/Au NP is non-covalently conjugated to the antigen binding molecule. In one embodiment, the antigen-binding molecule is covalently conjugated to one or both of the reporter enzyme and inorganic component. In one embodiment, the antigen-binding molecule is non-covalently conjugated to one or both of the reporter enzyme and inorganic component.

In another aspect, the disclosure provides a method of detecting an antigen of interest. The method comprises contacting a sample with the antigen detection reagent disclosed herein under conditions sufficient to permit the selective binding of the antigen detection reagent to the antigen of interest, and detecting the presence of the antigen of interest. In one embodiment, detecting the presence of the antigen of interest comprises contacting the bound antigen detection reagent with a substrate, thereby producing a product, and detecting the presence of the product, thereby indicating the presence of the antigen of interest. In one embodiment, detecting the presence of the antigen of interest further comprises quantifying the antigen of interest in the sample. In one embodiment, the conversion of the substrate to the product provides a detectable signal. In one embodiment, the detection reagent has peroxidase activity, wherein the substrate is a peroxidase substrate, and wherein the product is a peroxidase product. In one embodiment, the peroxidase substrate is 3,3',5,5'-tetramethylbenzidine (TMB). In one embodiment, the detection reagent has invertase activity, wherein the substrate is sucrose, and wherein the product is glucose. In one embodiment, the detection reagent has glucose oxidase activity, wherein the substrate is glucose, and wherein the product is gluconic acid. In one embodiment, the method further comprises contacting the sample with a primary detection reagent that specifically binds to a target antigen, wherein the primary detection reagent comprises the "antigen of interest" that can be specifically bound by the antigen-binding molecule of the antigen detection reagent. The detection of the antigen of interest indicates the presence of the target antigen, as in a "sandwich ELISA".

In another aspect, the disclosure provides a system, device, and/or kit for detecting and/or quantifying an antigen of interest and/or target antigen in a sample, comprising the antigen detection reagent as described herein. In one embodiment, the system, device, and/or kit further comprises a capture reagent that specifically binds to the antigen of interest in a manner that is non-competitive with antigen-binding molecule. In one embodiment, the system, device, and/or kit further comprises a primary detection reagent that specifically binds to a target antigen, wherein the antigen-binding molecule of the antigen detection reagent specifically binds to the primary detection reagent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1D provide a schematic illustration of ICA platform detection of $E.\ coli$ O157:H7. FIG. 1A shows the typical assembly of ICA. The ICA system consists of sample pad, conjugated pad, adsorption pad and nitrocellulose membrane. All components are bound together layer-by-layer. FIG. 1B shows the anti-$E.\ coli$ O157:H7 Ab1 was covalent bounded with Pt—Au NPs and then modified onto the conjugated pad. $E.\ coli$ O157:H7 is applied to the sample pad. FIG. 1C shows the $E.\ coli$ O157:H7 combines with Pt—Au-anti-$E.\ coli$ O157:H7 Ab1 conjugates and migrates along the porous membrane by capillary action. FIG. 1D shows that the formed complexes continue to migrate along the membrane and are captured by the monoclonal antibodies (Ab2) to form Pt—Au-Ab1-$E.\ coli$-Ab2 complexes on the test line. As the liquid sample continues migrating, the excess complexes are migrated toward the absorption pad. Signal was amplified by adding TMB at test line.

FIG. 2A: TEM; FIG. 2B: zoom in image of FIG. 2A; FIG. 2C: SEM; FIG. 2D: zoom in image for FIG. 2C.

FIG. 3A shows photographs of the color evolution of TMB oxidation in the presence of $H_2O_2$ in a pH 4.4 PBS buffer. FIG. 3B shows the corresponding reaction mechanisms for $H_2O_2$ reduction with TMB. FIG. 3C shows the effects of $H_2O_2$ concentration on the reaction rate of TMB oxidation catalyzed by Pt—Au NPs. The straight line is a linear regression between 0 and 50 mM $H_2O_2$. The inset is the absorbance evolution at 650 nm over time at various $H_2O_2$ concentrations.

FIG. 6A shows dual-lateral flow immunoassays; FIG. 6B shows Pt—Pd nanoparticles for signal amplification; and FIG. 6C shows an illustrative smartphone-based device and system.

FIG. 7A is a schematic illustration of Pt—Pd nanoparticles formation. FIG. 7B is a TEM image of Pt—Pd nanoparticles, with a mean diameter of 35 nm. FIG. 7C is a TEM image of antibody-modified Pt—Pd nanoparticle conjugation. FIG. 7D is a TEM image of $E.\ coli$ O157:H7 captured by antibody modified Pt—Pt nanoparticle conjugations. FIG. 7E is a TEM image of $Salmonella$ captured by antibody modified Pt—Pt nanoparticle conjugations. FIG. 7F and FIG. 7G are TEM images of details for the recognition function of antibodies modified Pt—Pt nanoparticle conjugations.

FIG. 8A graphically shows the effect of different amount of antibody modified Pt—Pd nanoparticle conjugations: 0.5, 1, 1.5, 2, 2.5 and 3 µL; concentration of target bacteria: $10^8$ CFU/mL. FIG. 8B graphically shows the effect of reaction time after adding TMB solution: from 1 to 16 min; concentration of target bacteria: $10^8$ CFU/mL. FIG. 8C graphically shows the effect of amount of BSA in running buffer: 0, 1%, 2%, 3%, 4%, and 5%; concentration of target bacteria: $10^7$ CFU/mL. FIG. 8D graphically shows the effect of amount of Tween-20 in running buffer: 0, 0.0675%, 0.125%, 0.25%, 0.5%, and 1%; concentration of bacteria: $10^7$ CFU/mL. Error bars indicate standard deviations of three measurements.

FIGS. 9A and 9B illustrate dual-LFIAs without TMB solution. FIGS. 9C and 9D illustrate dual-LFIAs with TMB solution. Photo image of dual-LFIAs with different bacterial concentrations ranging from 0 to $10^8$ CFU/mL were taken and quantitative detections were performed by recording the peak areas of two test lines. FIGS. 9A-9D show the calibration curves of peak areas of test lines versus target concentrations. Error bars indicate standard deviations of three measurements.

FIGS. 11A and 11B are TEM and FIGS. 11C and 11D are SEM images of mesoporous Pt—Pd porous NPs. FIGS. 11B and 11D are magnified images of FIGS. 11A and 11C, respectively.

FIG. 12A shows UV absorption spectra of different reaction substrates in pH 4.5 HAc—NaAc buffer. FIG. 12B shows stability of Pt—Pd NPs. Pt—Pd NPs were first incubated at pH 1-11 for 5 h, and then the peroxidase-like activity was measured. Pt—Pd NPs were first incubated at 4-90° C. for 5 h, and then the peroxidase-like activity was measured. All the conditions: 20 mM TMB, 5 mM $H_2O_2$, 0.2 mM HAc—NaAc buffer (pH 4.5), and 0.5 µg $mL^{-1}$ catalysts.

FIG. 14A shows the concentration of $H_2O_2$ was 5 mM and the TMB concentration was varied for Pt—Pd NPs and Pt nanopowders. FIG. 14B shows the concentration of TMB was 20 mM and the $H_2O_2$ concentration was varied for Pt—Pd NPs and Pt nanopowders. FIGS. 14C and 14D show the double reciprocal plots of activity of Pt—Pd NPs composite with the concentration of one substrate fixed and the other varied.

FIG. 17A graphically illustrates the effect of conjugated amount of NPs on S/N ratio of ITS. Loading concentration of Ab1 in the conjugate: 6.5 μg mL$^{-1}$; running buffer: PBS (1% BSA). FIG. 17B graphically illustrates the effect of Ab1 concentration in the conjugate on S/N ratio of ITS. Loading concentration of Pt—Pd NPs: 20 μg mL$^{-1}$. FIG. 17C graphically illustrates the effect of pH of components on S/N ratio of ITS. Loading concentration of Ab1 in the conjugate: 6.5 μg mL$^{-1}$; Loading concentration of Pt—Pd NPs: 20 μg mL$^{-1}$. FIG. 17D graphically illustrates the effect of TMB dilution rate on S/N ratio of ITS. Loading concentration of Ab1 in the conjugate: 6.5 μg/mL; Loading concentration of Pt—Pd NPs: 20 μg mL$^{-1}$; running buffer: PBS (1% BSA). FIG. 17E graphically illustrates the effect of reaction time on S/N ratio of ITS. Loading concentration of Ab1 in the conjugate: 6.5 μg mL$^{-1}$; Loading concentration of Pt—Pd NPs: 20 μg mL$^{-1}$.

FIG. 22A graphically illustrates the enzymatic activity of nanoflowers and free HRP in PBS (pH 7.4) during storage at room temperature. FIG. 22B shows SEM images of the nanoflowers stored in PBS for two months.

FIG. 23A shows the concentration of capture antibody (Ab1); FIG. 23B shows the concentration of BSA; FIG. 23C shows the concentration of the HRP-Ab2-$Cu_3(PO_4)_2$ nanoflowers; and FIG. 23D shows the incubation time of the HRP-Ab2-$Cu_3(PO_4)_2$ nanoflowers. The solid and dashed lines mean the optical densities obtained from the assays without or with $1.7\times10^6$ CFU mL$^{-1}$ *E. coli* O157:H7, respectively.

FIG. 25A graphically illustrates the optical density of the anti-*E. coli* O157:H7 antibody-HRP—$Cu_3(PO_4)_2$ nanoflower-based ELISA after incubation with different bacteria ($1.7\times10^5$ CFU mL$^{-1}$). FIG. 25B represents two samples with different concentrations of *E. coli* O157:H7 that were assayed using the same lot of the HRP-Ab2-$Cu_3(PO_4)_2$ nanocomposites over a 40-day period.

FIG. 28A shows bright-field image of CIC hybrid nanoflowers. FIG. 28B shows CIC hybrid nanoflowers with FITC-labeled Con A. FIG. 28C shows CIC hybrid nanoflowers with Cy5-labeled invertase. FIG. 28D shows the overlap image of FIGS. 28B and 28C.

FIG. 35A shows SEM and FIGS. 35B and 35C show TEM images of Con A-GOx-CaHPO$_4$ hybrid nanoflowers. FIG. 35D shows XRD pattern of Con A-GOx-CaHPO$_4$ hybrid nanoflowers.

FIG. 36A shows bright-field image of Con A-GOx-CaHPO$_4$ hybrid nanoflowers. FIG. 36B shows Cy5 labelled GOx in hybrid nanoflowers. FIG. 36C shows FITC labelled Con A in hybrid nanoflowers. FIG. 36D shows the overlap image of bright-field and fluorescence images.

FIGS. 37A-37C: FIG. 37A graphically illustrates the kinetics of activity of free GOx and Con A-GOx-CaHPO$_4$ hybrid nanoflowers. FIG. 37B graphically illustrates the storage stabilities of free GOx and Con A-GOx-CaHPO$_4$ hybrid nanoflowers in PBS (pH 6.8) at room temperature. FIG. 37C graphically illustrates the stability of Con A-GOx-CaHPO$_4$ hybrid nanoflowers within 30 d for detection of *E. coli* O157:H7 ($10^4$ Colony-forming unit (CFU) per mL).

FIG. 38 graphically illustrates the linear calibration curve for *E. coli* O157:H7 detection of changes in pH versus log of *E. coli* O157:H7 concentrations.

FIG. 41A shows the concentration of magnetic beads. FIG. 41B shows the concentration of BSA. FIG. 41C shows the dilution factors of the HRP-Ab2-Cu$_3$(PO$_4$)$_2$ nanoflowers. FIG. 41D shows the incubation time of the HRP-Ab2-Cu$_3$(PO$_4$)$_2$ nanoflowers. The solid and dashed lines reflect the optical densities obtained from the assays without or with $1\times10^3$ CFU/mL *S. enteritidis*, respectively.

DETAILED DESCRIPTION

Figure 2A:
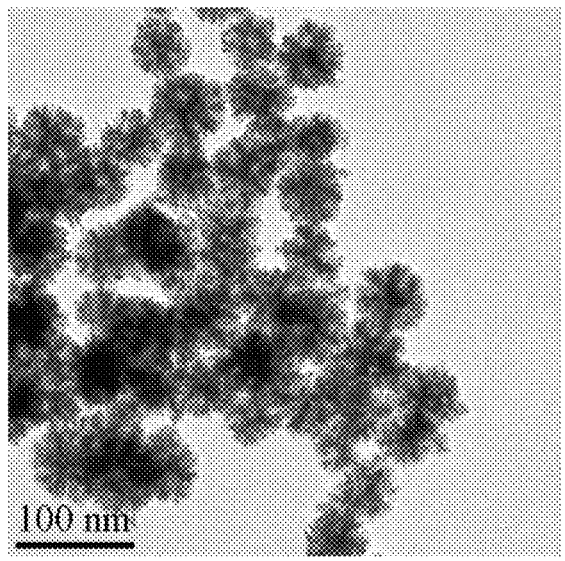
FIGS. 2A-2D are electronic microscopic images of Pt—Au porous NPs.

The present disclosure is generally directed to reagents and related systems, kits, and methods for detecting and/or quantifying target antigens. As described in more detail below, the inventors have developed novel reagents and configurations to provide amplified signals for the sensitive and facile detection and quantification of target antigens. The disclosed reagents comprise an inorganic component that provides and/or enhances catalytic function of the reagent, resulting in efficient signal amplification. The disclosed reagents can be configured, for example, as primary detection reagents or secondary detection reagents for use in a variety of assay formats, such as in a sandwich-type immunoassay for a target antigen. The assay formats can be readily configured for detection and/or quantification using a variety of available meters or even cell phones.

As described in more detail below, the non-organic component can be metallic nanoparticles (e.g., Pt—Au or Pt—Pd bimetallic nanoparticles) that possess catalytic functionality themselves. These can be used as a replacement or alternative to an enzymatic reporter component typically known in standard ELISA designs. Alternatively, the non-organic component can provide nanoflower structures to serve as a scaffold onto which high amounts of antigen binding and detection (i.e., catalytic) components can be mounted. The ability to mount high concentrations of antigen binding and detection reagents on a single scaffold component enhances the antigen binding and catalytic capacity, efficiency, and/or stability of the detection reagent as compared to standard antibody/enzymatic conjugates presently used.

In accordance with the foregoing, in one aspect, the disclosure provides antigen detection reagent. The antigen detection reagent comprises an antigen-binding molecule conjugated to an inorganic component.

As used herein, the term "antigen" refers to any particular molecule or moiety of interest for which detection and/or quantification is desired without limitation except that the antigen must be capable of being specifically bound by a binding molecule, as described below. The antigen can be a "target antigen," such as a biomarker for a condition, disease, or presence of an infectious agent. As a non-limiting example, the antigen can be a cell-surface receptor or excreted protein that is characteristic of a transformed cell or pathogen. In another example, the antigen can be protein that is an allelic variant, a phosphorylated form, or is in a misfolded state as compared to a reference protein. In other non-limiting embodiments, the antigen can be an environmental factor, such as a contaminant or allergen. Alternatively, the antigen is a component of a primary detection reagent, such as a domain in the constant region of an antibody that itself specifically binds to a target antigen. In such cases, the detection reagent as disclosed herein functions as a secondary detection reagent and the primary detection reagent specifically binds to a "target antigen" (e.g., allergen, environmental antigen, and/or disease/pathogen marker, as described above). In this context, the "antigen of interest" bound by the disclosed antigen-binding reagent is a component of the primary detection reagent, whereas the primary detection reagent binds (e.g., specifically binds) to a "target antigen," which is the antigen for which the assay is being performed.

As used herein, the term "antigen-binding molecule" refers to any molecule having an ability to bind to a specific molecule (i.e., antigen of interest and/or target antigen) with a specific affinity (i.e., detectable over background). The antigen-binding molecule, as described herein, refers to a component or subdomain of the novel antigen detection reagent described in more detail below. The antigen-binding molecule can be routinely determined and incorporated into the antigen detection reagent by persons of ordinary skill in the art depending on the specific application at hand, i.e., depending on what antigen of interest and/or target antigen the reagent is being directed to. Near-countless numbers of antigen-binding molecules are known and have been characterized for useful antigens and are encompassed by the present application without limitation. It is the organization of the antigen-binding molecule in connection with the inorganic compounds that advance the disclosed reagent and related methods and systems over the art.

Exemplary, non-limiting, categories of antigen-binding molecules that can be used in the context of the present invention include antibodies, antibody derivatives (also referred to as "antibody-like molecules"), functional antigen-binding portions of antibodies or antibody-like molecules, peptides that specifically interact with a particular antigen (e.g., peptibodies), receptor molecules that specifically interact with a particular antigen, functional antigen-binding portions of proteins that comprise a ligand-binding portion of a receptor that specifically binds a particular antigen, ligands themselves (or moieties that incorporate a ligand), antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, Curr. Opin. Biotechnol. 22:849-857, 2011, and references cited therein, incorporated herein by reference]), aptamers or antigen binding portions thereof, and nucleic acid molecules with sequences sufficiently complementary to a target "antigen" nucleic acid sequence so as to promote hybridization.

In some embodiments, the affinity reagent is an antibody. As used herein, the term "antibody" encompasses antibodies and antibody fragments thereof, derived from any antibody-producing mammal (e.g., mouse, rat, rabbit, and primate including human), that specifically bind to an antigen of interest. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies. The antigen-binding molecule can be any intact antibody molecule or fragment thereof (e.g., with a functional antigen-binding domain).

An antibody fragment is a portion derived from or related to a full-length antibody, preferably including the complementarity-determining regions (CDRs), antigen binding regions, or variable regions thereof. Illustrative examples of antibody fragments useful in the present disclosure include Fab, Fab', F(ab)$_2$, F(ab')$_2$ and Fv fragments, scFv fragments, diabodies, linear antibodies, single-chain antibody molecules, multispecific antibodies formed from antibody fragments, and the like. A "single-chain Fv" or "scFv" antibody fragment comprises the $V_H$ and $V_L$ domains of an antibody, wherein these domains are present in a single polypeptide chain. The Fv polypeptide can further comprise a polypeptide linker between the $V_H$ and $V_L$ domains, which enables the scFv to form the desired structure for antigen binding. Antibody fragments can be produced recombinantly, or through enzymatic digestion.

Antibodies can be further modified to suit various uses. For example, a "chimeric antibody" is a recombinant protein that contains domains from different sources. For example, the variable domains and complementarity-determining regions (CDRs) can be derived from a non-human species (e.g., rodent) antibody, while the remainder of the antibody molecule is derived from a human antibody. A "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions (CDRs) are of non-human origin.

Production of antibodies can be accomplished using any technique commonly known in the art. For example, the production of a polyclonal antibody can be accomplished by administering an immunogen containing the antigen of interest to an antibody-producing animal. For example, the antigen of interest (also referred to as "target antigen") can be administered to a mammal (e.g., a rat, a mouse, a rabbit, a chicken, cattle, a monkey, a pig, a horse, a sheep, a goat, a dog, a cat, a guinea pig, a hamster) or a bird (e.g., a chicken) so as to induce production of a serum containing an antigen-specific polyclonal antibody. The target antigen can be administered in combination with other components known to facilitate induction of a B-cell response, such as any appropriate adjuvant known in the art. Furthermore, the polyclonal antibody reagent can be further processed to remove or subtract any antibody members that have unacceptable affinity for antigens that are not the antigen of interest. The resulting polyclonal antibody reagent will exhibit enhanced specificity for the antigen of interest and are useful for detection and quantification purposes. Many approaches for adsorption of polyclonal antibody reagents to reduce cross-reactivity exist, are familiar to persons of ordinary skill in the art, and are encompassed by the present disclosure.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art.

Antibody fragments and derivatives that recognize specific epitopes can be generated by any technique known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain. Further, the antibodies of the present invention can also be generated using various phage display methods known in the art. Finally, the antibodies, or antibody fragments or derivatives can be produced recombinantly according to known techniques.

As used herein, the term "aptamer" refers to oligonucleic or peptide molecules that can bind to specific antigens of interest. Nucleic acid aptamers usually are short strands of oligonucleotides that exhibit specific binding properties. They are typically produced through several rounds of in vitro selection or systematic evolution by exponential enrichment protocols to select for the best binding properties, including avidity and selectivity. One type of useful nucleic acid aptamers are thioaptamers, in which some or all of the non-bridging oxygen atoms of phophodiester bonds have been replaced with sulfur atoms, which increases binding energies with proteins and slows degradation caused by nuclease enzymes. In some embodiments, nucleic acid aptamers contain modified bases that possess altered sidechains that can facilitate the aptamer/target binding.

Peptide aptamers are protein molecules that often contain a peptide loop attached at both ends to a protamersein scaffold. The loop typically has between 10 and 20 amino acids long, and the scaffold is typically any protein that is soluble and compact. One example of the protein scaffold is Thioredoxin-A, wherein the loop structure can be inserted within the reducing active site. Peptide aptamers can be generated/selected from various types of libraries, such as phage display, mRNA display, ribosome display, bacterial display and yeast display libraries.

In some embodiments, the antigen-binding molecule is a receptor molecule or comprises a binding domain of a receptor molecule. The receptor molecule can be any receptor known that can specifically bind the antigen of interest as the ligand. As a non-limiting example, the antigen-binding domain can be a lectin molecule, such as concanavalin A (ConA) which can bind to sugars appearing on the E. coli outer membrane. In another embodiment, the antigen-binding molecule is or contains a protein binding domain that enables the detection of the target protein as the antigen of interest. In yet another embodiment, the antigen-binding molecule can be or comprise a ligand or portion of a ligand that is specific for a receptor or a binding domain of a protein, which receptor or a binding domain of a protein would then serve as the antigen of interest.

As used herein, the term "selectively binds" refers to the ability of the antigen-binding molecule to bind to the antigen of interest, without significant binding to other molecules, under standard conditions known in the art. The antigen-binding molecule can bind to other peptides, polypeptides, or proteins, but with lower affinity as determined by, e.g., immunoassays, BIAcore, or other assays known in the art. However, antigen-binding molecule preferably does not cross-react with other antigens.

The inorganic component refers to a component, subdomain, or moiety of the antigen detection reagent that is distinct from the antigen-binding molecule. The term "inorganic component" refers broadly to the characteristic that this component is not a nucleic acid or polypeptide polymer and does not rely on carbon to carbon bonds for its primary structure.

As indicated above, the inorganic component can possess catalytic functionality, such as peroxidase functionality, that converts a substrate into a product. This conversion results in a detectable change, such as a color change, pH, change, and the like, that is detectable and indicative of the presence or amount of the antigen detection reagent. Under certain assay conditions, this is indicative of the presence or amount of a particular antigen being assayed.

In some embodiments, the inorganic component is or comprises bimetallic nanoparticles (NPs). The catalytic functionality of the bimetallic NPs can be leveraged to produce detectable signals when immobilized (via direct or indirect binding to a target antigen) through its catalytic conversion of a substrate to a product. Furthermore, such bimetallic NPs offer advantages over traditional catalytic molecule, such as enzymes, for generating reporting signals because they are more stable and are operative over a wider range of reaction conditions than protein-based enzymes. Furthermore, there are distinct advantages to the relative ease and cost of their manufacture, incorporation into the disclosed antigen detection reagent, and long-term storages. In one embodiment, the bimetallic nanoparticle is a particle represented by Pt-M, wherein M is Au, Pt, Co, Ni, Fe, or other metals that provide catalytic activity to the bimetallic NP component. Exemplary, non-limiting examples of bimetallic NPs include platinum (Pt)-gold (Au) bimetallic nanoparticle (Pt/Au NP), a platinum (Pt)-palladium (Pd) bimetallic nanoparticle (Pt/Pd NP), a platinum (Pt)-cobalt (Co) bimetallic nanoparticle (Pt/Co NP), a platinum (Pt)-nickel (Ni) bimetallic nanoparticle (Pt/Ni NP), or a platinum (Pt)-iron (Fe) bimetallic nanoparticle (Pt/Fe NP), each of which exhibit useful peroxidase activity. Thus, the presence of the bimetallic NPs can be detected by their catalytic action on an appropriate substrate, such as the oxidation of the chromatographic compound 3,3',5,5'-tetramethylbenzidine (TMB) to provide a quantifiable color change. Another exemplary peroxidase substrate is o-phenylenediamine dihydrochloride (oPD), which yields a yellow-orange product when reacted with a peroxidase. Other known catalytic bimetallic NPs and their corresponding detectable substrates/products are known and are encompassed by the present disclosure. Exemplary methods of making such bimetallic NPs and incorporating them into the disclosed detection reagents are described in more detail in Examples 1-3 below.

Alternatively, the inorganic component of the detection reagent can lack direct catalytic activity by itself, but instead can provide a physical scaffold to support the loading of one or more antigen-binding molecules and one or more reporter components. By loading, oftentimes a large plurality of antigen-binding molecules and reporter components, the inorganic components aggregates plurality of active components. This promotes the stability of the active components and ultimately provides for additional avidity of the antigen detection reagent and amplification of the detectable signals provided by the reported components. The scaffold can be provided by, for example, inorganic nanoflower structures, which are known in the nanotechnology arts, and are described in more detail in Examples 4-7. The inorganic nanoflowers can be or comprise inorganic compositions such as $Cu_3(PO_4)_2$, $Mn_3(PO_4)_2$, and $CaHPO_4$. Exemplary methods of making such inorganic nanoflowers and incorporating the antigen-binding molecules and reporter components therein are described in more detail below in Examples 4-7.

As indicated, embodiments of the antigen detection reagent incorporating inorganic nanoflowers can have an additional reporter component. There are typically a plurality of the same reporter component (e.g., multiple units of the same enzyme or bimetallic NP) or a plurality distinct reporter components (e.g., one or multiple units of distinct enzymes and/or bimetallic NPs). Further discussion of the reporter component is presented in the singular tense for simplicity, however it will be understood that any comments can be applied in the context of having additional units of the same or different reporter units loaded onto the same nanoflowers-based composition.

The reporter component can be any molecular component that provides a detectable signal. Such signals can be light emissions, such as provided by chemiluminescent or fluorophore tags, which are well-known in the art. Exemplary, non-limiting fluorophores include fluorescein (FITC), rhodamine, GFP, and phycobiliproteins (e.g., allophycocyanin, phycocyanin, phycoerythrin, and phycoerythrocyanin). Alternatively, signals can also be provided by isotope-incorporating molecules. Yet further, the signals can be provided by molecules with catalytic activity, such as enzymes (referred to as "reporter enzymes") or additional inorganic components such as the bimetallic NPs discussed elsewhere in this disclosure. Exemplary reporter enzyme components include horseradish peroxidase (HRP), alkaline phosphatase (AP), invertase, and glucose oxidase (GOx). Persons of ordinary skill in the art will be able to identify additional reporter enzymes that can be readily incorporated into the detection reagent and, thus, such enzymes are encompassed by the present disclosure. When provided with the appropriate substrate, these enzymes catalyze a conversion to a product that provides a detectable signal. For example, HRP can react with substrates such as ABTS, TMB, or oPD, to provide a color change, which can be detected and monitored routinely with appropriate equipment (including camera-equipped cell phones, as described below). Invertase converts sucrose to glucose, which can be readily quantified by the use of off-the-shelf personal glucose meters. Glucose oxidase (GOx) converts glucose to gluconic acid, which reduces the pH and can be monitored by a simple pH meter. Thus, when properly incorporated with appropriate substrates and, these reporter components produce detectable signals such as color changes, pH changes, glucose levels, and the like.

By the loading of large pluralities of antigen-binding molecules and reporter components (e.g., enzymes or inorganic bimetallic NPS), the signal production is greatly amplified for extra-sensitive detection. Furthermore, as discussed in more detail in Examples 4-7, the strengths of the detectable signals are shown to correlate very well to the amount of target antigen in the samples. Accordingly, the signals are useful for accurate quantification of the target antigen.

The detection reagents described herein can comprise its distinct components (e.g., the antigen-binding, reporter component, and, if separate, the inorganic component) in covalent or non-covalent conjugation.

The antigen-binding molecule can be conjugated, directly or indirectly, to the catalytic "detection" or "reporter" components using any acceptable method or structure known in the art. For example, the conjugation can include a covalent bond between the antigen-binding molecule and any component of the catalytic "detection" or "reporter" component. Alternatively, the conjugation can include a non-covalent bond between the antigen-binding molecule and any component of the of the catalytic "detection" or "reporter" component. Such conjugation arrangements are typical for embodiments where the inorganic component is used for its catalytic reporting capacity, such as the bimetallic NPs described above.

In some embodiments, the antigen-binding molecule is not directly conjugated to the catalytic "detection" or "reporter" component itself, but rather both are conjugated to the inorganic scaffold, such as the nanoflowers. Thus, both are still conjugated to the same vehicle and are operative together, even without direct conjugation. Such conjugation arrangements can be implements particularly with the nanoflowers based reagents (described below for some embodiments as "3-in-1" or "protein-protein-nanoflower" reagents). However, in some embodiments, the antigen-binding molecule and the catalytic "detection" or "reporter" component can be directly conjugated and then the chimeric structure can be loaded (e.g., further conjugated) to the inorganic scaffold (e.g., nanoflowers).

A covalent bond can be accomplished by functionalizing the components for subsequent covalent binding between the antigen binding molecule and the catalytic detection component(s). For example, techniques such as amine modification, carbohydrate modification, disulfide modification can be utilized to functionalize the surface of the components for covalent attachment of the antigen-binding molecule.

In other embodiments, the antigen-binding molecule is non-covalently tethered to the catalytic detection component(s). For example, as is well-known in the art, biotin forms non-covalent bonds with streptavidin and avidin, with high specificity and affinity (Kd of 10-14 mol/l to 10-15 mol/l). Thus, as in the specific example described in more detail below, amphiphilic molecules incorporating biotin, such as DSPE-biotin, can be included in the catalytic detection component(s), and avidin or streptavidin-containing antigen binding molecules can be contacted thereafter to form a noncovalent tether between the catalytic detection component(s) and the antigen-binding molecule. However, it will be appreciated that the arrangement of the biotin and avidin/streptavidin moieties can be switched between the catalytic detection component(s) and antigen-binding molecule to achieve the same noncovalent tethering.

In view of the above, a few illustrative non-limiting embodiments are provided. Further descriptions addressing how to make such embodiments, and specific applications of such embodiments, are provided in the Examples.

In one embodiment, an antibody or antigen-binding fragment or derivative thereof is conjugated to a bimetallic nanoparticle. In a further embodiment, the bimetallic nanoparticle is a Pt—Au nanoparticle, as described in Example 1. In alternative embodiments, the bimetallic nanoparticle is a Pt—Pd nanoparticle, as described in Examples 2 and 3. In some embodiments, the antibody or antigen-binding fragment or derivative thereof specifically binds to a pathogen, such as *E. coli* or *Salmonella* sp., as described in Examples 1 and 2. These types of reagents are useful for the detection or quantification of pathogens/contaminants in consumable products (such as food or drinks). In other embodiments, the antibody or antigen-binding fragment or derivative thereof can specifically detect a disease marker, such as p53 protein. See Example 3. However, it will be understood that the antigen-binding molecule need not be antibody based, but can be an alternative antigen binding molecule, as described above. For example, Examples 5 and 6 describe the use of a lectin, ConA, to bind and detect bacterial pathogens. These reagents can be incorporated into a variety of assay formats, including lateral flow immunoassays or ELISA-type assays in multi-well plates, by applying the appropriate catalytic reporter substrate. For example, each of the Pt—Au NPs and Pt—Pd NPs oxidize TMB to produce a detectable color change. The color change can be detected using readily available detector devices, including cell phones equipped with cameras (see, e.g., Example 2).

In another embodiment, the antigen detection reagent comprises a nanoflower structure that is or comprises at least one of $Cu_3(PO_4)_2$, $Mn_3(PO_4)_2$, and $CaHPO_4$. See Examples 4-7. For example, in one embodiment, an antibody and HRP reporter component are conjugated to a $Cu_3(PO_4)_2$ nanoflower to provide a 3-in-1 protein-protein-nanoflower reagent for the detection of an antigen. See e.g., Example 4, which utilizes an antibody specific for *E. coli*. With HRP, an assay can be performed by allowing potential immobilized antigen-reagent complexes to TMB and assessing for a color change to determine the presence or amount of *E. coli*. Alternatively, the HRP can be substituted by another reporter component, such as GOx. With GOx, the detectable signal indicating the presence or amount of bound antigen is the reduction in pH as determined by a common pH meter.

In another embodiment, a lectin ConA and invertase reporter component are conjugated to a $CaHPO_4$ nanoflower to provide a 3-in-1 protein-protein-nanoflower reagent for the detection of E. coli. The assay is performed by exposing the bound E. coli with sucrose. The invertase converts the sucrose to glucose, which can then be detected or quantified by a personalized glucose meter. See, e.g., Example 5.

In yet another embodiment, a lectin ConA and GOx reporter component are conjugated to a $CaHPO_4$ nanoflower to provide a 3-in-1 protein-protein-nanoflower reagent for the detection of E. coli. As indicated above, the assay can be performed by exposing the E. coli with glucose. The GOx converts the glucose gluconic acid, which can then be detected or quantified by a pH meter. See, e.g., Example 6.

It will be understood that with any of these embodiments, the reagent can be designed to detect the antigen of choice. For example, instead of an anti-E. coli antibody or lectin, the antigen-binding molecule can selectively bind Salmonella (as in Examples 2 or 7), or an endogenous disease marker, such as p53 protein (see Example 3).

The antigen detection reagent compositions described herein can be incorporated into target antigen detection assays and methods according to ordinary skill in the art. It will be readily apparent that the disclosed reagents can be incorporated as detection reagents (e.g., a primary or secondary detection reagents) in any immunoassay format such as a sandwich ELISA. When the disclosed antigen-detection reagent serves as a secondary detection reagent, the antigen-binding molecule will be specific for an epitope on the primary detection reagent, such as the constant region of the primary detection antibody.

Accordingly, in another aspect, the disclosure provides a method of detecting an antigen of interest. The method comprises contacting a sample with the antigen detection reagent as described herein under conditions sufficient to permit the selective binding of the antigen detection reagent to the antigen of interest, and detecting the presence of the antigen of interest.

In some embodiments, the detecting the presence of the antigen of interest further comprises quantifying the antigen of interest in the sample. This can be performed, for example, by comparing the detected signal intensity or level to a control amount or curve, accordingly to ordinary skill in the art.

In some embodiments, the antigen detection reagent itself produces a detectable signal (e.g., by fluorescent or chemiluminescent signal) and thus, can provide a relevant signal when it is immobilized by virtue of binding to antigen.

In other embodiments, the antigen detection reagent comprises a catalytic reporter component and, thus, the detecting of the product comprises contacting the bound antigen detection reagent with a substrate, thereby producing a product, and detecting or quantifying the presence of the product. In some embodiments, the conversion of the substrate to the product provides a detectable signal. For example, the substrate and/or its product can be a chromogenic reagent, such as TMB. Catalytic reporter moieties and their substrates are described in more detail above and below.

The antigen of interest can be immobilized such as by crosslinking to a substrate (e.g., the bottom of a well) or by binding to a capture reagent that is itself immobilized on a substrate. In some embodiments, the capture reagent is conjugated, covalently or noncovalently, to a magnetic particle to facilitate immobilization by the application of a magnetic field. See, e.g., Example 7. This permits the immunomagnetic separation (IMS) of the target antigen from other components of a sample.

Assays can incorporate multi-well formats or lateral flow formats. Furthermore, assays can be run in solution with potential immobilization (to facilitate removal of unbound reagents) using magnetic solid substrates in conjunction with application of a magnetic field.

Also provided are kits and systems for detecting target antigens in a sample, the kits and systems comprise the detection reagents described herein. In some embodiments, the kits and systems can further comprise relevant capture reagents. In some embodiments, the kits and systems can further comprise primary detection reagents. Additionally, the kits and systems can comprise additional hardware, such as lateral flow set ups and devices, or multi-well plate substrates for performance of the assays, and buffers to facilitate the flow and/or binding of reagent to antigen. The kits and systems can include or be configured to incorporate use of the appropriate detection devices, such as colorimetric readers, pH meters, glucose readers, camera-equipped cell phones, and the like, which ultimately detect and/or quantify the detectable signals indicating the presence and/or amount of the bound antigen.

Unless specifically defined herein, all terms used herein have the same meaning as they would to one skilled in the art of the present invention. Practitioners are particularly directed to Sambrook J., et al. (eds.) *Molecular Cloning: A Laboratory Manual,* 3rd ed., Cold Spring Harbor Press, Plainsview, N.Y. (2001); Ausubel F. M., et al. (eds.), *Current Protocols in Molecular Biology,* John Wiley & Sons, New York (2010); and Coligan J. E., et al. (eds.), *Current Protocols in Immunology,* John Wiley & Sons, New York (2010) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are reagents, materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are provided for the purpose of illustrating, not limiting, certain embodiments of the material disclosed herein.

Example 1

This Example describes the sensitive detection of *Escherichia coli* (O157:H7 serotype) using Pt—Au bimetal nanoparticles with peroxidase-like amplification.

Abstract: *Escherichia coli* O157:H7 is one of the most notorious foodborne pathogens causing serious disease at low infectious dose. To protect consumers from deadly foodborne *E. coli* O157:H7 infection, it is vital to develop a simple, reliable, sensitive and rapid method which can detect low level *E. coli* O157:H7 in foods at real-time. We have successfully developed a novel immunochromatographic assay (ICA) with enhanced sensitivity for the visual and quantitative detection of *E. coli* O157:H7. Sandwich-type immunoreactions were performed on the ICA, and Pt—Au bimetal nanoparticles (NPs) were accumulated on the test zone. The signal amplification is based on Pt—Au bimetal NPs possessing high peroxidase activity toward 3,3',5,5'-tetramethylbenzidine, which can produce characteristic colored bands and thus, enable visual detection of *E. coli* O157:H7 without instrumentation. The innovative aspect of this approach lies in the visualization and quantification of target pathogen through the detection of color intensity. Due to the excellent peroxidase activity of Pt—Au NPs, they emit strong visible color intensity in less than 1 min for visual observation even in low concentration range of *E. coli* O157:H7. Quantification was performed using a commercial assay meter. The sensitivity was improved more than 1000-folds compared to the conventional test strip based on colored gold-colloids. Although the feasibility was demonstrated using *E. coli* O157:H7 as a model analyte, this approach could be readily developed from this disclosure into a universal signal amplification technique and applied to detection of a wide variety of foodborne pathogens and protein biomarkers.

1. Introduction

*Escherichia coli* O157:H7 is an important foodborne pathogen that has low infectious dose and causes serious illness in humans, including bloody diarrhea and hemolytic uremic syndrome and even death. Enterohemorrhagic *E. coli* (EHEC) cause more than 63,000 illnesses, 2100 hospitalizations and 20 deaths each year in the United States, of which *E. coli* O157:H7 is the main EHEC serotype that causes the majority of EHEC human infections. *E. coli* O157:H7 is involved in a variety of foodborne outbreaks associated with ground beef, fresh produce, rice cakes, dairy products and others. At present, USDA has a zero tolerance policy to control *E. coli* O157:H7 contamination in ground beef. Additionally, along with *Salmonella* spp. and *Listeria monocytogenes*, *E. coli* O157:H7 foodborne outbreak has been an emerging issue for fresh produce, as reflected in nationwide *E. coli* O157:H7 spinach outbreaks that sickened more than 200 people and killed 3 people. In response to low infectious dose and devastating consequences of fresh produce outbreak, the FDA Food Safety Modernization Act targets the safety of fresh and minimally processed foods. Hence, developing a rapid, sensitive, and accurate method to detect *E. coli* O157:H7 in various foods with complex matrix and extreme pH is crucial in preventing disastrous *E. coli* O157:H7 outbreaks and associated human infection.

The expanding requirements for reliable diagnostic techniques of infectious agents in food have attracted intensive attentions to develop varieties of diagnostic strategies, such as cell phone based diagnostics, new kinds of fluorescence signal amplification reporters and various kinds of nanomaterials based biosensors. As one of the most promising assays for point of care diagnostic, immunochromatographic assay (ICA), is widely used for individual pregnancy diagnosis. The principle of ICA is a sandwich immunoreaction. After the sample was added to the membrane, it started to react with captured antibody (Ab1) to form a complex, which began to pass along the nitrocellulose membrane by capillary action until reaching the detection antibody (Ab2) in the test zone to achieve the sandwich immunoreaction. ICA has advantages over the most common assays, such as bacterial culture and ELISA, because of its low cost, easy operation, rapid, quantitative detection, and accuracy.

Colloidal golds served as labels to develop ICA has been applied for the detection of branches of analytes because of its high level of photo brightness, promising chemical stability and strong bio-compatibility; whereas the detection limit of most reported ones cannot detect low levels of foodborne pathogens or infectious agents. Thus, great efforts have been made to improve the sensitivity of ICA using different labels. ICA-utilizing nanomaterials, such as quantum dots, bio-conjugated nanoparticles (NPs) probe, colored latex particles and up-converting phosphors, exhibits higher detection sensitivity and broader response range than colloidal gold-based conventional ICA. However, the increased sensitivity brings several drawbacks. Their chemical instability, expensive instruments requirements and long handling time limit them from facilitating quantitative analysis in food industry at real time. Also, the industrial authority usually regards rapid bacterial detection as a method which can be done within fifty minutes. Therefore, it is extremely critical to establish a low cost, rapid and ultrasensitive method with systematic signal amplification protocol for visual detection of pathogens.

With the high surface area, diversified composition and excellent electron conductivity, the porous bimetallic NPs have provided excellent catalytic performance and have been addressed as promising nanomaterial from decades of biomedical research. For instance, the Pt or Au based bi-metallic NPs have been broadly utilized in the biomedical field because of strong catalytic activity and unique biocompatibility. Specifically, Pt-based NPs is the most research-attractive material because of its wide application in catalysis, sensing, biomedical diagnosis and therapy, etc. Additionally, porous bimetal NPs usually exhibit better thermo-stability than enzymes, which require appropriate conditions to keep their three-dimensional structures for their functionality. Hence, these specific characteristics offer great potential in developing ICA to detect foodborne pathogens in food and food processing environments, which usually have a very complicated matrix and acidity, capable of inhibiting enzymatic reaction.

Herein, we report a novel Pt—Au NP-based ICA for easy-operation and rapid detection of $E.$ $coli$ O157:H7 with high sensitivity resulting from the amplification of peroxidase activity of Pt—Au NPs. 3,3',5,5'-Tetramethylbenzidine (TMB), a chromogenic reagent, served as a good signal amplifier because it could be catalyzed by Pt—Au NPs producing blue color products, which provides higher visible sensitivity than other classic substrates (see, e.g., He, W., et al., 2011. Biomaterials 32, 1139-1147). Under the optimal condition, the detection limit of new device is $10^2$ cells $mL^{-1}$, which was about 1/1000 of the recent conventional colloidal based ICA ($10^5$ cells $mL^{-1}$, see, e.g., Wang, J., et al., 2006, Wei Sheng Yan Jiu 35, 439-441.). Experimental results demonstrated that the Pt—Au based ICA provides a reliable, rapid, sensitive strategy for visual detection of pathogen. Pt—Au based ICA has a great potential for point of care application in clinical diagnostics and food industry.

2. Experimental Section 2.1 Materials and Chemistry $E.$ $coli$ O157:H7 EDL933 was obtained from the STEC center at Michigan State University. The strain was stored in Luria Broth (LB, Fisher Scientific, Pittsburgh, Pa.) medium containing 15% glycerol at 80° C., and was activated in LB broth at 37° C. overnight with aeration.

Horseradish peroxidase (HRP), 3,3',5,5'-Tetramethylbenzidine (TMB), TMB Liquid Substrate System for ELISA which contains concentration of $H_2O_2$, Pluronic F127, $K_2PtCl_4$ (Pt, 44.99%), $HAuCl_4$ (Au, 49.98%), commercial Pt carbon nanopowder, hydrochloric acid (HCl, 39%), polyvinylpyrrolidone (PVP), sodium hydroxide (NaOH) and ascorbic acid were purchased from Sigma-Aldrich. Fetal bovine serum (FBS) and bovine serum albumin (BSA) were purchased from ATCC. Mouse anti-$E.$ $coli$ O157:H7 polyclonal antibody (Ab1), mouse anti-$E.$ $coli$ O157:H7 monoclonal antibody (Ab2) were purchased from Kirkegaard & Perry Laboratories Inc (Baltimore, Md.). Nitrocellulose membrane, fiber sample pad, fiber conjugate pad, laminated cards, and absorbent pad were used by provided. Ultrapure water from Millipore Milli-Q water purification system was used for experiments. The phosphate buffered saline (PBS) containing $Na_2HPO_4$ and $NaH_2PO_4$ was prepared using de-ionized water (18.2 MΩ cm), and the pH was adjusted with NaOH and $H_3PO_4$. All the reagents are analytical standard and used without further purification.

2.2 $E.$ $coli$ O157:H7 Sample Preparation

Overnight $E.$ $coli$ O157:H7 cultures were washed with 1×PBS, pH 7.0 and re-suspended in 1×PBS. A portion of washed $E.$ $coli$ O157:H7 suspension was serial diluted and proper dilutions were plated on LB agar plates for cell enumeration. The remaining $E.$ $coli$ O157:H7 suspension was heated in 95° C. water bath for 30 min, then formalin was added to a final concentration of 0.5% (v/v). Mortalized $E.$ $coli$ O157:H7 were used for safety reasons and to ensure a static (non-proliferating) sample population for quantitative purposes.

2.3 Preparation of Porous Pt—Au NPs

Pt—Au NPs was synthesized as previously described (Ataee-Esfahani, H., et al., Angewandte Chemie International Edition 2013, 52. 13611-13615) with slight modifications. Pluronic F127 (10 mg) was ultrasonically dissolved into 1.0 mL of aqueous solution containing $K_2PtCl_4$ (20 mM), $HAuCl_4$ (20 mM) and HCl (6 M). After adding 1.0 mL of ascorbic acid (100 mM), the reducing agent, the mixture was continuously sonicated in a water bath for 0.5 h, and then reacted with a magnetic stirrer for 24 h at 30° C. The final product was collected, washed with acetone and water in consecutive washing/centrifugation cycles five times, and then dried at room condition.

2.4 Preparation of Pt—Au-Capture Antibody (Ab1)

The pH of the Pt—Au NPs solution was optimized by adding 0.02 M $K_2CO_3$ before the capture antibody was added. Desired weight of capture antibody was mixed with desired amount of Pt—Au NPs, followed by gentle shaking for 1 h at room temperature. Then, 10 wt % BSA was added to a final concentration of 1% BSA, and the mixture was incubated for 30 min. The mixture was further washed with PBS with 1% BSA and centrifuged at 8000 rpm for 10 min. The prepared Pt—Au-capture antibody conjugates were collected and suspended in eluent buffer (pH 7.4, containing 10 mM PBS, 0.25% Tween-20, 10% sucrose, and 5% BSA). The total volume of solution after dissolving equals one tenth of the volume of the pervious solution of Pt—Au-capture antibody conjugates.

2.5 Preparation of Assay

FIGS. 1A-1D illustrate the test strip components schematically. The sample pad was pretreated with blocking buffer containing 10 mM PBS, 0.1% (w/v) Tween-20, and 1% (wt/v) PVP, pH 7.4. Pt—Au-antibody conjugates were dispensed onto the conjugated pad. Desired volume of mouse monoclonal anti-$E.$ $coli$ O157:H7 anti-body solution (0.8 mg $mL^{-1}$, $Ab_2$) was dispensed on the reaction membrane to form the test zone, and then was pretreated with blocking buffer. All the parts mentioned have to be dried 2 h at 37° C. before assembled on a plastic adhesive backing card, which was cut into 4 mm strips and stored at room condition.

2.6 Assay Procedure

50 μL of the analyte ($E.$ $coli$ O157:H7) was dropped onto the sample pad and diffused through the reaction membrane driven by the capillary force, which enabled the reaction with Ab1-labeled Pt—Au NPs to form complex at conjugation pad. The yielding complex then passed along the nitrocellulose membrane by capillary action until reaching the Ab2 in the test line to achieve the sandwich immunoreaction. After adding TMB, the final signal intensity on test line was observed and quantified using a test strip reader after the immunoreaction finishing.

2.7 Instruments and Characterization

The transmission electron microscopy (TEM) was conducted with Philips CM200UT. The scan electron microscopy (SEM) was conducted using FEI Quanta 200F. The Energy Dispersive X-ray Spectrometer (EDX) was obtained with FEI Quanta 200F. X-ray photoelectron spectroscopy (XPS) measurements were recorded on a Kratos AXIS-165 multi-technique electron spectrometer system with a base pressure of $1\times10^{-9}$ Torr. XPS were obtained on an AXIS-165 manufactured by Kratos Analytical Inc. (Spring Valley, N.Y., USA) using a monochromatic X-ray radiation of 1487 eV (Al Ka). The spectrometer was calibrated against both the Au 4f7/2 peak at 84.0 eV and the Ag 3d5/2 peak at 368.3 eV. Static charging when present was corrected with a neutralizer (flood gun) by placing the carbon peak (C 1s) at about 285 eV. A portable fluorescence strip reader ESE-Quant GOLD was purchased from DCN Inc. (Irvine, Calif.).

3. Result and Discussion 3.1 Characteristics of Pt—Au Porous Nanocolloids

Metal precursors can be reduced simultaneously by a strong reducing agent in liquid phase to form faceted crystal morphology, which is one practicable way to synthesize metallic alloy nanostructures. Additionally, self-assembly of surfactants into spherical micelles can employ faceted crystal as templates to synthesize porous metal NPs. The resulting bimetallic porous Pt—Au nanocolloids provide high surface area with abundant activity sites on the concave surface.

Figure 2B:
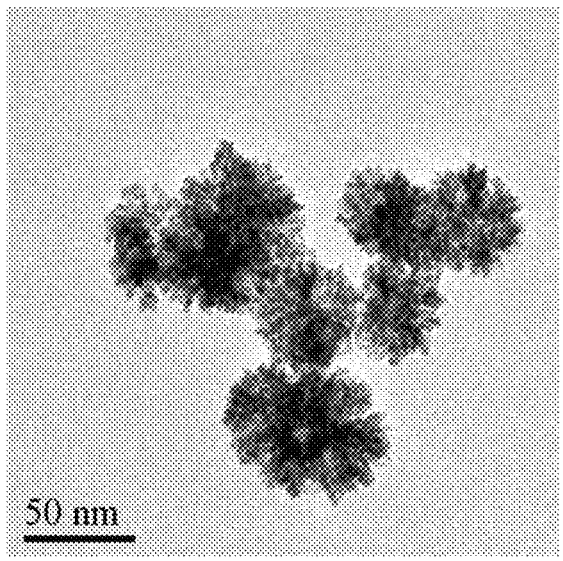
Figure 2C:
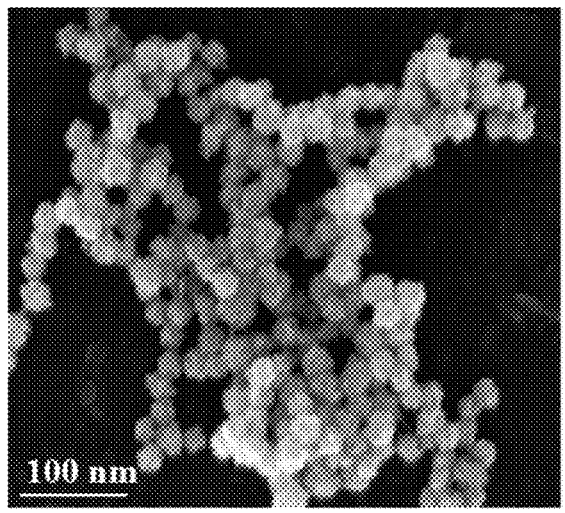
Figure 2D:
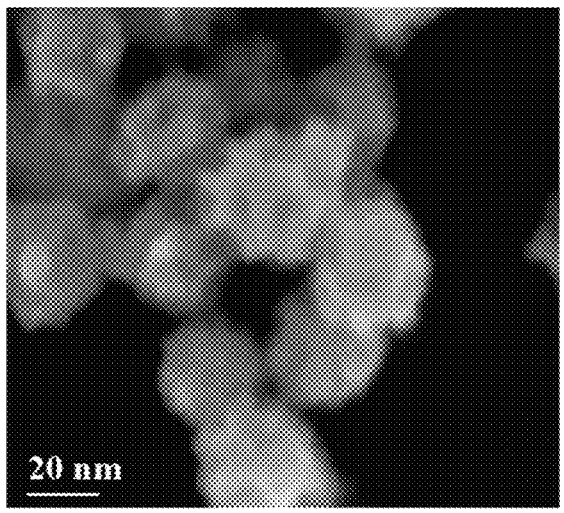

SEM and TEM were performed to characterize the morphology of Pt—Au porous NPs. The average size of NPs is around 50 nm. There is a uniform porous structure formed as hemispherical with concavities on the surface of NPs by TEM (FIGS. 2A-2B). This porous structure was further confirmed by SEM (FIGS. 2C-2D). The pores are made of fine Pt NPs that form several branched structure on the surface. The Pt NPs had an average diameter of 5 nm and were distributed evenly on the surface of Au NPs.

Furthermore, the formation of NPs was characterized by EDX spectroscopy. The corresponding EDX analysis confirmed peaks of presence of elemental Pt and Au in the porous NPs with an atomic Pt:Au ratio of 85.7:9.3, which was close to the stoichiometric ratio of the two metal precursors (9:1) (not shown). The surface properties were further analyzed by XPS; and the results showing the binding energy of Pt 4f and Au 4f (71.2 eV and 83.3 eV, respectively) are consistent with the metallic Pt—Au bimetallic nanostructure and agreed with the result from EDX (not shown).

3.2 Colorimetric Analyses of Peroxidase-Like Catalytic Activities of Pt—Au NPs

Figure 3A:
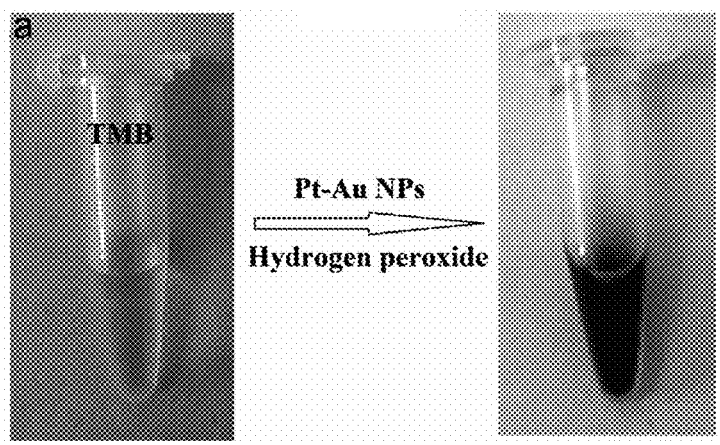
FIGS. 3A-3C.
Figure 3B:
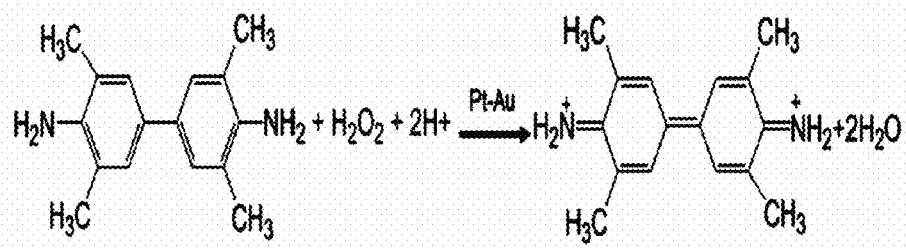

The peroxidase-like catalytic activities of Pt—Au NPs was studied by colorimetric tests using TMB—H2O2 substrate. In the presence of $H_2O_2$, Pt—Au NPs could catalyze $H_2O_2$-induced TMB oxidation, resulting in a deep blue color solution within 10 min (FIG. 3A). These results indicated that Pt—Au NPs behave as per-oxidase toward TMB oxidation with $H_2O_2$. The relative reaction is described in FIG. 3B, in which $H_2O_2$ served as electron acceptors.

Figure 3C:
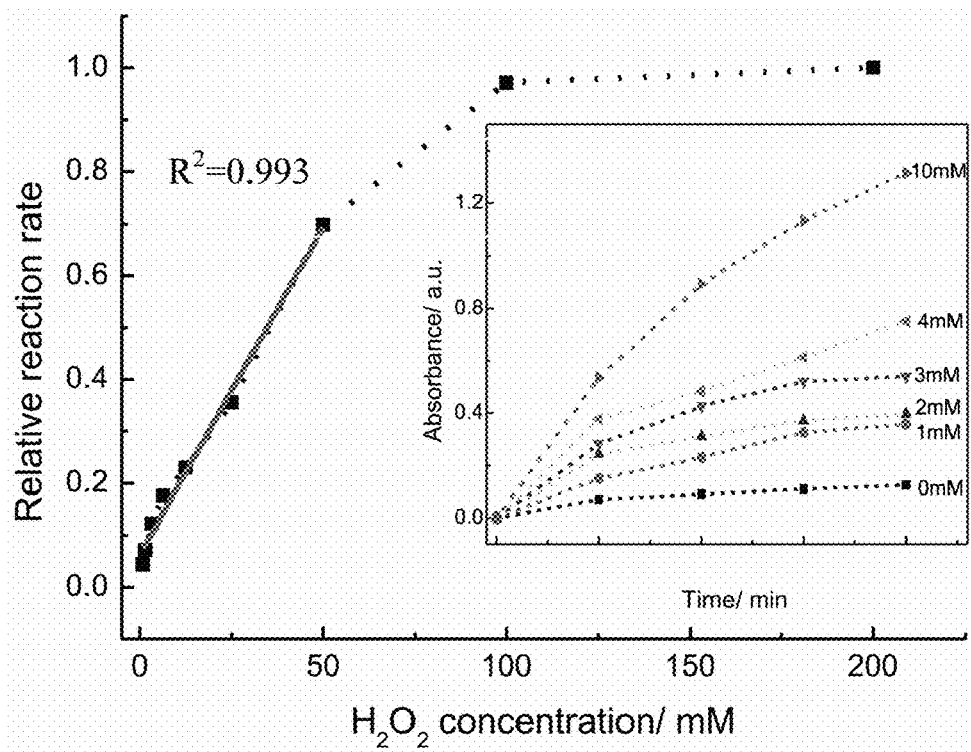

The relationship between the peroxidase-like activity of Pt—Au NPs and $H_2O_2$ concentrations was further studied (FIG. 3C). The reaction rate strongly depended on the $H_2O_2$ concentrations while it increased linearly (solid line) at low concentration range (0.5-20 mM). This could provide a potential detection method for $H_2O_2$ related detection. The inset of FIG. 3C is the absorbance evolution for different concentrations of $H_2O_2$ over time. When increasing the $H_2O_2$ concentration, the color intensity increased and reached the maximum value at 200 mM.

The peroxidase-like activity of Pt—Au NPs in different concentration ranges was investigated with TMB substrate and $H_2O_2$, in comparison with commercial Pt nanopowder. The color intensity of the reaction product depends on the Pt—Au NPs concentration ranging from 0.5 to 20 μg mL$^{-1}$, which is more sensitive than that of Pt nanopowder (not shown). When the NPs concentration increased from 0 to 20 mg mL$^{-1}$, the TMB—$H_2O_2$ assay of Pt—Au NPs achieved significantly higher sensitivity compared to Pt nanopowder (not shown). Pt—Au NPs could oxidize more TMB than Pt nanopowder under the same concentration of NPs. These results supported the hypothesis that Pt—Au NPs have stronger peroxidase-like activity than others. The data suggest that the Pt—Au NPs presented a good affinity for $H_2O_2$. Therefore, the Pt—Au NPs exhibit good catalysis performances, while they could have potential to circumvent intrinsic disadvantages of natural enzyme. Furthermore, the unique surface structure of Pt—Au NPs could significantly improve the surface area and better distribute Pt NPs, which may in turn facilitate greatly improvement of peroxidase-like catalysis activity of Pt—Au NPs.

The thermal and pH stability of Pt—Au NPs were further studied and compared with HRP. Pt—Au NPs exhibited a stable enzymatic catalytic activity toward $H_2O_2$ in the temperature range from 5 to 90° C., whereas the enzymatic activity of HRP drastically decreased over 40° C. due to the denaturalization of the enzyme under high temperature (not shown). Furthermore, Pt—Au NPs exhibited invariable activity in the solution with the pH range from 2 to 12; whereas the activity of HRP was significantly inhibited when the pH was lower than 7.0 and totally denaturized when pH dropped to 2 (not shown). Therefore, the demonstrated strong thermal and pH stability of Pt—Au NPs encourages varieties of biological and food applications which have complex matrix and variable pH and require strong and sensitive labels to serve as ultrasensitive reporter.

3.3 Principal of Pt—Au NPs as Colored Substrates in ICA

Figure 4:
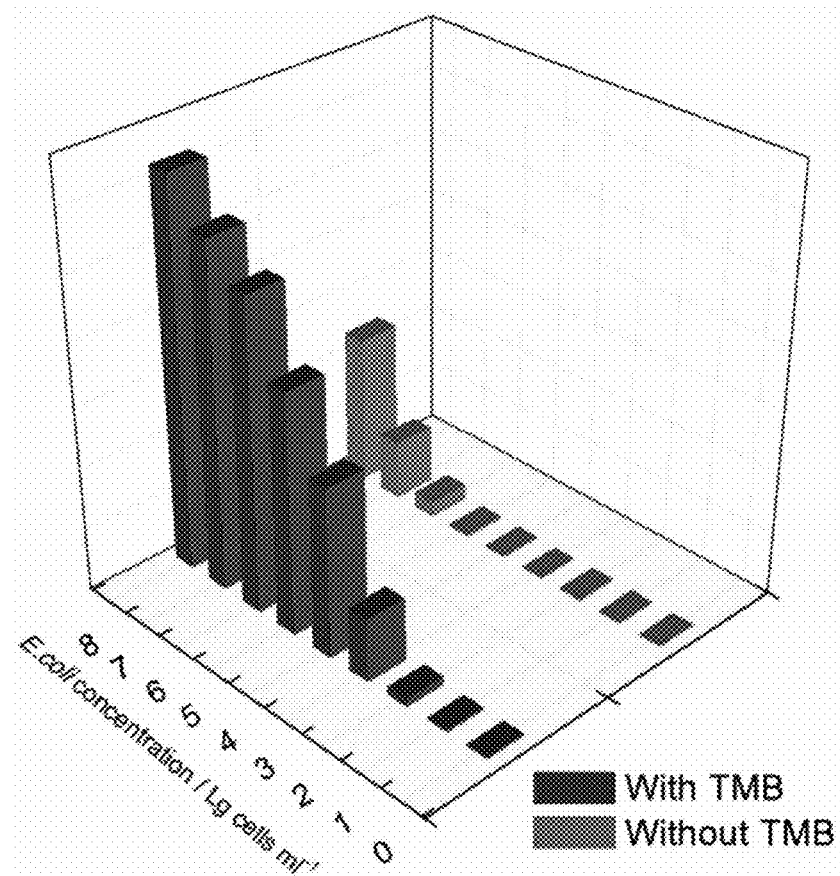
FIG. 4 graphically illustrates the reaction processes for the Pt—Au based ICA corresponding to different $E.\ coli$ O157: H7 concentrations. Without TMB the test line was observed only at high concentration range, whereas with TMB the color test lines occurred 5 min after adding TMB even under low $E.\ coli$ O157:H7 concentrations and the test zone turned into blue due to extreme high peroxidase activity. Typical intensity response curves using strip reader corresponding to the different $E.\ coli$ O157:H7 concentrations without or with TMB addition are illustrated.

FIG. 1 exhibits the schematically configuration and evaluation principle of the Pt—Au based ICA system. Capillary force draws the sample solution onto the dipped ICA. The effort of signal amplification was tested by recording different stages of the reaction of Pt—Au NPs and TMB, shown in FIG. 4. The Pt—Au labeled anti-*E. coli* O157:H7 Ab1 binds with *E. coli* O157:H7 forming *E. coli*-Pt—Au-Ab1 complex, and then releases from conjugate area to move through the nitrocellulose membrane until reaches the test zone. Clearly, the color intensity of the test line is proportional to the amount of accumulated Pt—Au NPs in the test zone associating with the *E. coli* O157:H7. The visibility of the dark color test line depends on the concentration of *E. coli* O157:H7 practically. With high concentration of *E. coli* O157:H7 sample (106-108 cells mL$^{-1}$), a visible line was observed; however with low concentration, the line could be fuzzy or almost invisible. In order to achieve ultrasensitive visual detection, TMB, a chromogenic reagent was used for this purpose. Since TMB can react with Pt—Au NPs resulting in products with blue color, it greatly amplified the signal. The clear visible blue lines were observed even at low concentration range of analyses ($10^2$-$10^5$ cells mL$^{-1}$) when signal-amplification was used. The optical density profiles of both with TMB and without TMB under different concentrations of analyses are shown in FIG. 4. The ICA with TMB has shown stronger optical intensity and lower detection range than the one without TMB. The results indicate that Pt—Au nanocolloids maintain extreme strong peroxidase activity on ICA and achieve greatly enhanced signal with addition of TMB.

3.4 Pt—Au Label Based ICA

To examine the signal amplification performance of Pt—Au NPs, the responses of *E. coli* O157:H7 sample in different concentrations ($10^2$-$10^8$ cells mL$^{-1}$) on Pt—Au based ICA assays were obtained and compared with colloidal gold-based ICA. When *E. coli* O157:H7 was not provided in the sample, neither kind of ICA present any responses in the test zone. There is no colored line shown for colloidal gold-based ICA in the case of $10^5$ cells mL$^{-1}$ *E. coli* O157:H7 (not shown), whereas there is a strongly visible blue line in Pt—Au based ICA with TMB (not shown). There are commercially available test kits such as MaxSignal, RapidChek, Gen-Probe, IQuum, and Watersafe. However, the detection limit ranges from $10^5$ to $10^7$ cells mL$^{-1}$ without an enrichment step and is ~$10^5$ cells mL$^{-1}$ for live *E. coli* O157:H7 (Wang, J. et al., 2006, Wei Sheng Yan Jiu 35, 439-441.). The detection limit of Pt—Au based ICA was significantly lower than that of colloidal gold-based ICA. Visible blue lines were observed at $10^2$ cells mL$^{-1}$ of *E. coli* O157:H7 after adding TMB solution as the signal amplifier (FIG. 5), the intensity enhanced progressively with increasing amount of *E. coli* O157:H7; whereas the colloidal gold-based ICA did not show visible signal until *E. coli* O157:H7 concentration reached to $10^6$ cells mL$^{-1}$ (not shown). The dramatic improvement of detection limit ($10^2$ cells $mL^{-1}$) for the Pt—Au based ICA is due to its high surface to volume ratio and excellent catalytic activity. In addition, Pt—Au NPs was very high the peroxidase activity, the visual detection can be achieved within a 1 min.

Figure 5:
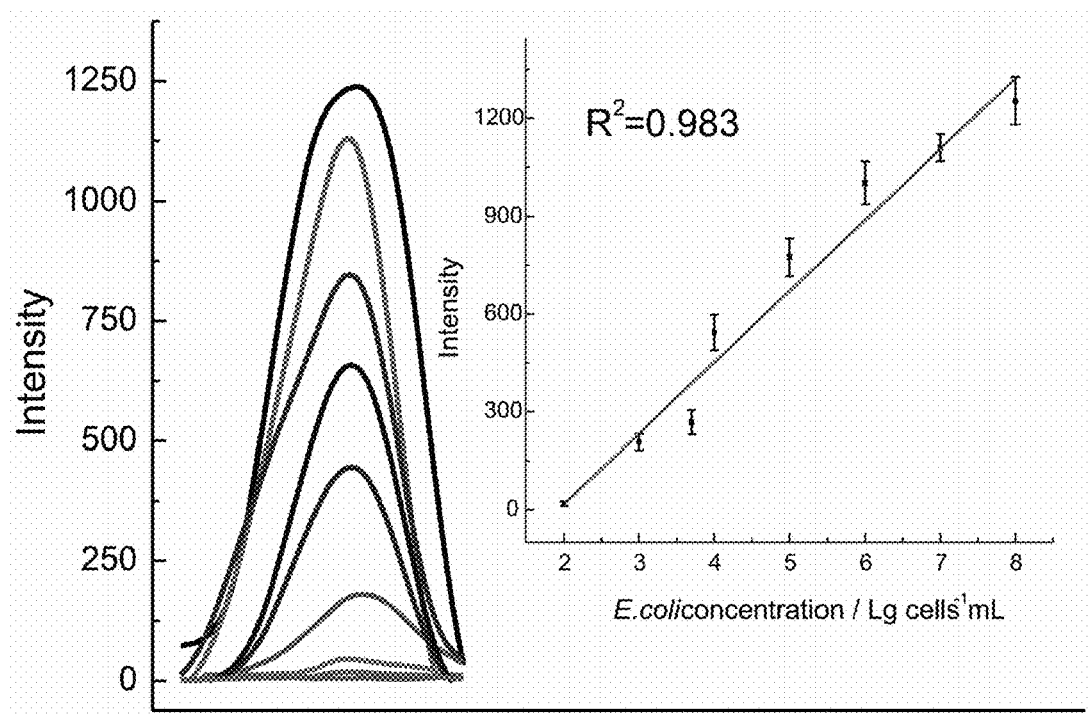
FIG. 5 graphically illustrates the intensity response curves using the Pt—Au based ICA strip reader corresponding to different $E.\ coli$ O157:H7 concentrations after adding TMB. The $E.\ coli$ O157:H7 concentrations used were control, $10^1$ cells $mL^{-1}$, $10^2$ cells $mL^{-1}$, $10^3$ cells $mL^{-1}$, $10^4$ cells $mL^{-1}$, $10^5$ cells $mL^{-1}$, $10^6$ cells $mL^{-1}$, $10^7$ cells $mL^{-1}$, and $10^8$ cells $mL^{-1}$. The inset shows the relationship between the concentration of $E.\ coli$ O157:H7 and the test line intensity. Each point represents the average data value obtained from five independent tests.

Under optimal experimental conditions, portable test strip reader was used to detect the signal of the Pt—Au based ICA. FIG. 5 reflects the optical response recorded by the portable strip reader under different concentrations of *E. coli* O157:H7. No visual test line was observed on the test zone of ICA in the negative control, which revealed a negligible nonspecific adsorption under the optimal experimental conditions. The remarkable blue test lines were seen even at $10^2$ cells $mL^{-1}$, indicating the developed ICA device could serve as a simple visual yes/no determination of *E. coli* O157:H7 without expensive equipment. The peak of intensity or the darkness of the test lines enhanced with the increasing concentration of *E. coli* O157:H7. Furthermore, the peak intensity increased with the increasing concentration of *E. coli* O157:H7. The concentration-peak intensity relationship can be fitted with a log-linear model analysis as shown in the inset of FIG. 5. By employing the approach of test strips reader, the proposed sensing platform will be estimated as a quantifiable and sensitive strategy for detection of *E. coli* O157:H7. Compared with the conventional colloid gold-based *E. coli* O157:H7 ICA, which has a detection limit of $10^6$ cells $mL^{-1}$, the proposed Pt—Au ICA has a lower naked eye detection limit ($10^2$ cells $mL^{-1}$), a broader detection range, rapid detective ability, which can visualize the signal without expensive instruments (TABLE 1).

TABLE 1

The comparison of ICA used for detection of *E. coli* O157:H7.

| | Detection limit (cells $mL^{-1}$) | Refs |
|---|---|---|
| Carboxyl-fluorescent microsphere | $10^4$ | Xie et al., 2014b, 2014b., Biosens. Bioelectron. 54, 262-265 |
| Flower-like Au NPs | $10^5$ | Zhang et al., 2015, Langmuir 27, 13861-13867 |
| Magnetic NPs | $10^5$ | Qi et al., 2011, Int. J. Nanomed. 6, 3033-3039 |
| Colloidal Au NPs | $10^5$ | Jung et al., 2005, J. Food Prot. 68, 2140-2143 |
| Superparamagnetic NPs | $10^4$ | Shi et al., 2015, Anal. Bioanal. Chem. 407, 529-535 |
| Pt—Au NPs | $10^2$ | This work |

3.5 Characterization and Optimization of the Immunoreaction

The signal to noise ratio (S/N) of ICA, which represents the immunoreaction efficiency and detection sensitivity, is affected by several perspectives: the concentration of Pt—Au NPs conjugated on antibody, the concentration of antibody associating with Pt—Au NPs, the pH of the detection condition, and the reaction time. In addition, the economic cost also influences the selection of optimal condition.

The S/N ratio increased up to 20 mg $mL^{-1}$ of Pt—Au NPs conjugated on antibody because of the increasing Pt—Au NPs captured by those antibodies (not shown). After that, the S/N ratio decreased again due to the increasing residual NPs attributing to the increasing background noise (not shown). Hence, 20 mg $mL^{-1}$ of Pt—Au NPs was adopted for all the following experiments.

Up to 13 mg $mL^{-1}$ antibody, the S/N ratio increased as the concentration of antibody increased (not shown). The increasing antibody enhanced the immunoreaction efficiency contributing to the stronger signal. As 13 mg $mL^{-1}$ antibody did not improve the performance significantly comparing with 10 mg $mL^-$ (data not shown), we chose 10 mg $mL^{-1}$ to prepare the Pt—Au based $Ab_1$.

As most NPs-antibody requires a specific pH range for optimal response, the highest S/N ratio was obtained with pH 9-10, so this pH range was adopted as the optimal condition (not shown).

The S/N ratio also changes along with the reaction. The highest ratio was obtained after we added TMB for 10-20 min (not shown). At the beginning, the signal enhanced as times went on because of the increasing oxidation products. Then, the signal intensity flattened, which might be due to the completion of oxidative reaction and also the diffusion blurring signal. To balance, we waited for 10-20 min after adding TMB for all the experiments.

4. Conclusion

We reported a low-cost and sensitive detection method of *E. coli* O157:H7 using signal amplification strategy. The amplification principle is based on the peroxidase-like activity of bimetal NPs toward TMB solution. The measurements were performed by analyzing the color intensity with naked eyes and a portable strips reader. This approach relies on using bimetal NPs as label for reporting antibody. This new technology is a major breakthrough for real-time, sensitive, rapid, qualitative and even quantitative detection of variety of foodborne pathogen or biomarkers in diagnostics. It also has broad impacts on the health diagnostics in developing countries because of the low-cost and easy operation.

Example 2

This Example describes smartphone-based dual-lateral flow immunoassays for simultaneous detection of *Salmonella* and *Escherichia coli* O157:H7 using Pt—Pd nanoparticles for signal amplification.

Abstract: Foodborne pathogens are a major public health threat of global proportions. It is still an incremental challenge to develop sensitive nanoparticle-based assay and portable quantitative device. In this study, we report a dual-lateral flow immunoassays (dual-LFIA) for sensitive detection of *Salmonella* and *Escherichia coli* O157:H7 simultaneously employing Pt—Pd nanoparticles and using smartphone-based device. The described dual-LFIA was able to detect both *Salmonella Enteritidis* and *E. coli* O157:H7 with a detection limit of 10 CFU/mL after systematic optimization. The estimated recoveries of the dual-LFIA range from 91.44% to 109.56%, which indicated the developed method is capable of detecting bacteria in food samples. This study provides a sensitive and portable approach for *Salmonella* and *E. coli* O157:H7 detection in aqueous solutions and real food samples, showing great promise for food analysis or in-field food safety tracking.

1. Introduction

Pathogenic bacterial contamination of food is a major public health threat to countries all around the world. According to Center for Disease Control (CDC), pathogens caused about 112,000 disability adjusted life years (DALYs) annually in the United States. The rates of DALYs were higher in the Middle Eastern and African regions. Among foodborne pathogens, *Salmonella* and *Escherichia coli* O157:H7 are the most common causes of the recent outbreaks and hospitalizations problems that affect millions of people annually. Therefore, the determination of the two pathogens in a single powerful analytical tool would be of a great value to food safety and human health.

The current gold standard for viable bacterial detection is the culture method, which requires a number of serological and biochemical tests and takes several days to confirm a certain bacterium. In order to overcome the obstacles of single-targeting, labor-intensive, time-consuming and information delay, non-culture methods have been developed based on the principles of biometric elements such as nucleic acid and antibody. Nucleic acid-based techniques, the gold standard for dead bacterial detection, could be multiplexed, sensitive and specific but often require expensive instruments and skilled technical staff, which may have limited suitability for developing regions. Alternatively, immunoassays, such as gold nanoparticle (Au NP)-based lateral flow immunoassays (LFIAs), have been developed to address these issues because of their instrument-free, low-cost, easy-operation, and rapid detection. Although promising, their application is greatly limited due to the limit of detection (LOD) of reported Au NP-based LFIAs (TABLE 2). Magnetic beads were used to pre-concentrating cells and improve sensitivity, but it included additional operating procedures and increased assay time. The other limitation is that specific quantitative reader may not be appropriate for the food industry, which deals with high consumer demand and timely epidemic outbreak prevention. Hence, it is still an incremental challenge to develop sensitive nanoparticle-based assay and portable quantitative device.

field of bacteria detection because of the cooperative interactions, resulting in important features including increased surface area, enhanced peroxidase-like catalytic activity, and increased robustness. Our group has demonstrated that a Pt—Pd nanoparticle-based assay for sensitive detection of p53 protein (see Example 3, below). However, a Pt—Pd based catalyst for sensitive detection of bacteria has not been reported.

In addition, to provide a portable and cost-effective platform to sensitively quantify, smartphone-based device can be considered as one of the most attractive candidates for the development of point-of-care (POC) diagnostics platforms. By the end of 2015, the smartphone penetration rate in North America, Europe, and Africa was estimated to be more than 60%, 45%, and 25%, respectively. Moreover, the device can be made with low-cost 3D printing technology and be exploited to perform analysis in-field using simple procedures. Recent reports showed that it is possible to use a smartphone as a detector for a single LFIA, which decrease costs and increase healthcare availability and accessibility. However, dual-LFIA has not yet been implemented using a smartphone-based device.

We therefore developed a smartphone-based dual-LFIA for simultaneous detection of *Salmonella Enteritidis* and *E. coli* O157:H7 using Pt—Pd nanoparticles as signal ampli-

TABLE 2

Summary of reported Au NP-based LFIAs for *Salmonella* and *E. coli* O157:H7 detection

| Target | Limit of Detection (without enrichment) | Quantitative Device | Simultaneous Detection | Reference |
|---|---|---|---|---|
| *E. coli* O157:H7 | $1.8 \times 10^5$ CFU/mL | No | No | Jung. B. Y., et al., 2005. Journal of food protection 68(10), 2140-2143. |
| *E. coli* O157:H7 | $2.3 \times 10^3$ CFU/mL | No | No | Zhao, X., et al., 2010. African Journal of Microbiology Research 4(9), 663-670. |
| *E. coli* O157:H7 | $10^5$ CFU/mL | No | No | Qi, H., et al., 2011. International journal of nanomedicine 6, 3033. |
| *E. coli* O157:H7 | $7.6 \times 10^3$ CFU/mL | No | No | Xi, C., et al., 2013. Chinese Journal of Analytical Chemistry 41(12), 1812-1816. |
| *E. coli* O157:H7 | $1.14 \times 10^3$ CFU/mL | No | No | Chen, M., et al., 2015, Analytica chimica acta 876, 71-76. |
| *E. coli* O157:H7 | $10^6$ CFU/mL | No | Yes (*E. coli* O157:H7 and *Shigella boydii*) | Song, C., et al., 2016. Food Control 59, 345-351. |
| *Salmonella* | $10^4$ and $10^6$ CFU/mL | No | Yes (*S. Typhimurium* and *S. Enteritidis*) | Moongkarndi, P., et al., 2011. Journal of Veterinary Diagnostic Investigation 23(4), 797-801. |
| *Salmonella* | $3 \times 10^2$ CFU/mL (10 h pre-enrichment incubation) | No | No | Shukla, S., et al., 2014. Canadian journal of microbiology 60(6), 399-406. |
| *Salmonella* | $10^4$ CFU/mL | No | No | Singh. J., et al., 2015. Analytical Methods 7(21), 9281-9288. |
| *Salmonella* | $10^3$ CFU/mL | No | No | Wang, W., et al., 2016. Science China Materials 59(8), 665-674. |
| *Salmonella* and *E. coli* O157:H7 | 10 CFU/mL | Yes (smartphone based device) | Yes (*S. Enteritidis* and *E. coli* O157:H7) | This work |

Bimetallic nanoparticles provide an exciting avenue that could significantly improve the sensitivity and lower the LOD of biosensors because they can retain the functional properties of each component and may provide synergistic effects. Platinum-palladium (Pt—Pd) bimetallic nanoparticles are potential candidates as signal amplification in the fier. The system features three main components: 1) dual-LFIA for its ability of simultaneous detection of targets exhibiting attractive features including real-time, easy-to-use and low-cost; 2) Pt—Pd nanoparticles instead of Au NPs as signal amplification for their abilities of improved the sensitivity; and 3) a smartphone-based device for its ability to image, analyze, quantify, report, warn risk, and trace bacterial contamination along the entire food chain.

2. Experimental Section

2.1 Materials

Pluronic F127, Potassium tetrachloroplatinate(II) ($K_2PtCl_4$), Sodium tetrachloropalladate(II) ($Na_2PdCl_4$), hydrochloric acid (HCl), ascorbic acid, potassium carbonate ($K_2CO_3$), acetone, sucrose, horseradish peroxidase (HRP), hydrogen peroxide ($H_2O_2$), 3,3',5,5'-tetramethylbenzidine (TMB), Tween-20, sucrose, phosphate buffered saline (1×PBS, pH 7.4, 0.01 M), and bovine serum albumin (BSA) were purchased from Sigma-Aldrich (St. Louis, Mo., USA). Mouse anti-*Salmonella* monoclonal antibody, mouse anti-*E. coli* O157:H7 monoclonal antibody and goat anti-mouse IgG antibody were obtained from Abcam Inc., (Cambridge, Mass., USA). Goat anti-*Salmonella* polyclonal antibody and goat anti-*E. coli* O157:H7 polyclonal antibody were purchased from KPL Inc. (Gaithersburg, Md., USA). Nitrocellulose membrane, glass fiber, backing cards, and absorbent pad were purchased from Millipore (Billerica, Mass., USA).

2.2 Preparation and Inactivation Bacteria Samples

*Salmonella Enteritidis* PT30 was from American Tissue Culture Collection (ATCC, Manassas, Va.). *E. coli* O157:H7 EDL933 was obtained from the STEC center at Michigan State University. *Listeria innocua* (NRRL B-33197) was obtained from USDA ARS culture collection. *Staphylococcus aureus* (91.48) was a mastitic isolate from cow mastitis case (Roberson, J. R., et al., Journal of Clinical Microbiology 1992, 30. 3217-9). These strains were maintained at −80° C. in Trypticase Soy Broth (Becton, Dickinson and Company, Sparks, Md.) supplied with 0.6% Yeast Extract (Fisher Scientific, Fair Lawn, N.J.) (TSBYE) and 15% (v/v) glycerol. Bacteria were first activated in TSBYE at 37° C. for 8 h statically, then 1:1000 transferred to TSBYE for the second activation at 37° C. statically for additional 14 h. The twice activated culture was washed once with Phosphate Buffered Saline (PBS, pH7.4), re-suspended in sterile PBS. The resulting bacterial suspension was used as live cell in recovery experiment of spiked food samples. For inactivated bacterial cell preparation, the above prepared bacterial suspension was heat-inactivated in boiling water for 30 min followed addition of formalin (J. T. Baker, Phillipsburg, N.J.) to a final concentration of 0.5% (v/v). Inactivated bacterial cells were used to optimize the conditions and evaluate the performance of the developed dual-LFIA.

2.3 Preparation of Pt—Pd Nanoparticles

Pt—Pd nanoparticles were synthesized according to our previous published method with modification (Ataee-Esfahani, H., et al., Angewandte Chemie International Edition 2013, 52, 13611-13615). Briefly, 20 mg of Pluronic F127 was ultrasonically dissolved in aqueous solution containing 1.8 mL of $K_2PtCl_4$ (20 mM), 0.2 ml of $Na_2PdCl_4$ (20 mM) solution and 44 μL of HCl (6 M). The mixture was processed by ultrasonic method for 4 h after adding 2.0 mL of ascorbic acid (100 mM). The final product was centrifuged at 10,000 rpm for 5 min, the resulting pellet was washed with 4 mL of acetone for three times, then re-suspended in 5 mL of water.

2.4 Preparation of Antibody Modified Pt—Pd Nanoparticle Conjugations

Antibody modified Pt—Pd nanoparticle conjugations were prepared by a modified method according to the literature (Jiang, T., et al., ACS Sensors 2016, 1. 717-724, incorporated herein by reference in its entirety). Firstly, the pH of the Pt—Pd nanoparticles solution was adjusted to 8.2-8.5 by adding 0.02 M $K_2CO_3$. Then, 5 μL of mouse anti-*Salmonella* monoclonal antibody (1 mg/mL) or mouse anti-*E. coli* O157:H7 monoclonal antibody (1 mg/mL) was added into the 1 mL of adjusted Pt—Pd nanoparticles solution. After incubation for 60 min at room temperature, 10.0 wt % BSA was added to the mixture followed by 30 min incubation. After that, the mixture was centrifuged at 10,000 rpm for 20 min and washed with 1×PBS containing 1% BSA twice. Finally, the prepared antibody modified Pt—Pd nanoparticle conjugations were collected and suspended in 100 μL of PBS buffer containing 2% BSA and 3% sucrose.

2.5 Preparation of Dual-Lateral Flow Immunoassays

Figure 6A:
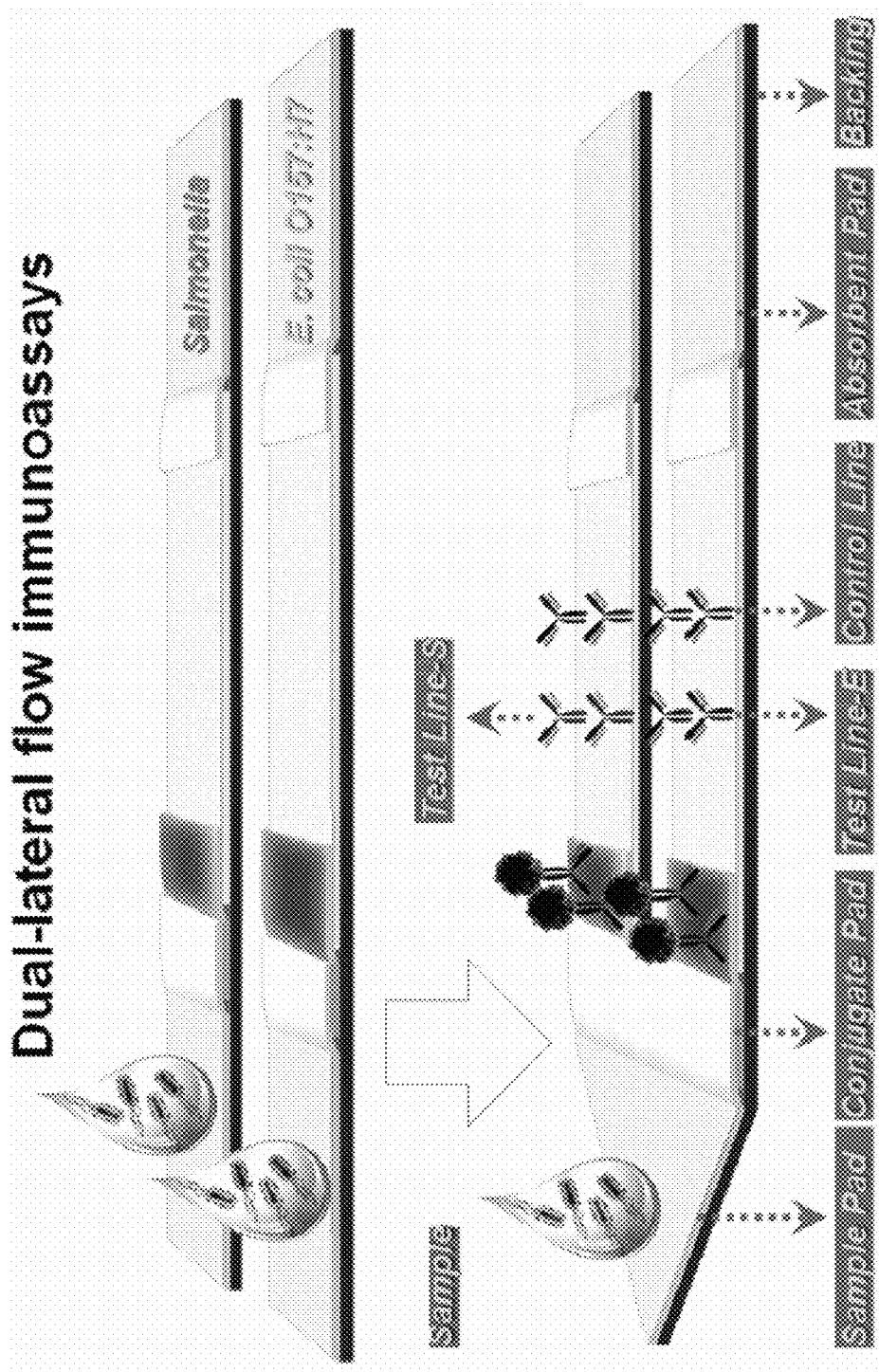
FIGS. 6A-6C are schematic illustrations of smartphone-based dual-lateral flow immunoassays for simultaneous detection of $Salmonella$ and $E.\ coli$ O157:H7 using Pt—Pd nanoparticles as signal amplification.

The dual-LFIA was consisted of a triangle-shape sample pad, two conjugate pads, two nitrocellulose membranes, two absorbent pads and an interoperable backing (FIG. 6A). The sample pad was made from glass fiber and saturated with 1×PBS containing 1% BSA and 0.25% Tween-20, then dried overnight at room temperature. Two test lines (S and E) and two control lines were prepared by dispensing goat anti-*Salmonella* polyclonal antibody (or goat anti-*E. coli* O157:H7 polyclonal antibody) solution (1.0 mg/mL) and goat anti-mouse IgG antibody solution (0.5 mg/mL) at different locations on the nitrocellulose membrane using a BioDot BioJet BJQ 3000 dispenser (Irvine, Calif.). The distance between lines was approximately 1 cm. The nitrocellulose membranes were then dried overnight at 37° C. and stored at 4° C. The conjugate pads and absorbent pads were assembled on backing with an overlap approximately 1-2 mm. Single LFIAs were cut at a width of 4 mm using a Bio-Dot Paper Cutter module CM4000 (Irvine, Calif.). Finally, two LFIAs with different test lines (S or E) were assembled together on the triangle-shape sample pad. The assembled dual-LFIA was either used immediately or stored under dry conditions at room temperature for further tests.

2.6 Fabrication of 3D-Printed Smartphone Accessory Device

Figure 6B:
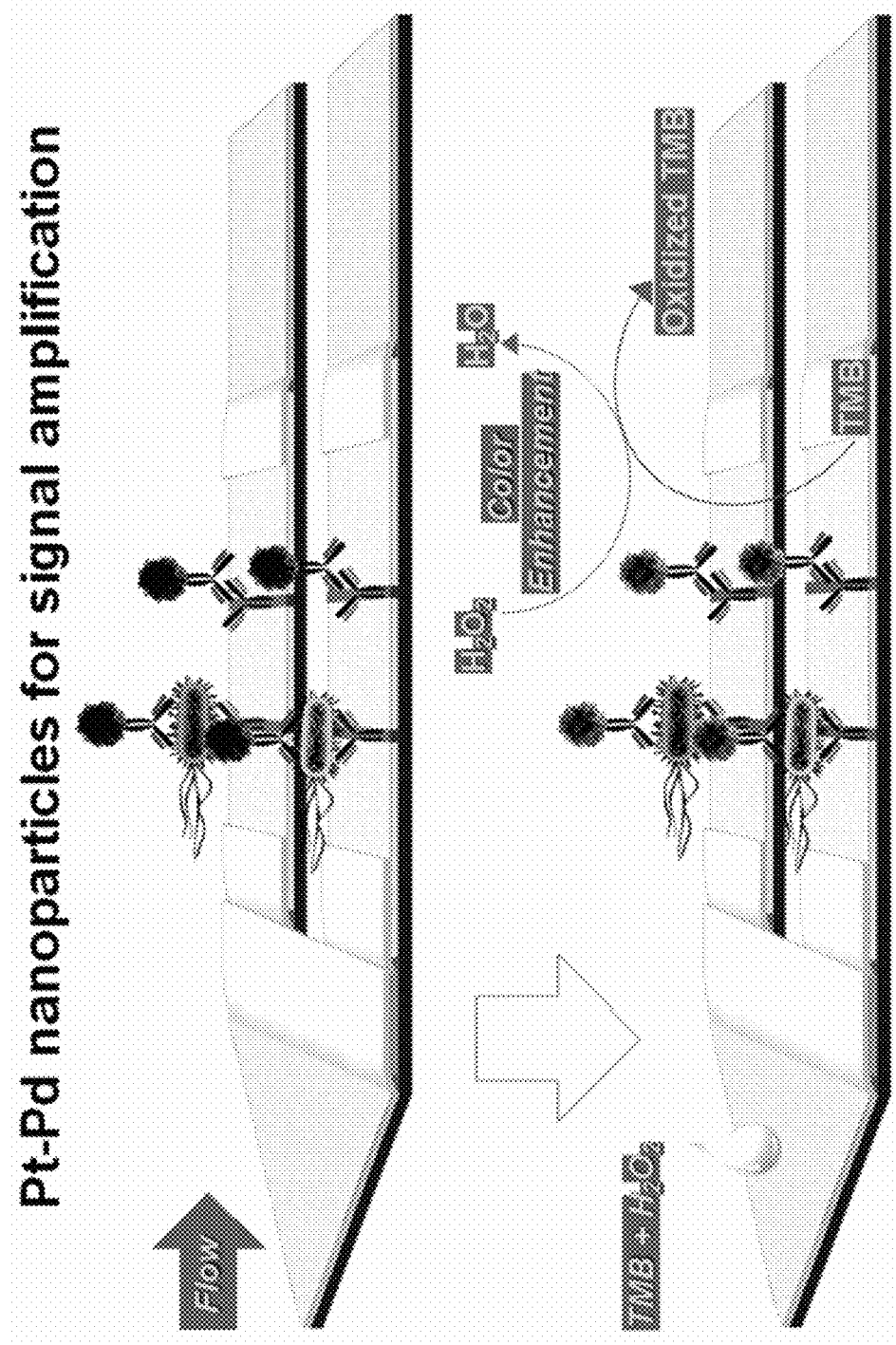
Figure 6C:
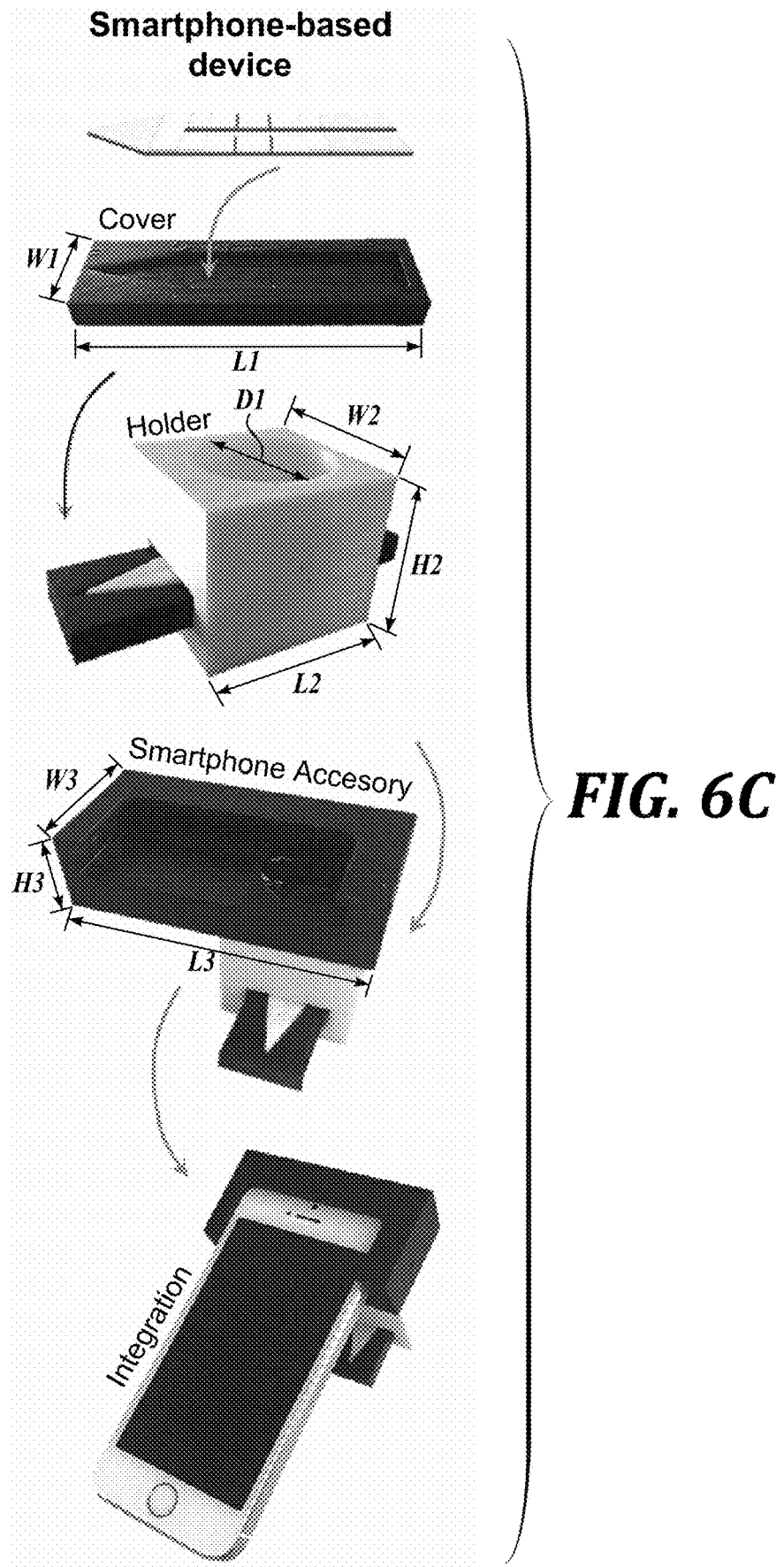

The smartphone accessory was designed with computer-aided design software SolidWorks (Dassault System., MA, USA) based on an Apple iPhone 5s (Apple Inc., CA, USA). The iPhone 5s equipped with a rear iSight 8-megapixel sensor, 1.5 μm pixels and an f/2.2 aperture. A commercial fused filament deposition (FFD) 3D printer (Einstart S, Shining 3D, Hangzhou, Zhejiang, China) was used for the rapid prototyping of the smartphone accessory. A black color polylatic acid (PLA) filament was used for the smartphone holder to minimize light leakage and a white color PLA filament was used to utilize the ambient light for sample illumination (FIG. 6C). A plano convex lens is placed in front of camera to shorten the imaging distance and thus reduce the overall size of the device. The dual-LFIA minicartridge was fabricated by laser cutting and engraving (trotec Speedy 300, Trotect., MI, USA) a Poly(methyl methacrylate) (PMMA) board for consistent and tight fit with the smartphone accessory. The smartphone accessory has a dimension of 73 mm (L), 51 mm (W), and 35 mm (H), and weight a total of 45.9 grams excluding the smartphone and the dual-LFIA cartridge.

2.7 Assay Procedure

In a typical test, a dual-LFIA was preset in the minicartridge. Afterwards, 90 μL of running buffer (1×PBS containing 0.25% Tween-20) was mixed with 10 μL of sample, then loaded to the triangle-like sample pad of dual-LFIA and migrated up due to capillary force. After 1 minute, the black lines appeared visually. After adding 1 μL of TMB solution, the final blue signals were observed on the lines of dual-LFIA within 10 minutes. When *Salmonella* and *E. coli* O157:H7 are present in the sample, they will bind to their own antibody modified Pt—Pd nanoparticle conjugations, and then combine with capture antibodies on the test line-S and test line-E, thereby forming two visible blue lines (see generally the schematic illustrations in FIGS. 6A and 6B). If only *Salmonella* or *E. coli* O157:H7 is present in the sample, only one blue line can be formed. When negative control sample was applied onto the sample pad, no blue line was observed in the test lines. Control line indicated that assay worked properly and the signal at the test line is reliable. Meanwhile, the minicartridge was inserted into the 3D-printed smartphone reader to obtain the results. An iPhone 5S (Apple, USA) with 8 megapixel (8MP) camera was used. The image analysis software, ImageJ, (HIH, MD, USA) can provide graphical readout of the peak area.

2.8 Detection of Artificially Contaminated Milk and Ice Cream Samples

To demonstrate proof-of-concept and its potential application in food samples, milk and ice cream samples were spiked with known number of live bacteria and then detected using the proposed dual-LFIA. 2% low fat milk and double strawberry light ice cream samples were purchased from Walmart supermarket (Pullman, Wash., USA). Only negative samples were selected to be spiked by live bacteria. 10 mL/g of milk and ice cream were added to 90 mL of sterile PBS and from which we prepared samples in the final concentrations of bacterial at $1 \times 10^4$ and $1 \times 10^5$ CFU/ml. Then the spiked samples were evaluated using the same above mentioned condition and the recovery (%) of bacteria from milk and ice cream samples was obtained according to the above calibration curve results.

3. Results and Discussion 3.1 Principle

To achieve double capacity of lateral flow immunoassays, we banded single-plexes together in parallel instead of adding two test lines in a single LFIA (FIG. 6A). The design of such dual-detection systems was based on careful consideration of cross-reactivity and the limitation of Washburn's theory. The proposed dual-LFIAs could provide the same sensitivity of multiplexed detection as individual single LFIA detection. To further improve the sensitivity of the dual-LFIA, we employed Pt—Pd nanoparticles instead of AuNPs as signal amplification (FIG. 6B). The Pt—Pd nanoparticles modified by antibodies owned double functions: recognition and signal amplification. Owing to the intrinsic peroxidase-like catalytic activity, the antibody modified Pt—Pt nanoparticle conjugations can generate stronger blue color in the present of TMB and $H_2O_2$. The enhancement of signals on the two test lines is critical for the detection of low level of pathogens. To provide a field-portable, cost-effective platform with high sensitivity, smartphone-based device was developed to image. The device consists of three parts: 3D printed cover, holder and smartphone accessory, resulting in an integrated tool (FIG. 6C). Exemplary dimensions can be (but are not limited to): W1=about 20 mm; D1=about 28 mm; W2=about 35 mm; H2=about 30 mm; L2=about 35 mm; W3=about 35 mm; H3=about 20 mm; and L3=about 73 mm. Together, the proposed assay is portable and sensitive without any complex sample pre-enrichment and specialized instruments, making it a valuable detection tool for foodborne pathogen.

3.2 Characterization 3.2.1 Construction

Figure 7A:
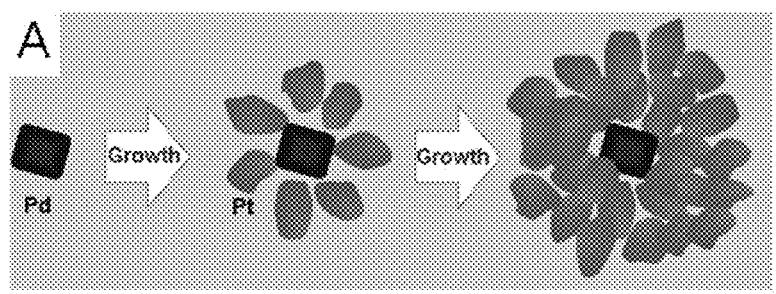
FIGS. 7A-7G illustrate the construction of Pt—Pd nanoparticles.
Figure 7B:
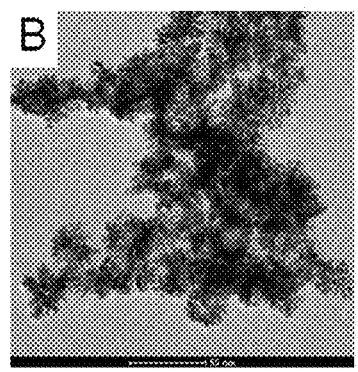
Figure 7C:
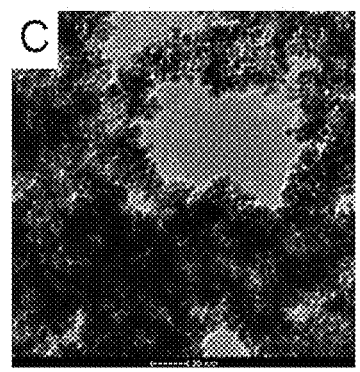
Figure 7D:
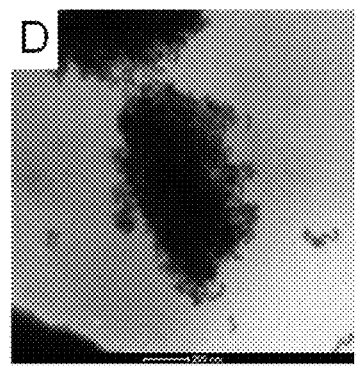
Figure 7E:
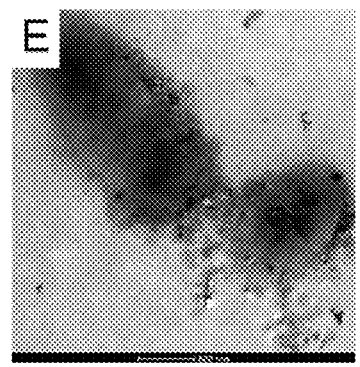
Figure 7F:
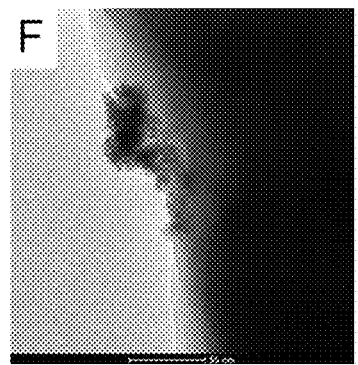
Figure 7G:
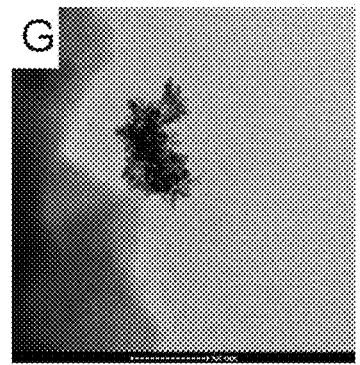

To investigate the morphology of Pt—Pd nanoparticles before and after antibody modification, transmission electron microscope (TEM) images were collected. As shown in FIGS. 7A and 7B, the crystal growth was happened on the surface of Pd nanocrystals and on tips of the active branches (Wu, H., et al., Nanotechnology 2014, 25. 195702), and the as-synthesized Pt—Pd nanoparticle size was approximately 35 nm. After antibody modification, TEM image (FIG. 7C) showed a bright circle around Pt—Pd nanoparticles, which indicated the functionalization of antibody.

3.2.2 Function

The function of antibody modified Pt—Pt nanoparticle conjugation is a critical factor for dual-LFIA. Antibody modified Pt—Pt nanoparticle conjugation is composed of two parts: anti-*Salmonella* antibodies (or anti-*E. coli* O157:H7 antibodies) with recognition function and Pt—Pt nanoparticles with catalytic activity. First, we test whether the proposed antibodies could recognize *Salmonella* and *E. coli* O157:H7. As shown in FIGS. 7D-7G, TEM images confirmed that *Salmonella* and *E. coli* O157:H7 could be captured by antibody conjugated Pt—Pt nanoparticles. Then, we used antibody conjugated Pt—Pt nanoparticles to catalyze the oxidation of TMB. The results demonstrated that the antibody modified Pt—Pt nanoparticle conjugation had similar catalytic activity with the solution of HRP and unmodified Pt—Pt nanoparticles (not shown). Together, these results indicated that antibody conjugated Pt—Pt nanoparticles possessed the dual functions (capturing bacteria and catalytic activity).

3.3 Optimization

Figure 8A:
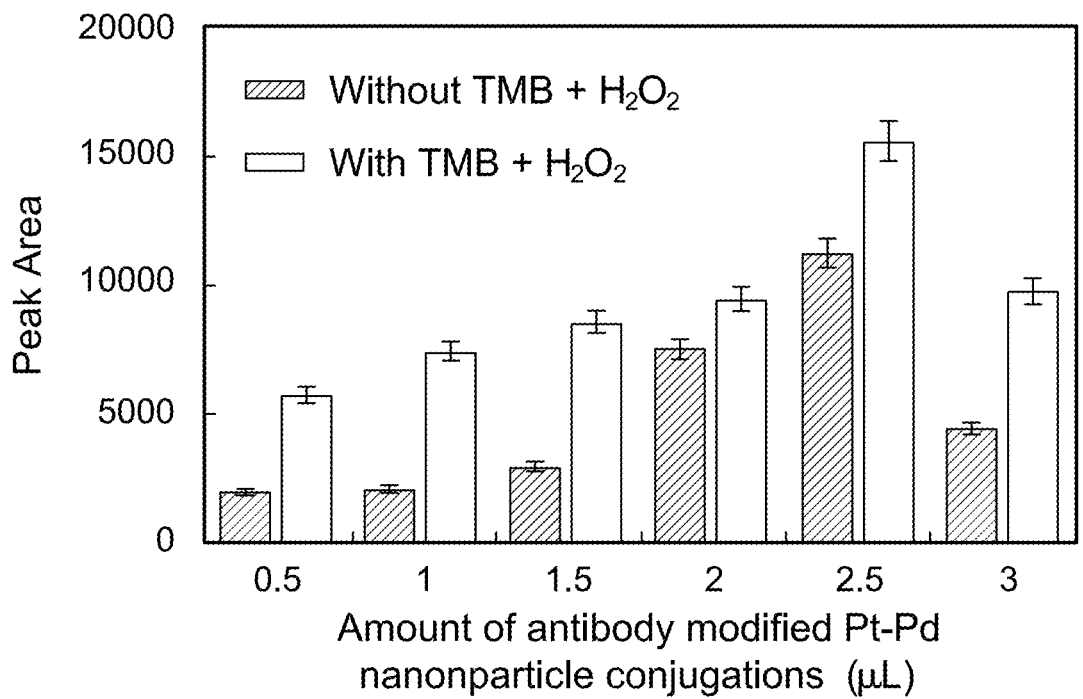
FIGS. 8A-8D illustrate assay optimization with respect to peak area of test lines with or without TMB and $H_2O_2$.
Figure 8B:
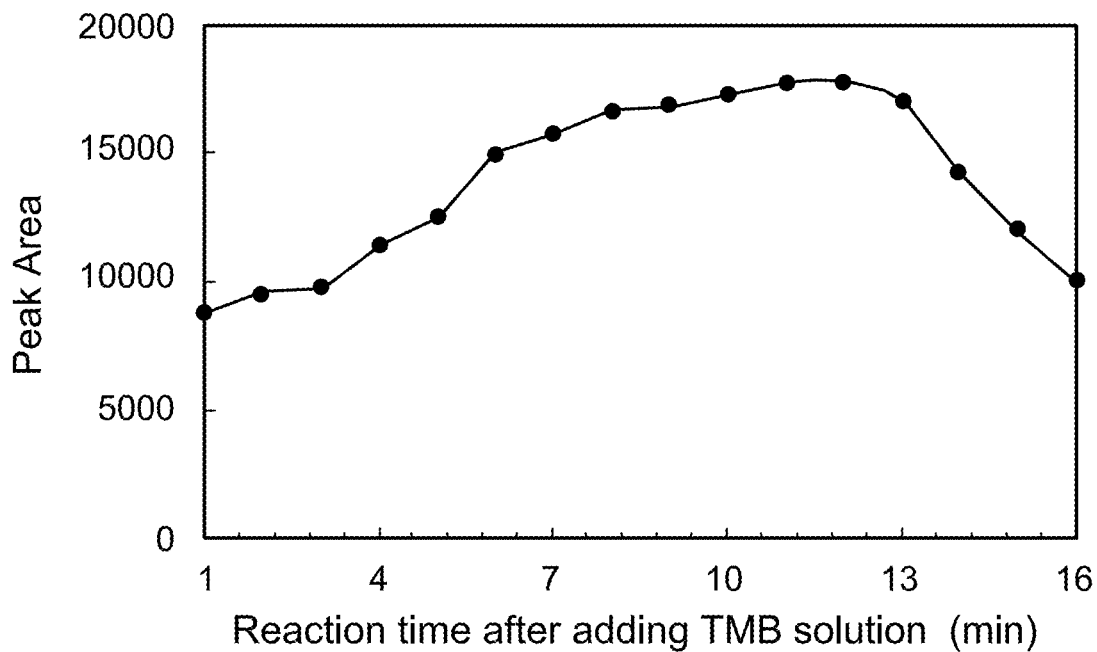
Figure 8C:
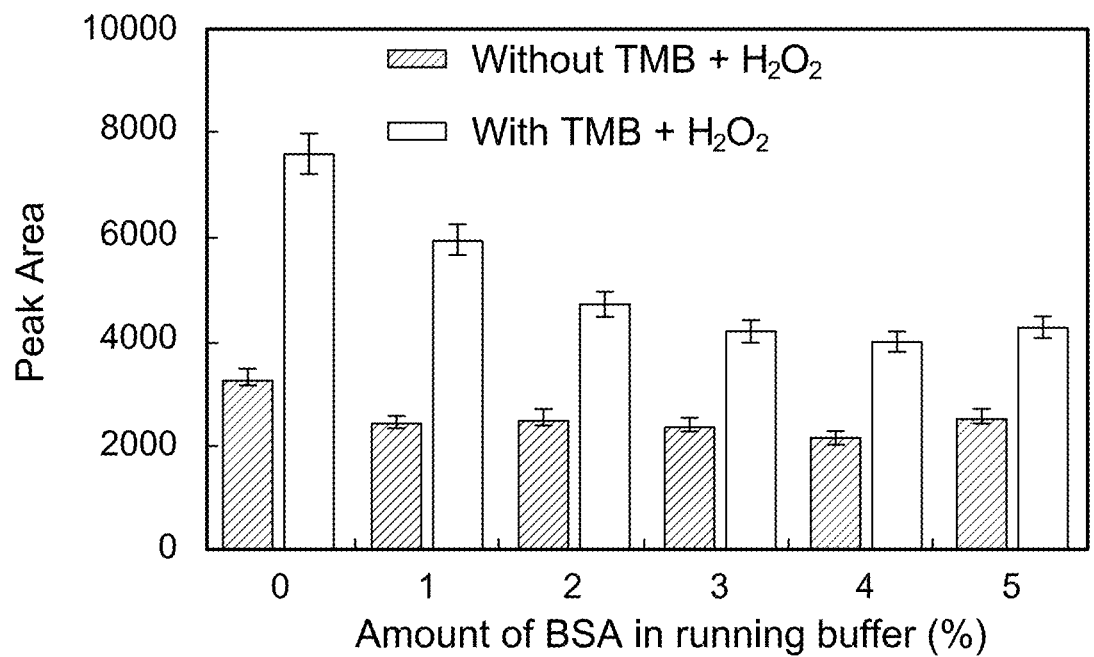
Figure 8D:
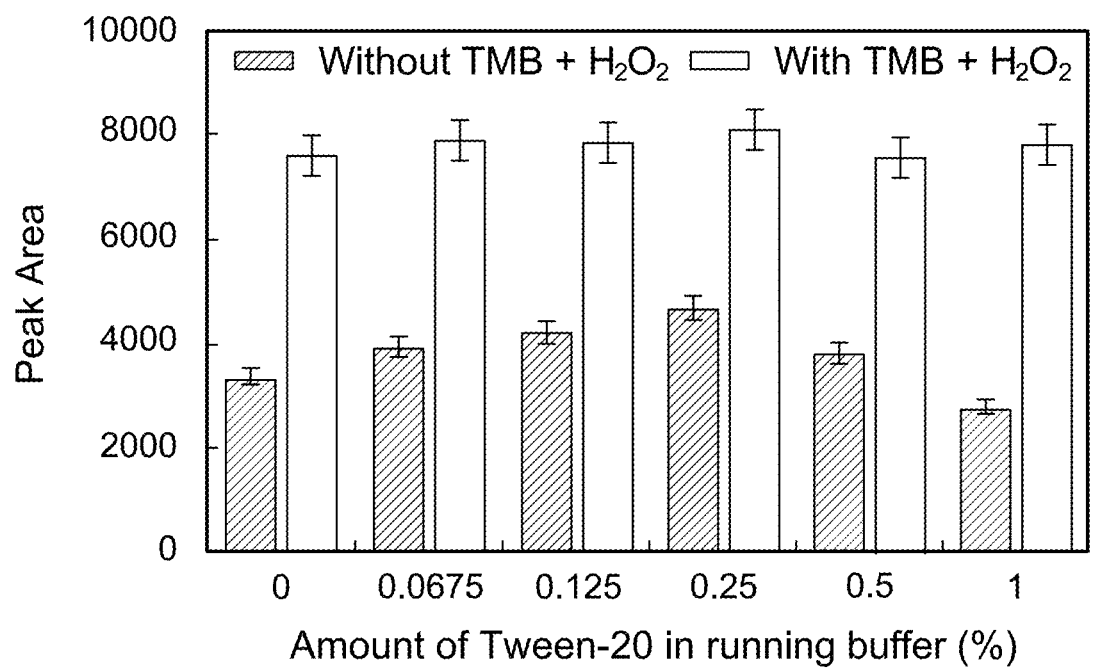

To achieve the best performance of the dual-LFIA, the reaction system was first optimized. The amount of antibody modified Pt—Pd nanoparticle conjugations on the conjugate pad could affect the hybridization efficiency between bacteria and corresponding antibody, and thus the performance of dual-LFIA. As seen from FIG. 8A, the peak area increased up to 2.5 µL, then decreased at 3.0 µL. The peak area loss at a high concentration probably due to stereo hindrance between bacteria and antibody modified Pt—Pd nanoparticle conjugations. Therefore, 2.5 µL of antibody modified Pt—Pd nanoparticle conjugations was the optimal amount, and was used in the further experiments. FIG. 8B shows the results for the time after adding TMB solution. The peak area increased as the reaction time increased until 12 min, and decreased as the reaction time increased after 12 min. No significant difference was observed in the peak area for assays between the reaction time of 8 to 12 min. A hybridization time of 10 min was selected for all subsequent tests. Running buffer also plays an important role, as it can minimize nonspecific adsorption and increase the sensitivity of the dual-LFIA. As shown in FIG. 8C, with increasing BSA, the corresponding response decreased significantly, especially when adding TMB solution. BSA-free 1×PBS was found to be the optimal running buffer, while 1% of BSA was added in the solution to prepare sample pad. FIG. 8D presents the responses remained almost the same with varying amount of Tween-20 in running buffer with TMB solution. However, in the condition of signal without TMB enhancement, the best result was obtained with 0.25% Tween-20, which was used as the optimal running buffer in subsequent detections.

3.4 Sensitivity

Figure 9A:
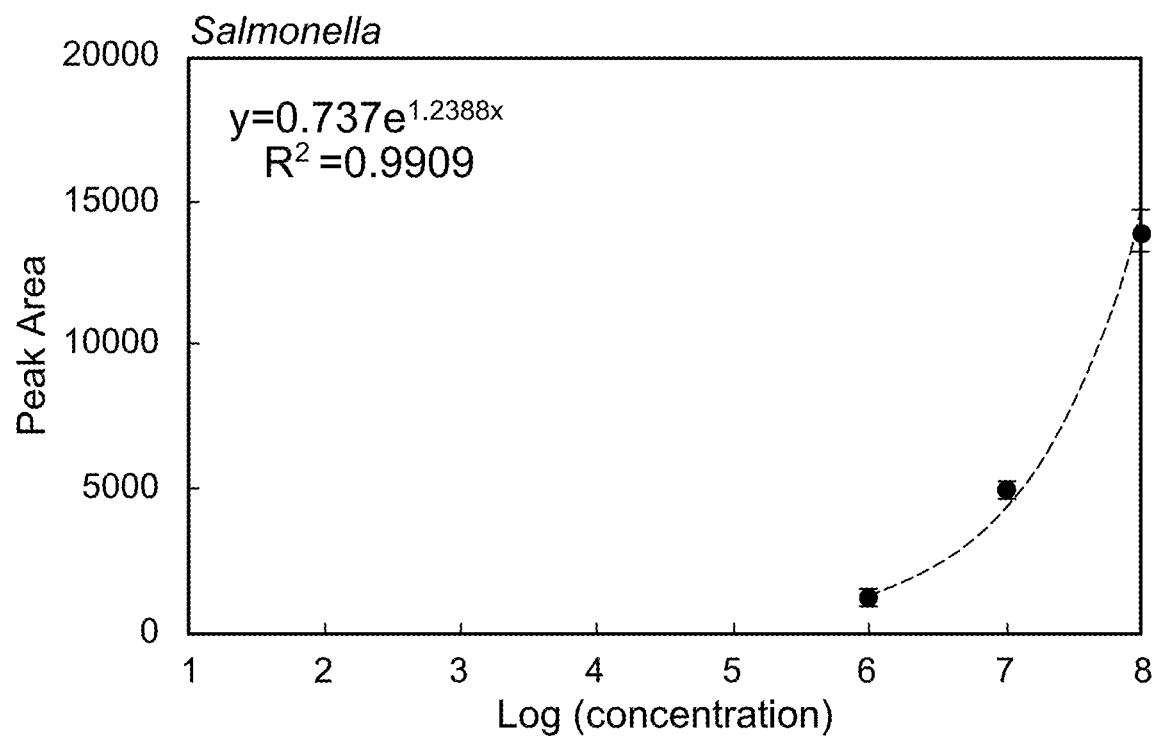
FIGS. 9A-9D graphically illustrate the sensitivity of dual-LFIA for simultaneous detection of $Salmonella$ and $E.\ coli$ O157:H7.
Figure 9B:
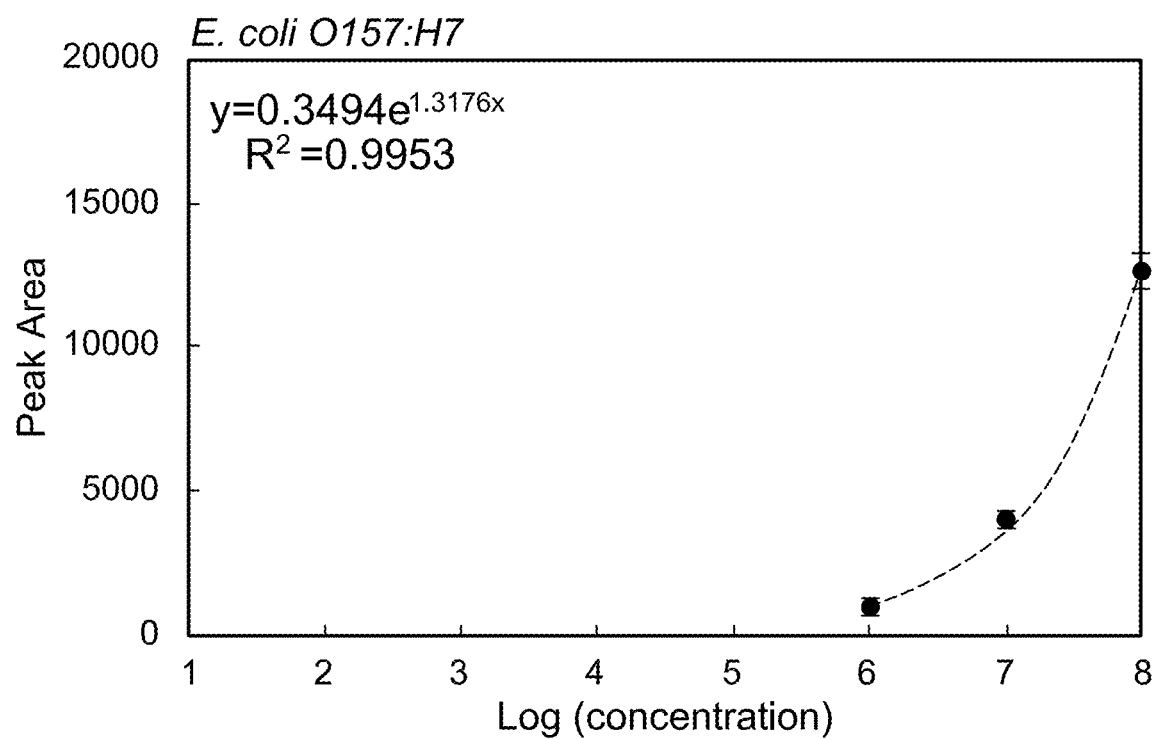
Figure 9C:
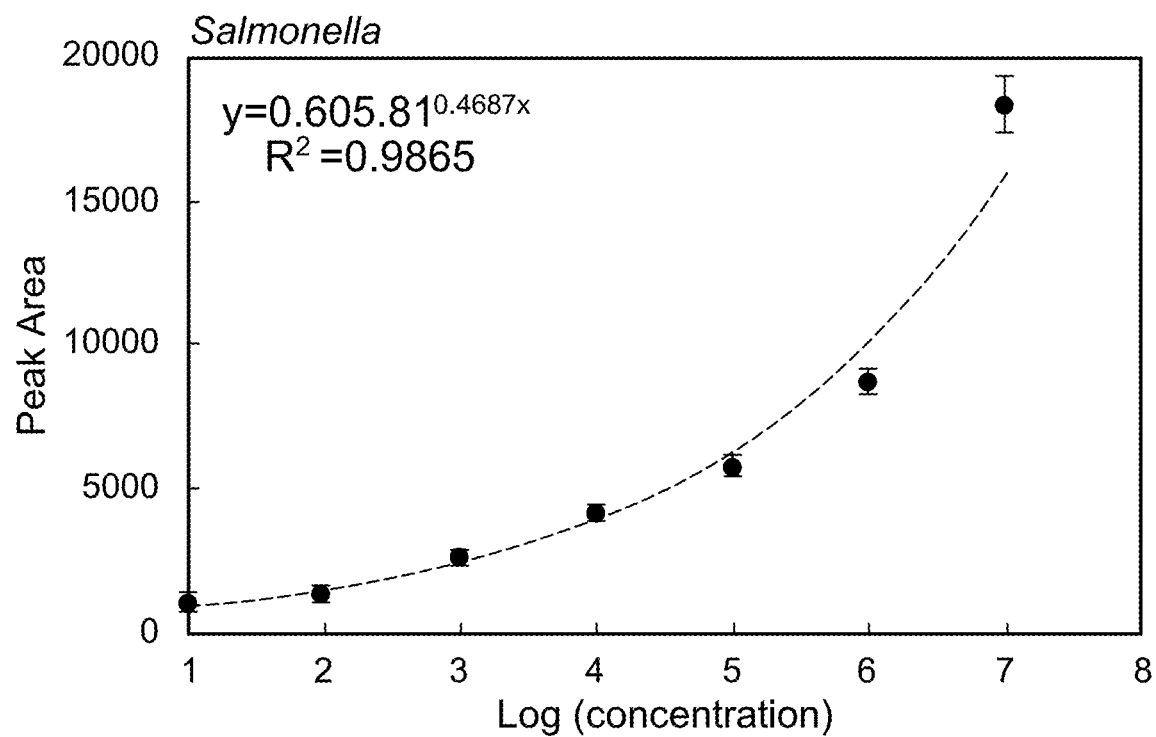
Figure 9D:
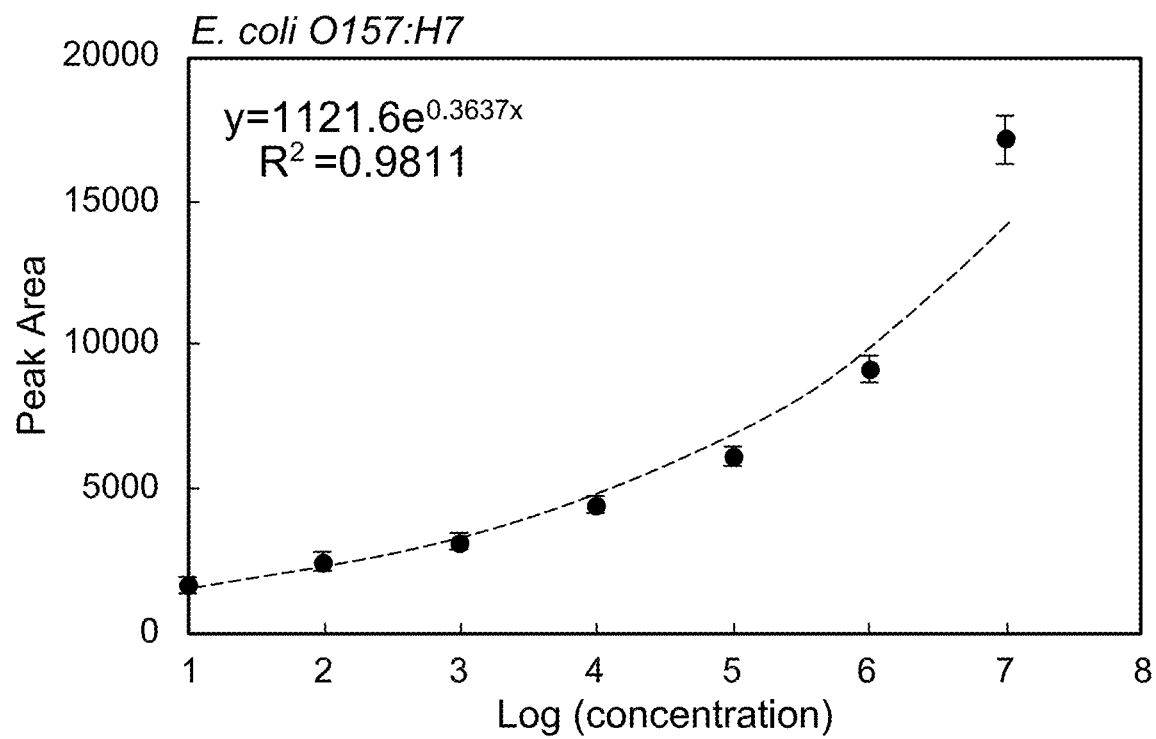

The sensitivities of optimized dual-LFIA were further estimated using sample solutions containing various concentrations of targets under the optimized experimental conditions. Photo image of the dual-LFIAs with different bacterial concentrations ranging from 0 to $10^8$ CFU/mL were taken. The detection limit of *Salmonella* and *E. coli* O157:H7 without TMB and $H_2O_2$ were both approximately $10^6$ CFU/mL (FIGS. 9A and 9B), which was dramatically improved after adding TMB and $H_2O_2$ (FIGS. 9C and 9D). The blue band in the dual-LFIA test zone was observed with as low as 10 CFU/mL of *Salmonella* and *E. coli* O157:H7 without any pre-enrichment, which was 1000-fold more sensitive than previously published AuNP-based LFIAs (TABLE 2). Quantitative detection was performed by recording the peak areas of two test lines (S and E). The resulting calibration curves were exponential for both pathogens over the 10-10$^7$ CFU/mL range (FIGS. 9C and 9D). These results well demonstrate the sensitive performance of our assay for simultaneous detection of two pathogens, which contributed by the peroxidase-like catalytic activity of the Pt—Pd nanoparticles for signal enhancement and the parallel design of dual-detection for noninterference.

3.5 Specificity

Figure 10:
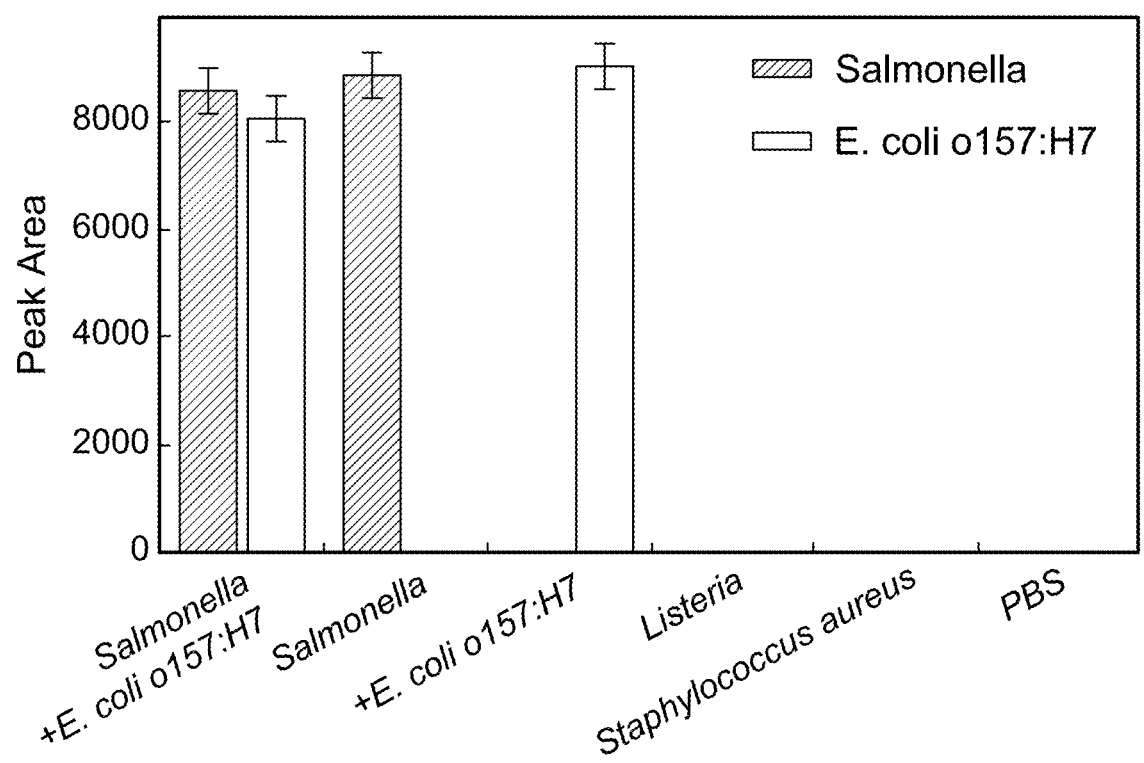
FIG. 10 graphically illustrates the specificity of dual-LFIA for detection of the corresponding sample solution. Typical photo image of dual-LFIAs were taken for detection of different samples: a mixture of $10^6$ CFU/mL $Salmonella$ and $10^6$ CFU/mL $E.\ coli$ O157:H7, $10^6$ CFU/mL $Salmonella$, $10^6$ CFU/mL $E.\ coli$ O157:H7, $10^8$ CFU/mL $Listeria$, $10^8$ CFU/mL $Staphylococcus\ aureus$, and 1×PBS. Shown is a histogram with respect to peak area of test lines (S and E) via different samples. Error bars indicate standard deviations of three measurements.

The specificity of dual-LFIA was further evaluated with other bacteria and PBS. We detected a mixture of 10$^6$ CFU/mL *Salmonella* and 10$^6$ CFU/mL *E. coli* O157:H7, as well as 10$^6$ CFU/mL *Salmonella*, 10$^6$ CFU/mL *E. coli* O157:H7, 10$^8$ CFU/mL *Listeria* and 10$^8$ CFU/mL *Staphylococcus aureus* by dual-LFIAs. No distinct blue band was observed on the test lines of dual-LFIAs in the samples absence of corresponding bacteria as expected (FIG. 10). No cross-reactivity with other bacteria was confirmed by *Listeria innocua* and *Staphylococcus aureus* (FIG. 10). In addition, no signal was observed in the PBS control test, indicating negligible nonspecific adsorption of the optimized dual-LFIA.

3.6 Detection of Artificially Contaminated Milk and Ice Cream Samples

To demonstrate potential application of the dual-LFIA in food samples, the device was used to detect *Salmonella* and *E. coli* O157:H7 spiked at milk or ice cream samples. The estimated recoveries of the dual-LFIA range from 91.44% to 109.56% (TABLE 3), which clearly indicated the developed method is capable of detecting bacteria in food samples. In addition, the spike and recovery experiment using live pathogens further confirmed the usability for both viable and dead bacteria detection of the dual-LFIA.

integration is expected to further simplify the assay to make it more suitable for on-site applications by a wide range of users.

Example 3

This Example describes the detection of p53 protein based on mesoporous Pt—Pd nanoparticles with enhanced peroxidase-like catalysis Abstract: this study describes a sensitive immunochromato-graphic test strip based on mesoporous Pt—Pd bimetal nanoparticles (NPs) with greatly enhanced peroxidase-like catalysis for detection of p53 visually and quantitatively. The principle of this assay is relied on the measurements of visual color intensity produced by peroxidase reaction with 3,3',5,5'-tetramethylbenzidine (TMB) solution. Owing to the strong peroxidase-like activity of Pt—Pd NPs, it exhibited strong visual color in less than 30 s in low concentration range of target analytes. Quantitative measurement of p53 was performed with a hand-held test strip reader, which yields a detection limit of 0.05 ng mL$^{-1}$ with the linear range of 0.1-10 ng mL$^{-1}$. Although the feasibility was demonstrated using p53 as a model analyte, this approach could be easily extended for detection of other protein biomarkers.

1. Introduction

Quantitative and sensitive detection of protein biomarkers holds great promise for various disease diagnostics. Varieties of current biomarker detection methods are based on enzyme-linked immunosorbent assays (ELISA), such as magnetic bead based assay and electrochemical and electrochemiluminescent immunosensors. Generally, these immunoassay based methods are time- and labor-consuming and not suitable for point-of-care applications. As one of the promising strategies for point-of-care diagnostics, immunochromatographic test strip (ITS) outweighs other assays

TABLE 3

Recovery experiments of dual-LFIA for detection of *Salmonella* and *E. coli* O157:H7 spiked in milk and ice cream.

| | Detected (CFU/mL) | | Added (CFU/mL) | | Found (CFU/mL) | | Recovery (%) | |
|---|---|---|---|---|---|---|---|---|
| Sample | *Salmonella* | *E. coli* O157:H7 | *Salmonella* | *E. coli* O157:H7 | *Salmonella* | *E. coli* O157:H7 | *Salmonella* | *E. coli* O157:H7 |
| Milk | 0 | 0 | 1 × 10$^4$ | 1 × 10$^4$ | 10664 | 10396 | 106.64 | 103.96 |
| Milk | 0 | 0 | 1 × 10$^5$ | 1 × 10$^5$ | 107468 | 91438 | 107.47 | 91.44 |
| Ice cream | 0 | 0 | 1 × 10$^4$ | 1 × 10$^4$ | 10817 | 10718 | 108.17 | 107.18 |
| Ice cream | 0 | 0 | 1 × 10$^5$ | 1 × 10$^5$ | 93253 | 109562 | 93.25 | 109.56 |

4. Conclusions

In summary, this is the first report of quantitative dual-LFIA for simultaneously detecting two pathogens employing Pt—Pd nanoparticles and a smartphone-based device. By using Pt—Pd nanoparticles for signal enhancement and the parallel design of dual-detection, we could detect *S. Enteritidis* and *E. coli* O157:H7 with a limit of detection of 10 CFU/mL. The estimated recoveries of the dual-LFIA range from 91.44% to 109.56%, which indicated the developed method is capable of detecting bacteria in food samples. Compared with conventional AuNP-based LFIAs, the current approach is much more sensitive and portable, avoiding the use of complex sample pre-enrichment and specialized instruments. Although the current format requires loading of TMB solutions during the experiment, this process can be further simplified by sealing them in blister packs and bursting them open prior to use. Such because of its easy operation, low cost, and rapidness, and has been widely studied in various applications including pregnancy tests as well as pathogen and cancer biomarker detection.

Colloidal gold nanoparticles often serve as signal label of ITS for detection of varieties of analytes due to its unique optical properties and remarkable physical-chemical stability. Many gold-based ITS have been applied for qualitative and semiquantitative detection of protein biomarkers. In addition, significant attempts still need to be made to improve the sensitivity of ITS by introducing various labels including quantum dots, colored latex particles, and upconverting phosphors. These nanomaterials exhibit higher sensitivity and broader response range than colloidal gold based conventional ITS. Nonetheless, the increased sensitivity of these nanomaterials generates several drawbacks. Their chemical instability, short lifetime, expensive instrument requirements, and long handling time limit them from applications in conventional point-of-care diagnosis.

With the high surface area and rapid ion-transport feature, noble bimetallic nanoparticles (NPs) have provided excellent catalytic performance. For instance, Pt-bimetallic NPs have been intensively studied in biomedical field due to their unique biocompatibility. They have unique advantages including high catalytic activity for determination of glucose at low potentials, excellent temperature controlled catalytic behaviors, and better thermostability than enzymes, which require appropriate conditions to maintain three dimensional structures for the functionality. These specific characteristics offer promising application in fabricating ITS. However, there are very few examples of integrating Pt-based bimetallic NPs into point-of-care analytical systems for signal amplification.

Herein, we report a mesoporous Pt—Pd NPs based ITS for easy-operation and rapid and sensitive detection of protein biomarkers. The greatly improved sensitivity resulted from the amplification of peroxidase-like activity of Pt—Pd NPs. 3,3',5,5'-Tetramethylbenzidine (TMB), a chromogenic reagent, serving as a good signal amplifier, provides extremely high visual sensitivity compared to other classic substrates. See, e.g., Mesulam, M. M., J. Histochem. Cytochem. 1978, 26, 106-117. The p53 protein, a well-known cellular tumor protein which plays an important role in multiple central cellular processes and associates with the diagnostics of more than 40% of human cancers, was used as a model analyte for the ITS; the detection limit is 0.05 ng mL$^{-1}$, and was about 1/2000 of that of the recent commercial gold nanoparticles based ITS. This new signal amplification protocol based on peroxidase-like catalysis of Pt—Pd NPs provides a reliable, rapid, and sensitive strategy for visual detection and quantitative analysis of a broad range of protein biomarkers.

2. Experimental Section 2.1 Materials and Reagents

Pluronic F127, K$_2$PtCl$_4$ (Pt, 44.99%), Na$_2$PdCl$_4$ (Pd, 49.98%), 3,3',5,5'-tetramethylbenzidine (TMB), ophenylenediamine (oPD), commercial Pt carbon nanopowder, hydrochloric acid (HCl, 39%), sodium hydroxide (NaOH), and ascorbic acid (AA) were purchased from Sigma-Aldrich. Fetal bovine serum (FBS) and bovine serum albumin (BSA) were purchased from ATCC. Rabbit anti-p53 polyclonal antibody, mouse anti-p53 monoclonal antibody, and goat anti-rabbit antibody were obtained from Kirkegaard & Perry Laboratories Inc. (Baltimore, Mass.). Nitrocellulose membrane, fiber sample pad, fiber conjugate pad, laminated cards, and absorbent pad were provided by Millipore (Billerica, Mass.). Ultrapure water from a Millipore Milli-Q water purification system was used for experiments. The phosphate buffered saline (PBS) containing Na$_2$HPO$_4$ and Na$_2$HPO$_4$ was prepared using deionized water (18.2 MΩ-cm), and the pH was adjusted with NaOH and H$_3$PO$_4$. All the reagents are analytical standard and used without further purification. The real samples analyzed in our experiments were human serum of cases of gastric cancer (GC), chronic atrophic gastritis (CAG), and chronic superficial gastritis (CSG) from a local hospital of Lanzhou, P. R. China.

2.2 Preparation of Mesoporous Pt—Pd NPs

Pt—Pd was synthesized by a modified procedure from the work of Yamauchi et al (Ataee-Esfahani, H., and Yamauchi, Y., Angew. Chem. Int. Ed. 2013, 52, 13611-13615). Briefly, Pluronic F127 (10 mg) was ultrasonically dissolved in aqueous solution containing 0.9 mL of K$_2$PtCl$_4$ (20 mM), 0.1 mL of Na$_2$PdCl$_4$ (20 mM) solution, and 22 μL of hydrochloric acid (6 M). After adding 1.0 mL of AA (100 mM) as a reducing agent, the mixture was continuously ultrasonic heated in a 30° C. water bath for 5 h. The final product was collected and rinsed with acetone and water in consecutive washing/centrifugation cycles five times and then dried at room temperature.

2.3 Colorimetric Catalysis of Peroxidase Activity

The colorimetric catalysis experiments were performed to test the peroxidase-like activity among different catalysis. Typically, the organic peroxidase substrates (20 mM) of TMB and oPD were catalytically oxidized by mixing with 5.0 mM H$_2$O$_2$ and using the 5 μg mL$^{-1}$ Pt—Pd NPs suspension to produce different colors of reaction products. In addition, the dynamic parameters of Pt—Pd NPs were measured to obtain Michaelis-Menten curves for different concentrations of TMB or H$_2$O$_2$.

2.4 Preparation of Pt—Pd-Labeled Antibody (Ab$_1$)

The pH of the Pt—Pd NPs solution was adjusted by addition of 0.02 M K$_2$CO$_3$ before adding anti-p53 rabbit polyantibody as labeled antibody. Desired weight of labeled antibody was mixed with desired amount of Pt—Pd NPs, followed by gentle shaking for 1 h at room temperature. Then, 10.0 wt % BSA was added, and the mixture was incubated for 30 min. The mixture was further washed with PBS (1% BSA) and centrifuged at 8,000 rpm for 10 min to remove the washing liquid. Finally, the prepared Pt—Pd-labeled antibody conjugates were collected and suspended in eluent buffer (pH 8.5 containing 10 mM PBS, 0.25% Tween-20, 5% BSA). The total volume of solution after dissolving equals one-tenth of the volume of the pervious solution of Pt—Pd labeled antibody conjugates.

2.5 Preparation of Test Strips

The test strip consists of a sample pad, conjugate pad, reaction membrane, absorbent pad, and backing card. The sample pad was pretreated with blocking buffer (pH 8.5, containing 10 mM PBS, 0.1% (w/v) Tween-20, and 1% (w/v) PVP) and dried at 37° C. for 2 h. Pt—Pd-antibody conjugates were dispensed onto the conjugated pad and dried at 37° C. for 2 h. The desired volume of anti-p53 monoclonal antibody solution (1 mg mL$^{-1}$, Ab$_2$), goat anti-rabbit antibody (0.5 mg mL$^{-1}$) was dispensed on the reaction membrane to form the test line and control line. After 2 h of drying at 37° C., all of the parts mentioned above were assembled on a plastic adhesive backing card, which was cut into 4 mm strips and stored at room temperature.

2.6 Assay Procedure

The assay procedure was as follows: 50 μL of the sample solution was dropped onto the sample pad and flew through the membrane under capillary action, which enabled the reaction with Ab$_1$-labeled Pt—Pd NPs to form complex at conjugation pad. The yielded complex then passed along the nitrocellulose membrane by capillary action until reach the Ab$_2$ in the test line to complete sandwich immunoreaction. The excess complexes could pass through the membrane and captured at the control zone. After adding TMB, the final signal intensity on test line was observed and quantified using a test strip reader.

2.7 Detection of Real Sample

About 50 μL of anti-human p53 monoclonal antibody stock solution was added into a 96-well microplate and incubated at 4° C. overnight with gentle shaking. After the solution was removed, the wells were rinsed three times with washing buffer (0.05% (v/v) Tween-20 in 0.01 M PBS) following by the addition of 250 μL of blocking buffer (2% (w/v) PEG and 3% (w/v) globulin in 0.01 M PBS), and then were incubated at 37° C. for 2 h with gentle shaking to block the remaining active sites. The plates were then washed following by the addition of 50 μL of real sample into the wells, and then were incubated at 37° C. for 1 h with gentle shaking. The wells were then washed three times, as mentioned above, prior to the addition of 50 μL of antibody conjugates and incubation at 37° C. for 1 h with gentle shaking to obtain the sandwich immunoreactions. The completed microplate was rinsed three times. Finally, the measurement was performed using Tecan Safire2 microplate reader.

2.8 Instruments and Characterization

The Raman spectra were obtained with a Robinson model RBH57OR 90C instrument. The transmission electron microscopy (TEM) images were obtained with a Philips CM200UT instrument. The scan electron microscopy (SEM) images were obtained with a Robinson model RBH57OR instrument. A portable fluorescence strip reader ESE-Quant GOLD was purchased from DCN Inc. (Irvine, Calif.).

3. Results and Discussion 3.1 Characterization of Mesoporous Pt—Pd NPs

Considerable attentions on bimetallic NPs have been aroused due to their superior catalytic activity over monometallic counterparts and intensive use in wide range of electrochemical devices. In addition, porous bimetallic NPs provide strong catalytic activity and abundant surface sites. Two methods are utilized in the synthesis of porous structure bimetallic NPs: lipid crystallic method and high temperature tempting method. However, neither is practical because it is hard to form spontaneously structure in the view of thermodynamics. In our study, we took advantage of solution phase synthesis to generate the self-assembly of surfactants into spherical micelles that can be employed as templates for the synthesis of porous metal NPs. Our bimetallic porous Pt—Pd NPs provide large surface area with abundant activity sites on the concave surface.

Figure 11A:
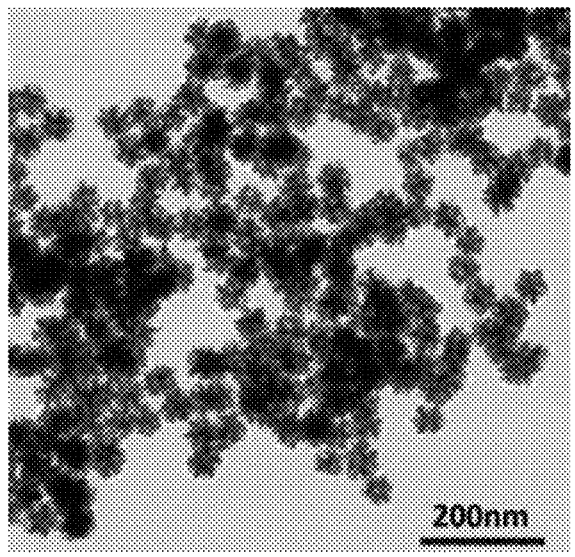
FIGS. 11A-11D are electron micrographs of Pt—Pd NPs.
Figure 11B:
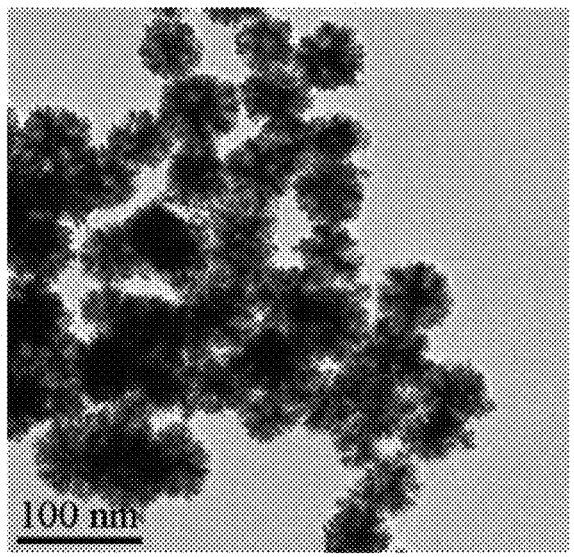
Figure 11C:
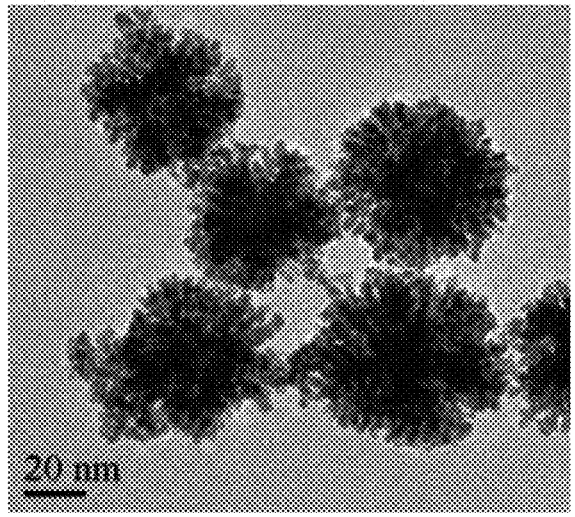
Figure 11D:
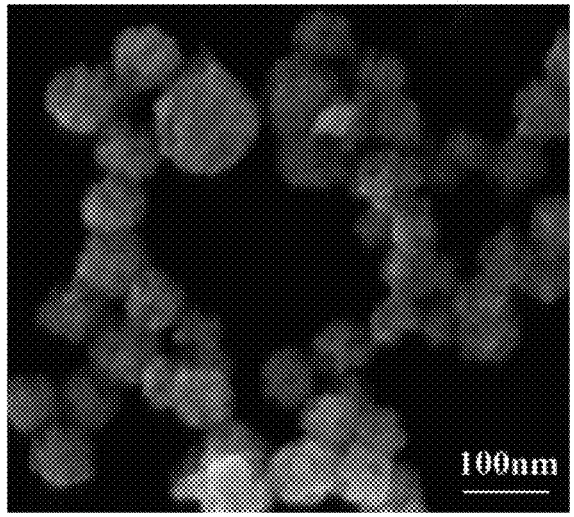

The morphology and structure of Pt—Pd porous NPs were first characterized by TEM and SEM. The particle size is around 40 nm. The porous structure is formed as hemispherical with concavities, which was confirmed by TEM (FIGS. 11A and 11B). The pores are made of fine Pt NPs that are forming several branched structure on the surface. The Pt NPs had an average diameter of 3-4 nm and were distributed evenly on the surface of Pd nanocore. The uniform porous structure has been further confirmed on the surface of NPs by SEM in FIG. 11D.

Furthermore, the formation of NPs was characterized by energy-dispersive X-ray spectroscopy (EDX) (not shown). The corresponding EDX analysis further confirmed the presence of elemental Pt and Pd in the bimetal NPs with an atomic Pt:Pd ratio of 8.7:1.2, which was close to the stoichiometric ratio of the two metal precursors (9:1). In addition, the XPS binding energies and the composition of the Pt—Pd NPs are investigated by XPS measurement. The Pt binding energy is 71.2 eV and the binding energy of Pd is 136.3 eV, both of which are in good agreement with the metallic Pt and Pd. The results confirmed that the Pt and Pd were in their coexistent form in the NPs. The wide angle XRD profile was assigned to (111), (200), (220), (311), and (222) diffractions of fcc crystal structure as one single phase. It indicated that the crystallographic structure is uniform and strongly revealing the formation of crystal structure.

3.2 Peroxidase-Like Catalytic Activities of Mesoporous Pt—Pd NPs

To investigate the peroxidase-like activity of Pt—Pd NPs, the catalysis to peroxidase substrate TMB or oPD was tested in the presence of $H_2O_2$. It was observed that Pt—Pd NPs could catalyze $H_2O_2$-induced oxidization of TMB or oPD, resulting in a deep blue color and yellow color solution within 10 min. These indicated that Pt—Pd NPs behave as peroxidase toward TMB and oPD oxidation with $H_2O_2$. These reactions are ascribed to the charge-transfer complexes derived from the one electron oxidation of TMB and oPD. The relative reaction is described in FIG. 13, in which $H_2O_2$ served as electron acceptors.

Figure 12A:
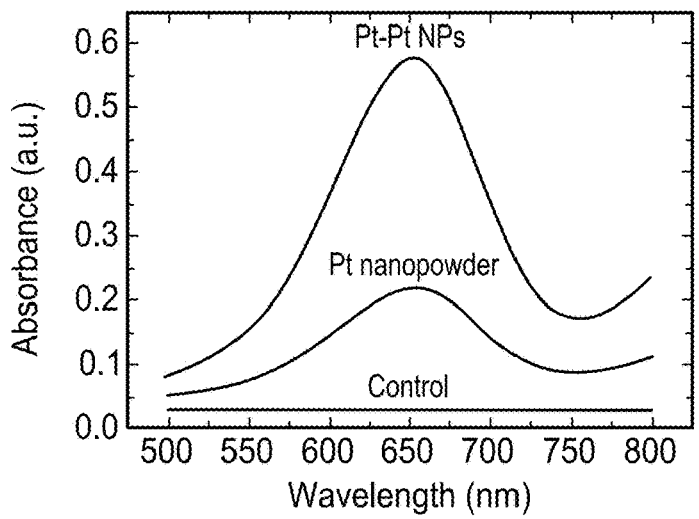
FIGS. 12A and 12B graphically represent the color reaction of TMB and OPD by $H_2O_2$ with and without Pt—Pd NPs.

The catalytic activity of Pt—Pd NPs was further studied. As shown in FIG. 12A, the absorbance of TMB oxidation changed by adding the same amount of different catalysts (5 μg mL$^{-1}$). Each solution exhibited blue color, corresponding to the absorbance at 652 nm. In addition, comparing with commercial Pt nanopowders, the TMB-$H_2O_2$ assay of Pt—Pd NPs achieved higher absorbance. Pt—Pd NPs could oxidize more TMB than Pt nanopowder under the same concentration of NPs. These results supported the hypothesis that Pt—Pd NPs have extremely high peroxidase-like activity. Therefore, the Pt—Pd NPs could have potential to circumvent intrinsic disadvantages of natural enzyme. The steady-state kinetic parameters of Pt—Pd NPs were further carried out by changing one concentration of TMB or $H_2O_2$ and keeping the other at the same time. According to the Lineweaver-Burk equation, the Michaelis constant, Km was obtained in FIGS. 14A-14D. The Km of Pt—Pd NPs and that of Pt nanopowder were shown in TABLE 4, as compared with HRP. It was found that the Km value of Pt—Pd NPs with a $H_2O_2$ substrate (5 mM) is lower than the one of HRP and other enzyme mimics, indicating that Pt—Pd NPs have stronger affinity toward $H_2O_2$. As the Km of Pt—Pd NPs for TMB was lower than that of Pt nanopowders, Pt—Pd NPs exhibited higher affinity than Pt nanopowders. The high peroxidase-like activity toward $H_2O_2$ is attributed to the unique porous structure, which could enlarge the specific surface area and mass transport rate. Similarly, the Pt—Pd NPs exhibited larger Kcat values toward TMB and $H_2O_2$ than that of Pt nanopowders, suggesting a higher peroxidase-like activity (TABLE 5). With the unique monometallic counter parts, the developed Pt—Pd porous nanocolloids have enhanced the surface to volume ratio and thus provided numerous catalytically active sites especially for hydrogen peroxide reaction. Therefore, the Pt—Pd NPs exhibited promising catalysis performance that they hold great potential to circumvent intrinsic disadvantages of enzyme for biomedical applications.

TABLE 4

Comparison of the Km of various enzyme mimics.

| | Pt nanopowders | Graphene-Fe3O4[49] | Pd NWs | PtPd NPs | HRP |
|---|---|---|---|---|---|
| Km [$H_2O_2$]/(mM) | 11.13 | 2.52 | 0.41 | 0.053 | 3.70 |
| Km [TMB]/(mM) | 5.24 | 4.52 | 4.15 | 1.78 | 0.43 |

TABLE 5

Comparison of parameters of various enzyme mimics.

| | Substrate | Km (mM) | $V_{max}$ (M s-1) | $k_{cat}$ (s-1) |
|---|---|---|---|---|
| PtPd NPs | TMB | 1.78 | $3.64 \times 10^{-7}$ | 0.0142 |
| | $H_2O_2$ | 0.053 | $0.926 \times 10^{-7}$ | 0.0036 |
| Pt nanopowders | TMB | 5.24 | $0.87 \times 10^{-7}$ | 0.0033 |
| | $H_2O_2$ | 11.14 | $0.309 \times 10^{-7}$ | 0.0012 |

Figure 12B:
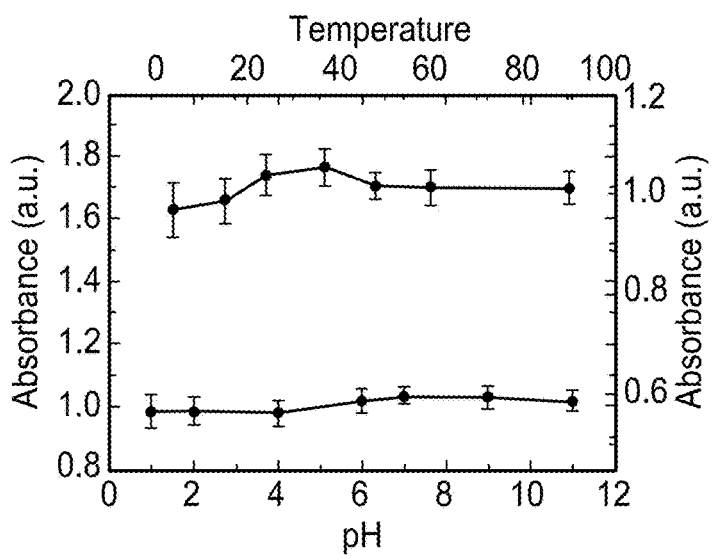
Figure 16:
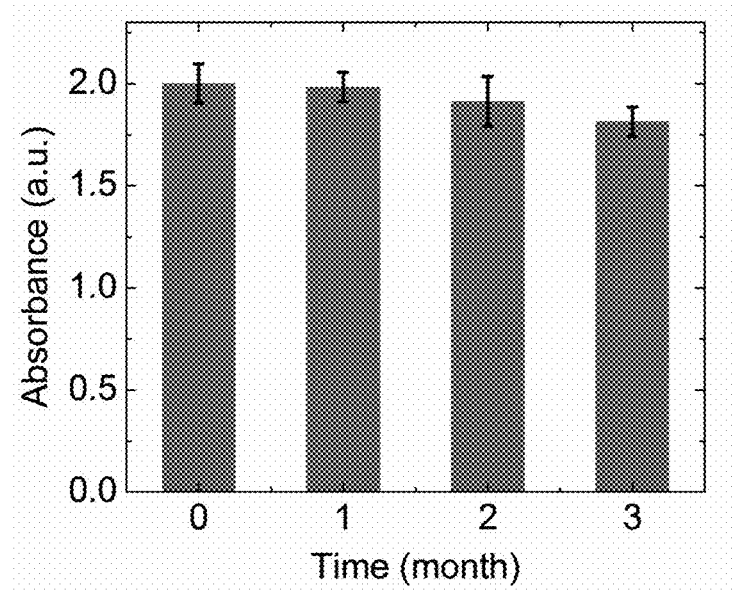
FIG. 16 graphically illustrates the long term stability of peroxidase activity of Pt—Pd NPs at room temperature. The stability under long-term storage conditions was also estimated for Pt NPs. HRP could maintain its activity for three weeks when HRP was stored at 4° C. In the case of Pt—Pd NPs, the initial activity was maintained above 95% during three months at room temperatures. These results showed that Pt—Pd NPs had far higher thermal stability than HRP at room temperature.

The thermal and pH stability of Pt—Pd NPs were further studied by compared with natural enzyme, HRP (FIG. 12B). Pt—Pd NPs exhibited a stable enzymatic catalytic activity toward $H_2O_2$ in the temperature range from 4 to 90° C., whereas the enzymatic activity of HRP drastically decreased over 40° C. due to the denaturalization of the enzyme under high temperature. Therefore, the peroxidase-like activity of NPs could be maintained at far higher temperature in comparison with enzyme. Pt—Pd NPs also exhibit invariable activity in the solution with the pH range from 1 to 11; whereas the activity of HRP is significantly inhibited when the pH was lower than 7.0 and totally denaturized when pH dropped to 2. In addition, even after longtime store (FIG. 16), the designed Pt—Pd NPs still maintain their strong peroxidase-like activity. Therefore, the demonstrated robust nature of Pt—Pd NPs encourages numerous biological applications which require strong and sensitive labels to serve as ultrasensitive reporter.

Figure 13:
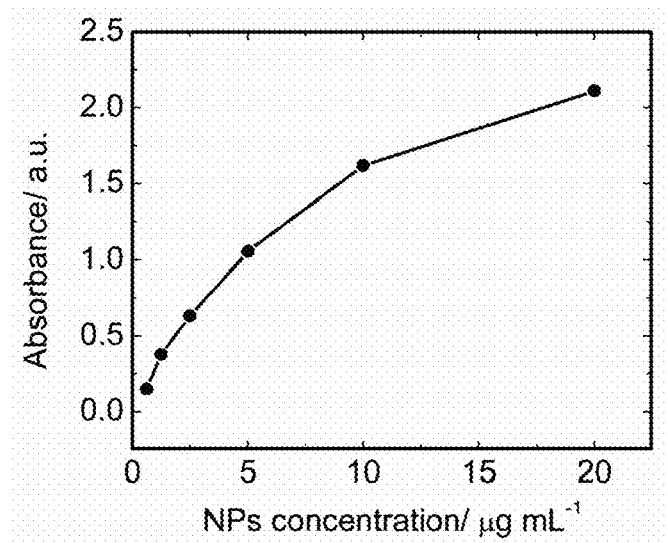
FIG. 13 graphically illustrates the comparison of the absorbance evolution at 652 nm for different concentration of Pt—Pd NPs. The higher the absorbance, the more the oxidation of TMB was observed. The peroxidase activity of Pt—Pd NPs was estimated by using TMB as a chromogenic substrate with different concentrations. Pt—Pd NPs exhibit stronger peroxidase activity as higher concentration of hydrogen, while it also presents fairly strong peroxidase activity at 0.5 μg mL$^{-1}$.
Figure 14A:
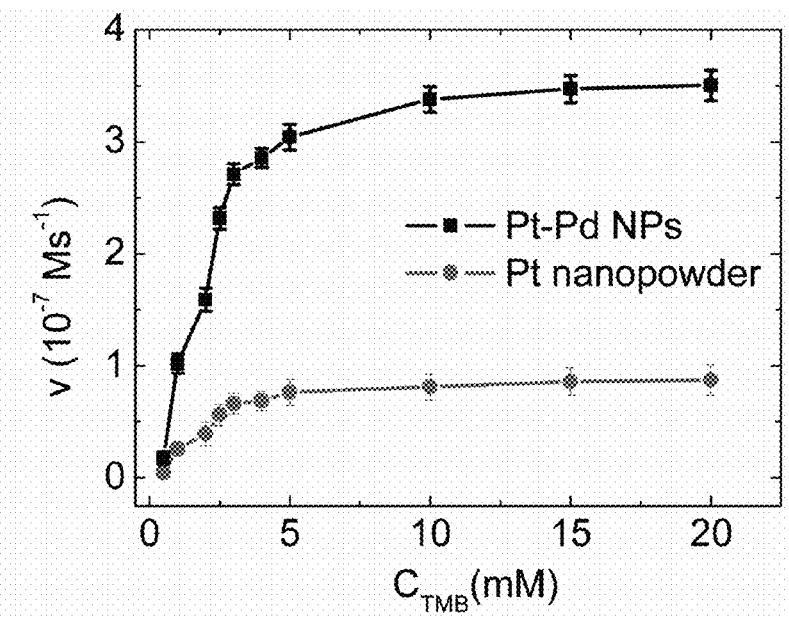
FIGS. 14A-14D graphically illustrate the steady-state kinetic assay Pt—Pd NPs.
Figure 14B:
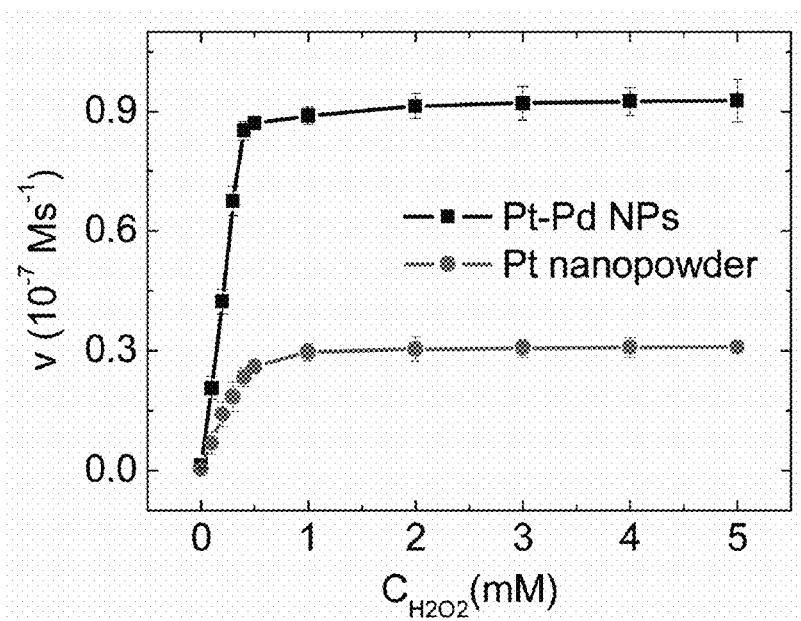
Figure 14C:
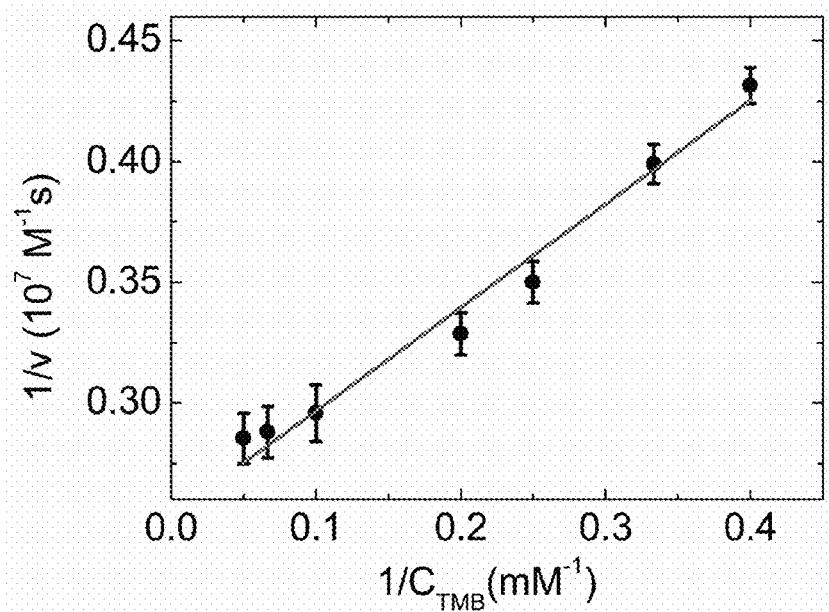
Figure 14D:
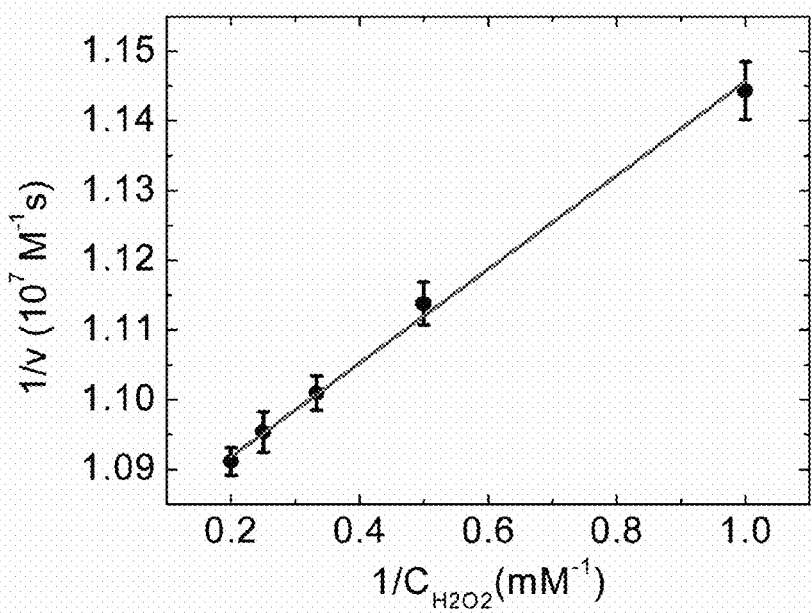
Figure 15:
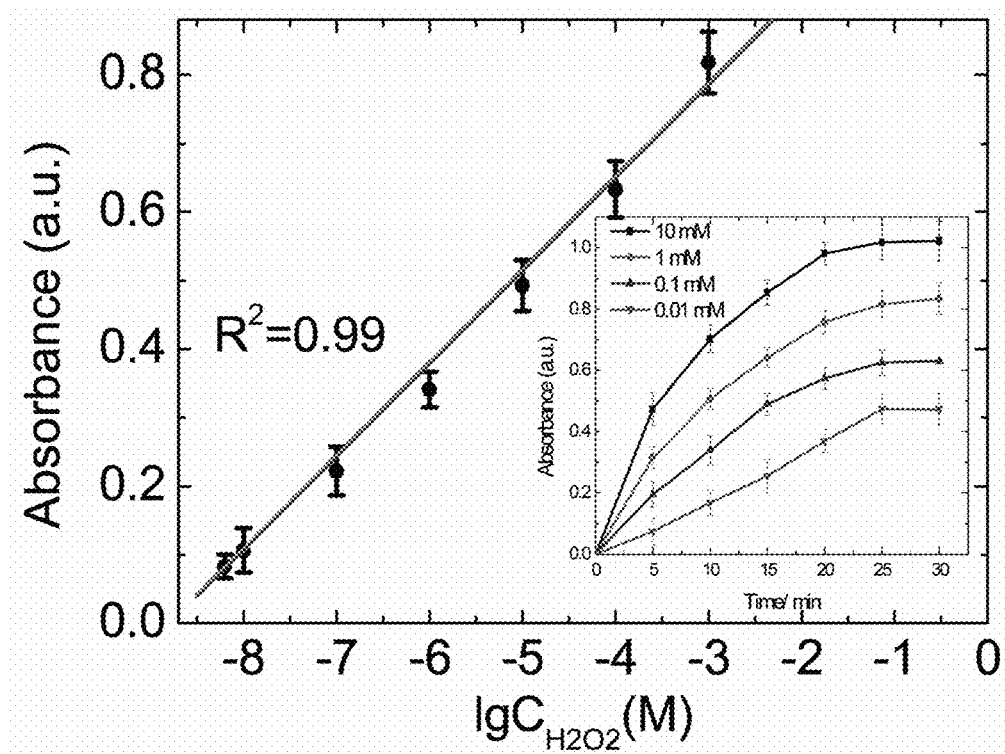
FIG. 15 graphically illustrates the calibration curve plotted on peroxidase-like reaction with different concentrations (1 mM, 100 μM, 10 μM, 1 μM, 100 nM, 10 nM, and 5 nM) of $H_2O_2$. All the conditions: 20 mM TMB, 5 mM $H_2O_2$, 0.2 mM HAc—NaAc buffer (pH 4.5) and 0.5 μg mL-1 Pt—Pd NPs. The inset is the absorbance evolution at 652 nm over time at several $H_2O_2$ concentrations.

On the basis of peroxidase-like activity of Pt—Pd NPs, the relationship between the peroxidase-like activity of Pt—Pd NPs and $H_2O_2$ concentrations was further studied in FIG. 15. It was clearly observed that the absorbance strongly depended on the $H_2O_2$ concentrations while it increased linearly (solid line) at low concentration range ($5 \times 10^{-6}$ to 10 mM). Moreover, the color intensity changed from colorless to dark blue with increasing $H_2O_2$ concentration. Hence, our methodology provides a visual detection method without any instrumentation complicated design. The inset of FIG. 15 is the absorbance evolution for different concentrations of $H_2O_2$ over time. When increasing the reaction time, the color intensity of different $H_2O_2$ concentration increased and reached the maximum value at 30 min. Furthermore, the impact of different concentrations of Pt—Pd NPs was also verified (FIG. 13). An easy recognized blue color was observed even with low concentration of Pt—Pd NPs. Therefore, the designed Pt—Pd NPs exhibit extremely strong peroxidase-like activity at low concentration and hold great potential for serving as color reagent.

3.3 Pt—Pd NPs as Label in Immunochromatography Test Strip (ITS)

The configuration and detection principle of our Pt—Pd NPs based ITS system is summarized as follows: the ITS system has sample pad, conjugated area, backing layer and nitrocellulose membrane. All the components are adhesively layer-by-layer together. The anti-p53 rabbit polyclonal antibody (Ab1) was used as labeled antibody covalently bound with Pt—Pd NPs and then modified onto the conjugated area. The anti-p53 monoclonal antibody (Ab2) was used as capture antibody and immobilized on the test line via immunoreaction. The goat anti-rabbit antibody served as control antibody and was conjugated on the control line of the nitrocellulose membrane. The distance between control line and test line is around 3 mm. Adding TMB for signal amplification. Positive test shows two lines, and negative test shows one line (only control line).

During the test process, capillary force draws the sample solution on the dipped ITSs. The synthesized Pt—Pd NPs were used as the color reagent in—immunocheromatography diagnostic system for rapid detection of proteins. The Pt—Pd labeled Ab1 (anti-p53 rabbit polyclonal antibody) binds with p53 antigen forming p53-Pt—Pd-Ab1 complex, and then will be released from conjugate area to move through the nitrocellulose membrane until reaches the test zone. Since the Ab2 (anti-p53 monoclonal antibody) captures part of the p53-Pt—Pd-Ab1 complex, a relatively light color line formed by the accumulated Pt—Pd NPs will be observed on the test zone. After the complex residual arrives at the control line, it will be captured by the goat anti-rabbit to form a visible complex line. Hence, two color lines should be observed if there is p53 in the sample solution (one in the test zone and the other in the control zone), whereas only one occurs in control test (in the control zone). Clearly, the color intensity of the test line is proportional to the amount of accumulated Pt—Pd NPs in the test zone associating with the amount of p53. The visibility of the dark color test line also depends on the concentration of p53 practically. With high concentration of p53 sample, an absolute line can be observed; with low concentration, the line could be fuzzy or almost invisible. Therefore, a signal-amplification method is needed for sensitive visual detection. Since TMB, a chromogenic reagent, can react with Pt—Pd NPs resulting in products with blue color, it is added onto the ITS surface used as signal amplifier at the last step.

To confirm the signal amplification of Pt—Pd NPs, the response of the sample with different concentration on Pt—Pd NPs based ITS was compared with colloidal gold based ITS (not shown). No visible color line occurred in the test zone and control zone for both colloidal gold based ITS and Pt—Pd NPs based ITS in control test. As increasing the concentration of p53, the test line of colloidal gold based ITS was observed when the concentration reached 100 ng $mL^{-1}$. Similarly, the Pt—Pd NPs based ITS without TMB amplifier can achieve similar detection limit for p53 (100 ng $mL^{-1}$); and no clear accumulated line was observed in the control zone. However, when TMB solution was dropped onto the test strips, the test line of Pt—Pd based ITS was clearly observed ever since the concentration reached 10 ng $mL^{-1}$. In addition, the Pt—Pd NPs based ITS in the presence of 100 ng $mL^{-1}$ p53 protein with TMB was significantly higher than that of the colloidal gold based ITS which exhibited a weak color response. Such dramatic signal amplification on Pt—Pd NPs based ITS is mostly due to the strong peroxidase-like activity of Pt—Pd NPs. These color lines resulted from the peroxidase reaction of $H_2O_2$, which reacts with Pt—Pd NPs producing blue color products. Therefore, with TMB amplifier, the Pt—Pd NPs based ITS have an absolutely lower detection limit than the conventional colloidal gold one.

3.4 Optimization of Parameters

Figure 17A:
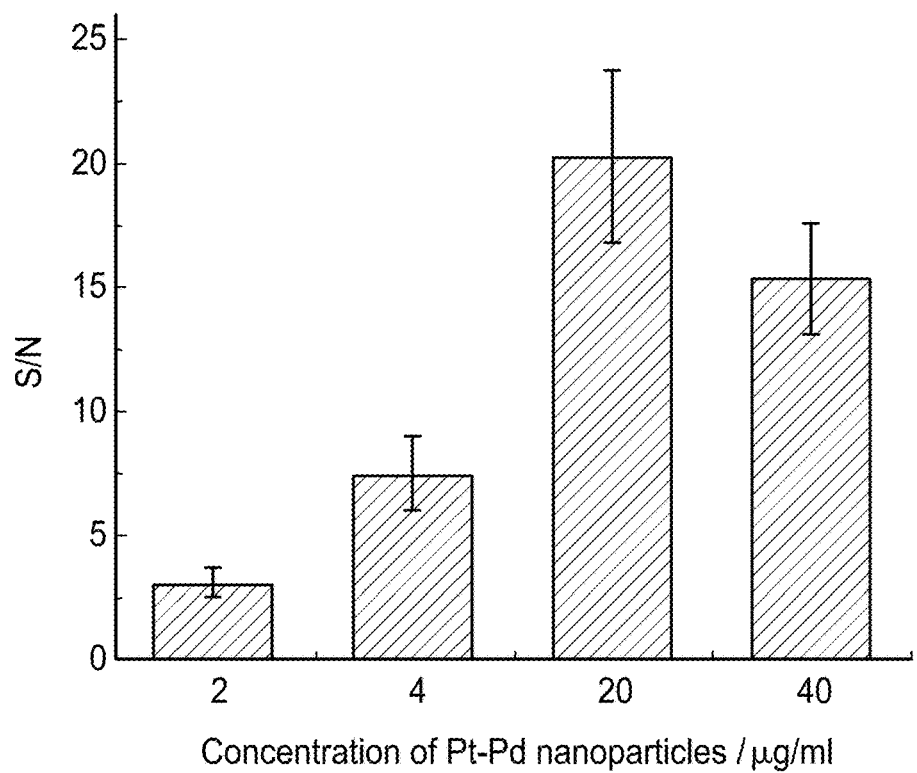
FIGS. 17A-17E.

The signal-to-noise (S/N) of ITS, which represents the immunoreaction efficiency and detection sensitivity, is affected by several perspectives: the amount of the Pt—Pd NPs conjugated on antibodies, the concentration of antibody associating with Pt—Pd NPs, the pH of the detection condition, the concentration of TMB, and the oxidation reaction time. Because ITS is a commercial method, the economic cost also influences the selection of optimal condition. As shown in FIG. 17A, the S/N increased up to 20 µg $mL^{-1}$ of Pt—Pd NPs conjugated on antibody because more Pt—Pd NPs could be captured by antibodies. After 20 µg $mL^{-1}$, the S/N decreased due to the nonspecific adsorption of residual NPs attributing to the background noise. Therefore, 20 µg $mL^{-1}$ of Pt—Pd NPs was used in the following experiments.

Figure 17B:
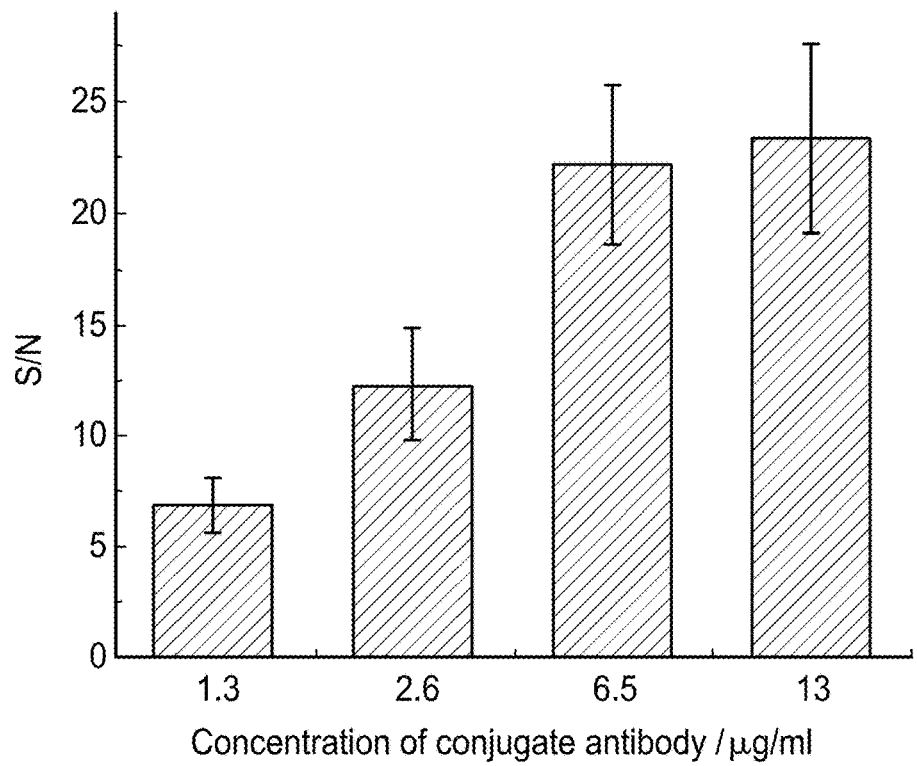

The signal increased with the increase of capture antibodies (Ab1) and tent to stable after 6.5 µg $mL^{-1}$ Ab1 (FIG. 17B). The increasing amount of antibody enhanced the immunoreaction efficiency contributing to the signal. Up to 13 µg $mL^{-1}$ antibodies, the response did not improve significantly. Considering the sensitivity of the response and limiting the usage of antibodies in the cost consideration, 6.5 µg $mL^{-1}$ antibodies was used to prepare the Pt—Pd NPs-Ab1 conjugate in the experiments.

Figure 17C:
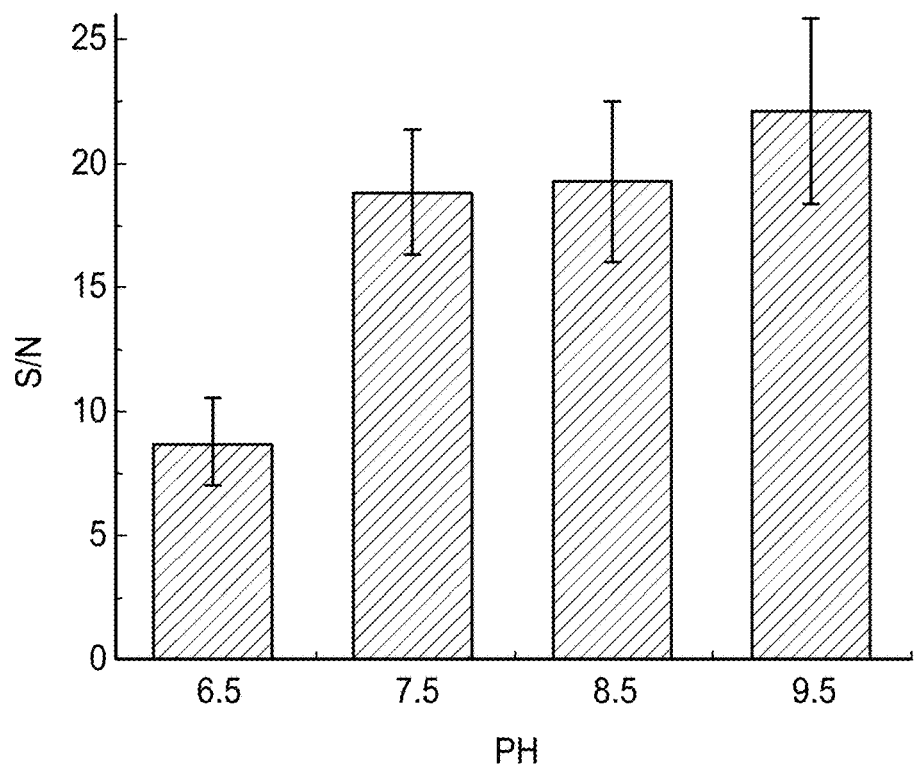

In addition, pH is another important parameter for immunoreactions. The highest S/N ratio was obtained at pH 9.5 (FIG. 17C), so this pH value was selected as the optimal condition.

Figure 17D:
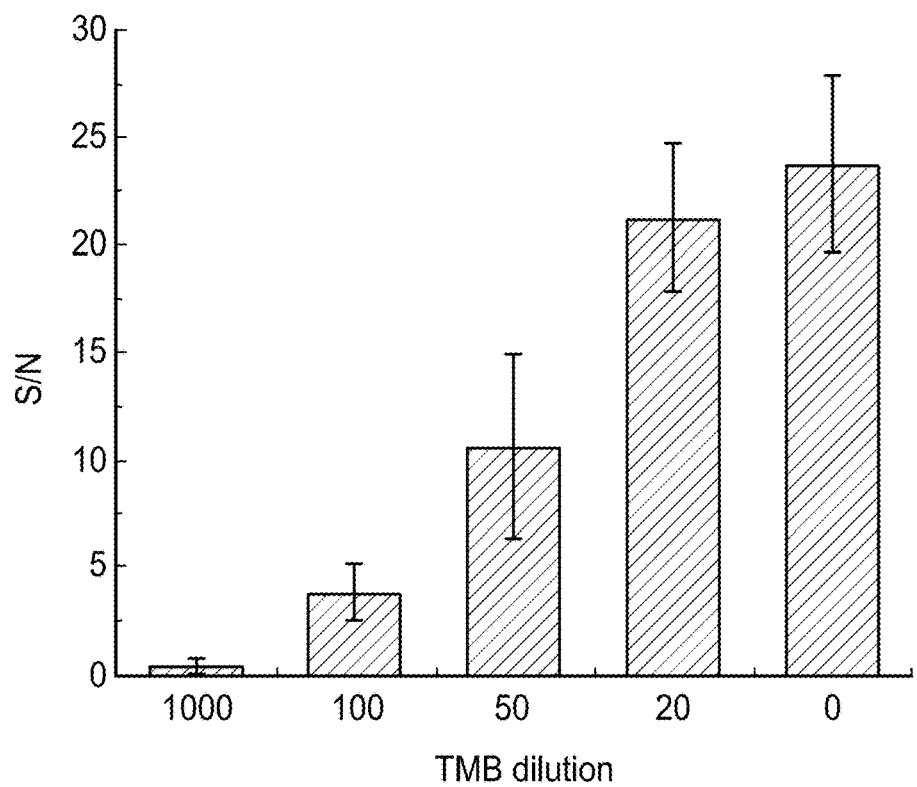

The concentration of TMB also has an effect on the response. As shown in FIG. 17D, the higher concentration of TMB, the higher S/N obtained. We found that 20-times dilution of TMB solution showed the best result.

Figure 17E:
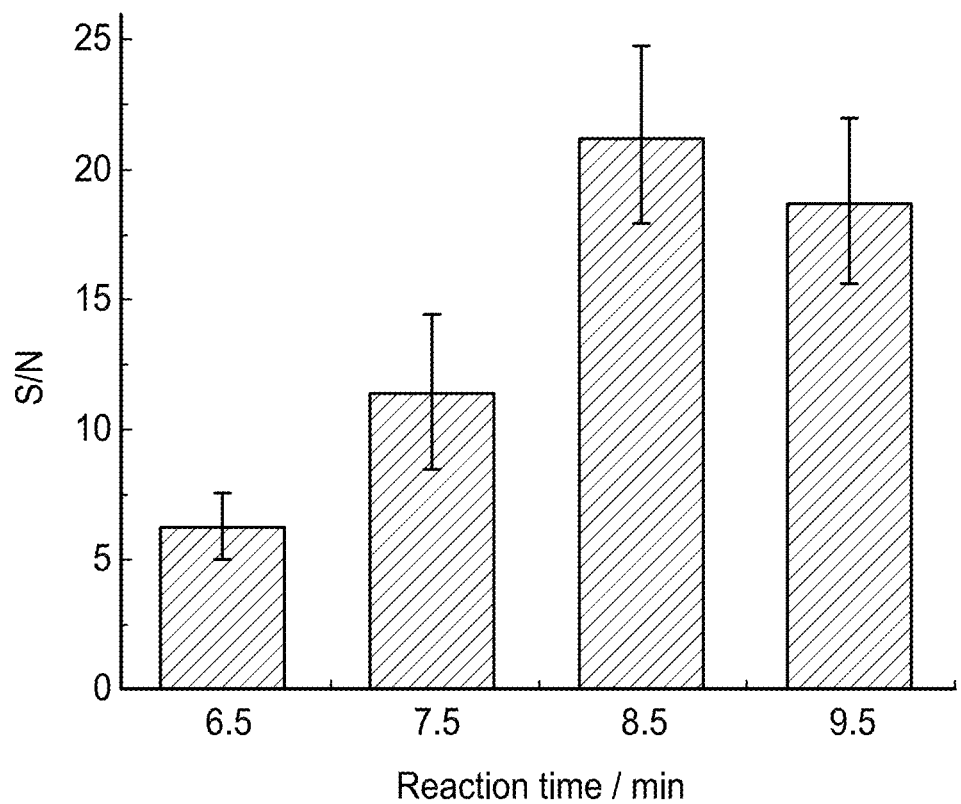

Reaction time by adding TMB showed an obvious effect on signal. The S/N increased as times went on because of the more amount of generated oxidation product. The highest response was obtained after we added TMB for 10 min (FIG. 17E), and then a blurred line occurred because of the diffusion. Therefore, 10 min were used to detect the signal after adding the TMB.

3.5 Quantitative Detection of p53 Using Pt—Pd Based ITS

Under optimal experimental conditions, the proposed ITS using Pt—Pd NPs labels in the amplification approach was challenged with different concentrations of p53. The quantitative detections were performed using a portable test strip reader to analyze the color intensity of the test line.

Figure 18:
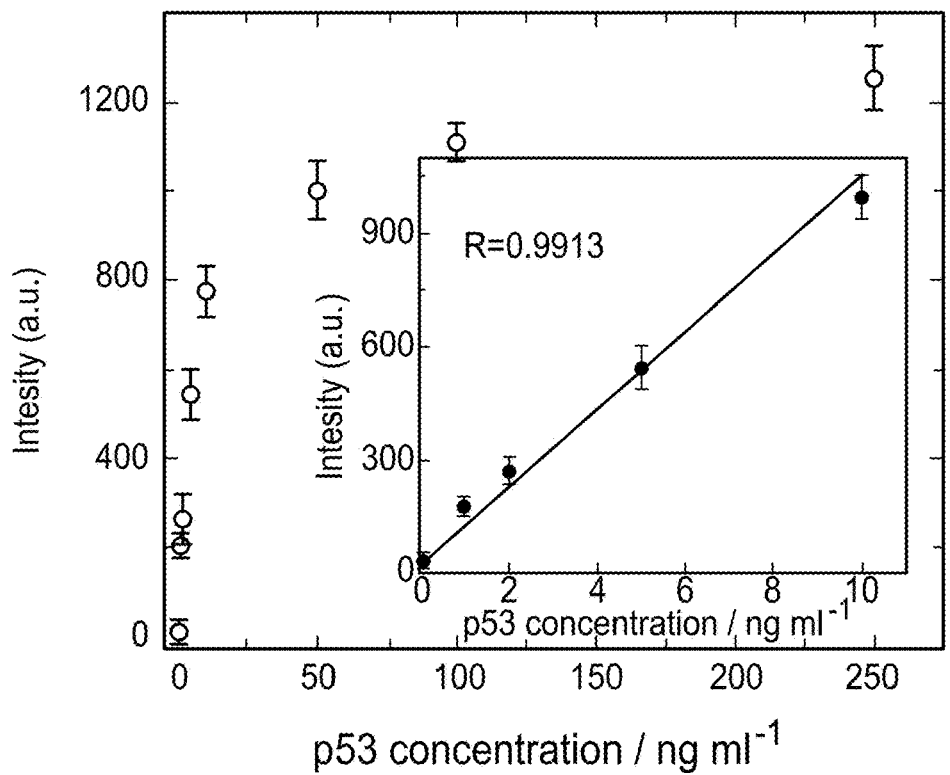
FIG. 18 graphically represents the relationship between the concentration of p53 and the test line intensity. Each point represents the average data value obtained from five times. Inset plot shows a linear response of color intensity to the concentration p53 protein when the concentration is less than 10 ng mL$^{-1}$.

Images and optical responses were recorded by portable strip reader in different concentration of p53 protein. Before adding the signal amplifier, TMB, onto the ITS, no clear test line was observed. After TMB was added, a color test line was visually observed on the test zone of ITS in a short time even under low p53 concentration (0.1 ng mL$^{-1}$) and the color intensity increased according to the increasing concentration of p53 (FIG. 18). There was no visual line observed on the test zone in the absence of p53, indicating negligible nonspecific adsorption under the optimized experimental condition. The effect of the signal amplification was tested by recording different stages of the reaction of Pt—Pd NPs and TMB (not shown). The results indicate that Pt—Pd could maintain its extremely strong peroxidase-like activity on ITS to achieve the purpose of signal amplification. Quantitative detection was further performed by recording the color intensity of test zone with the portable strip reader. It was observed that the peak intensity increased with increasing p53 concentration until reaching the plateau at 250 ng mL$^{-1}$. This saturation of the calibration curve was due to the physical size of NPs which limited the binding reaction. A linear relationship between the p53 concentration and the color intensity was obtained from 0.1 to 10 ng mL$^{-1}$ (inset of FIG. 18). The detection limit was estimated to be 0.05 ng mL$^{-1}$ from three times (S/N=3) at the standard deviation corresponding to the control detection, which was lower than commonly accepted colloidal gold NPs based ITSs.

3.6 Real Sample Analysis

Figure 19:
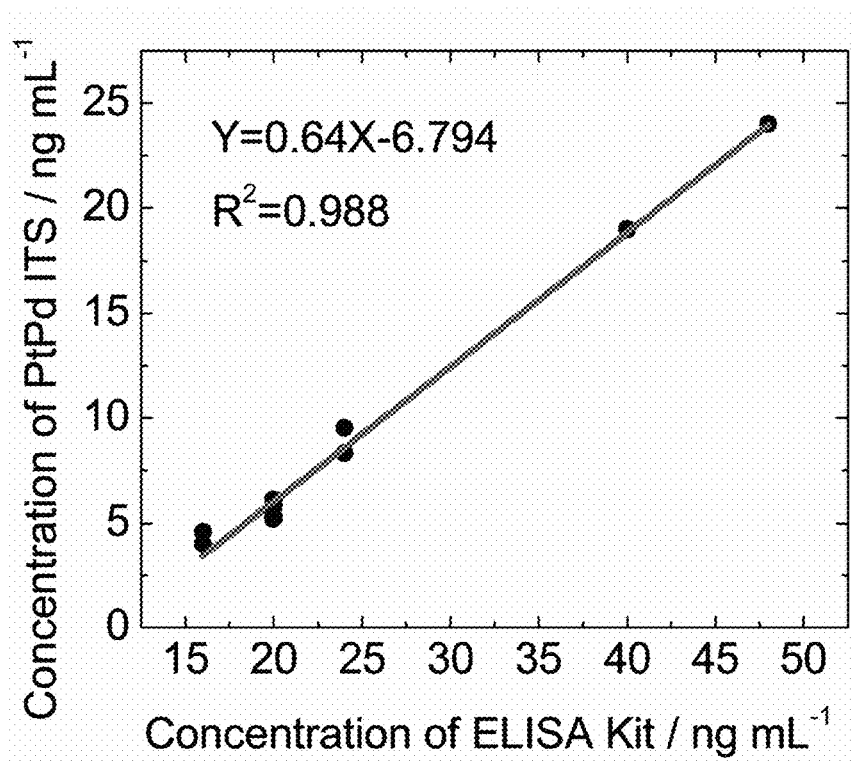
FIG. 19 graphically illustrates the comparison of signals obtained from Pt—Pd—ITS to those for ELISA kits. In both instances, the novel Pt—Pd—ITS assay compares favorably to the more traditional assays.

ELISA is a standard method for the clinical protein detection. This Pt—Pd based ITS to measure the p53 in a series of real clinical sample from local hospital patients who are diagnosed with acute pancreatitis. All of the pancreatitis samples were collected within 24 h of admittance to the hospital, diluted with buffer and left for 10 min before test. The concentration of p53 protein for gastric cancer often reaches 20 µg mL$^{-1}$, while the normal negative case is as low as 140 pg mL$^{-1}$. (Cho-Chung, Y. S., Biochim. Biophys. Acta, Mol. Basis Dis. 2006, 1762, 587-591; Nesterova, M., et al., Biochim. Biophys. Acta, Mol. Basis Dis. 2006, 1762, 398-403.) TABLE 6 shows the summarized results of the two analytical methods. The Pt—Pd—ITS showed that 11 of 70 clinical samples have p53 protein (15.7%). The samples that showed positive by test strips were confirmed by the test using ELISA kit (12 of 70). The results of Pt—Pd—ITS determination in clinical samples have good correlation with those by ELISA. To guarantee the accuracy of the results, analysis by test strips with visual assessment should be tested at least three times. In addition, statistical model was applied to evaluate the performance of the Pt—Pd—ITS. As shown in TABLE 7, signals obtained from ELISA and Pt—Pd—ITS was recorded and used to evaluate to performance of the new assay. As shown in FIG. 19, signals obtained from ELISA and Pt—Pd—ITS have a strong linear correlation with an R2 value of 0.988. These results demonstrated that Pt—Pd—ITS signals from the same set of p53 samples were in agreement with colorimetric signals from the commercial ELISA. Moreover, the test time and procedures of the ITS were shorter and more convenient than those of other methods. Our Pt—Pd—ITS was going to be a significant method for on-site and rapid detection of p53 in clinical sample.

TABLE 6

Real sample analysis.

| Serum | Number | p53 ELISA KIT | | PtPd-ITS | |
| --- | --- | --- | --- | --- | --- |
| | | Positive | % | Positive | % |
| GC | 19 | 7 | 36.8 | 6 | 31.5 |
| CAG | 18 | 4 | 22.2 | 4 | 22.2 |
| CGS | 10 | 1 | 10.0 | 1 | 10 |
| NC | 23 | 0 | 0 | 0 | 0 |
| Total | 70 | 12 | 17.1 | 11 | 15.7 |

GC = gastric cancer;
CAG = chronic atrophic gastritis;
CSG = chronic superficial gastritis; and
NC = negative control

TABLE 7

Relative signals obtained from ELISA and Pt—Pd-ITS.

| Positive Sample | Serum type | p53 ELISA KIT | | PtPd-ITS | |
| --- | --- | --- | --- | --- | --- |
| | | A$_{450}$ | ng/mL | intensity | ng/mL |
| WA-4# | GC | 1.03 | 40 | 1033 | 19 |
| WA-5# | GC | 0.512 | 20 | 627 | 6.1 |
| WA-9# | GC | 1.201 | 48 | 1052 | 20 |
| WA-11# | GC | 0.623 | 24 | 881 | 8.3 |
| WA-13# | GC | 0.634 | 24 | 1003 | 10 |
| WA-14# | GC | 0.507 | 20 | 558 | 5.2 |
| WA-18# | GC | 0.075 | 1 | 12 | 0 |
| WWY-10# | CAG | 0.409 | 16 | 503 | 4.6 |
| WWY-11# | CAG | 0.511 | 20 | 555 | 5.2 |
| WWY-13# | CAG | 0.523 | 20 | 621 | 5.8 |
| WWY-16# | CAG | 0.388 | 16 | 438 | 4 |
| QWY-5# | CGS | 0.510 | 20 | 561 | 5.3 |

GC = gastric cancer;
CAG = chronic atrophic gastritis; and
SG = chronic superficial gastritis 4. Conclusion In summary, we have successfully designed a mesoporous Pt—Pd NPs based ITS in a signal amplification procedure and demonstrated its usage in the sensitive, selective, and accurate quantification of p53. Enhanced sensitivity was achieved due to the strong peroxidase-like activity of Pt—Pd NPs, which exhibited obvious catalysis to TMB and therefore showed of target analytes.

The new ITS provides an easy-operation, low cost, and rapid approach for sensitive detection of protein biomarkers. It is expected to be widely used in medical laboratories, nursing homes, hospitals, and common households. It can also have a great impact on global health to diagnose health conditions in developing countries.

Example 4

This Example describes an improved ultrasensitive enzyme-linked immunosorbent assay using hydrangea-like antibody-enzyme-inorganic three-in-one nanocomposites.

Abstract: Protein-inorganic nanoflowers, composed of protein and copper(II) phosphate ($Cu_3(PO_4)_2$), have recently grabbed people's attention. Because the synthetic method requires no organic solvent and because of the distinct hierarchical nanostructure, protein-inorganic nanoflowers display enhanced catalytic activity and stability and would be a promising tool in biocatalytical processes and biological and biomedical fields. In this work, we first coimmobilized the enzyme, antibody, and $Cu_3(PO_4)_2$ into a three-in-one hybrid protein-inorganic nanoflower to enable it to possess dual functions: (1) the antibody portion retains the ability to specifically capture the corresponding antigen; (2) the nanoflower has enhanced enzymatic activity and stability to produce an amplified signal. The prepared antibody-enzyme-inorganic nanoflower was first applied in an enzyme-linked immunosorbent assay to serve as a novel enzyme-labeled antibody for Escherichia coli O157:H7 (E. coli O157:H7) determination. The detection limit is 60 CFU $L^{-1}$, which is far superior to commercial ELISA systems. The three-in-one antibody (anti-E. coli O157:H7 antibody)-enzyme (horseradish peroxidase)-inorganic ($Cu_3(PO_4)_2$) nanoflower has some advantages over commercial enzyme-antibody conjugates. First, it is much easier to prepare and does not need any complex covalent modification. Second, it has fairly high capture capability and catalytic activity because it is presented as aggregates of abundant antibodies and enzymes. Third, it has enhanced enzymatic stability compared to the free form of enzyme due to the unique hierarchical nanostructure.

1. Introduction

The enzyme-labeled antibody was established in the 1970s. The high catalytic activity of enzymes enables the determination of trace amounts of target and greatly contributes to signal amplification. Enzyme-linked immunosorbent assay (ELISA), an immunodiagnostic technique developed by Engvall and Perlmann, uses the enzyme-labeled antibody as one of its critical components. Since its development, ELISA has received widespread interest in application in the food industry, serological blood testing, and toxicology. Nowadays, ELISA holds a dominant position in the field of quantitative analysis because it is sensitive, selective, simple, and able to rapidly and simultaneously analyze a large number of samples. However, some limitations exist in its practical applications. Among all influence factors, the enzyme-antibody conjugate is the most critical reagent. The conventional enzyme-labeled antibody has relatively low sensitivity, and its main preparation methods, including the glutaraldehyde method and periodate method, are relatively complicated and inefficient. This has been a bottleneck for ELISA in the recent ever-growing requirement toward low-abundance targets. Therefore, improved enzyme-labeled antibody methods for ELISA are much needed to meet the current demand.

Scientists have been making efforts to improve the conventional enzyme-labeled antibody method to achieve high sensitivity. For example, the biotin-streptavidin system utilizes the strept(avidin) and biotinylated protein to amplify the signal. The immuno-PCR method combines the advantages of both ELISA and PCR to detect a low abundance of analytes. Antibody-functionalized metallic nanocrystals consist of thousands to millions of metal atoms and can be dissolved into individual ions and produce large numbers of chromophores, to replace conventional enzymes for achieving high signal amplification. The enzyme-loaded nanomaterial-labeled antibody has a high loading capacity for enzymes and shows remarkable signal amplification. However, most of the above preparation methods are based on complex covalent immobilization, with an inevitable loss of enzyme activity.

Recently, protein-inorganic hybrid nanoflowers made of protein and $Cu_3(PO_4)_2$ have attracted much attention since being first described by Richard Zare and co-workers (see Ge, J., et al., Nat. Nanotechnol. 2012, 7, 428-432). Because of their simple preparation (one-step coprecipitation method) without any organic solvent, and distinct hierarchical nanostructure, the enzyme-inorganic nanoflowers showed greatly enhanced catalytic activity and stability. This strategy of constructing protein-inorganic nanoflowers has provided a blueprint for other hybrid systems. For example, the glucose oxidase (GOx)-$Cu_3(PO_4)_2$ hybrid nanoflower has been applied to decompose organic pollutants efficiently, the laccase-$Cu_3(PO_4)_2$ nanoflower was utilized to coat a membrane filter for rapid and on-site detection of phenol, the derived α-amylase-calcium hydrophosphate ($CaHPO_4$) hybrid nanoflowers displayed dramatically enhanced enzymatic performance with a distinct $Ca^{2+}$-assisted allosteric effect from α-amylase, and the bovine serum albumin (BSA)-manganese phosphate ($Mn_3(PO_4)_2$) hybrid was first applied as a carrier for the loading of platinum nanoparticles (PtNPs) and the composite served as a high-efficiency Pt-based catalyst. In addition, multienzyme-coembedded organic-inorganic hybrid nanoflowers (GOx and HRP—$Cu_3(PO_4)_2$ nanoflowers) were prepared, which were able to achieve a one-step two-enzyme cascade catalytic reaction. There are also a few other works related to protein-inorganic nanoflowers. According to recent developments, protein-inorganic nanoflowers would be a promising tool in biomedical fields, in biocatalytical processes, and even in electrochemical catalysis. However, the above studies were restricted to only one kind of protein, the enzyme.

Figure 20:
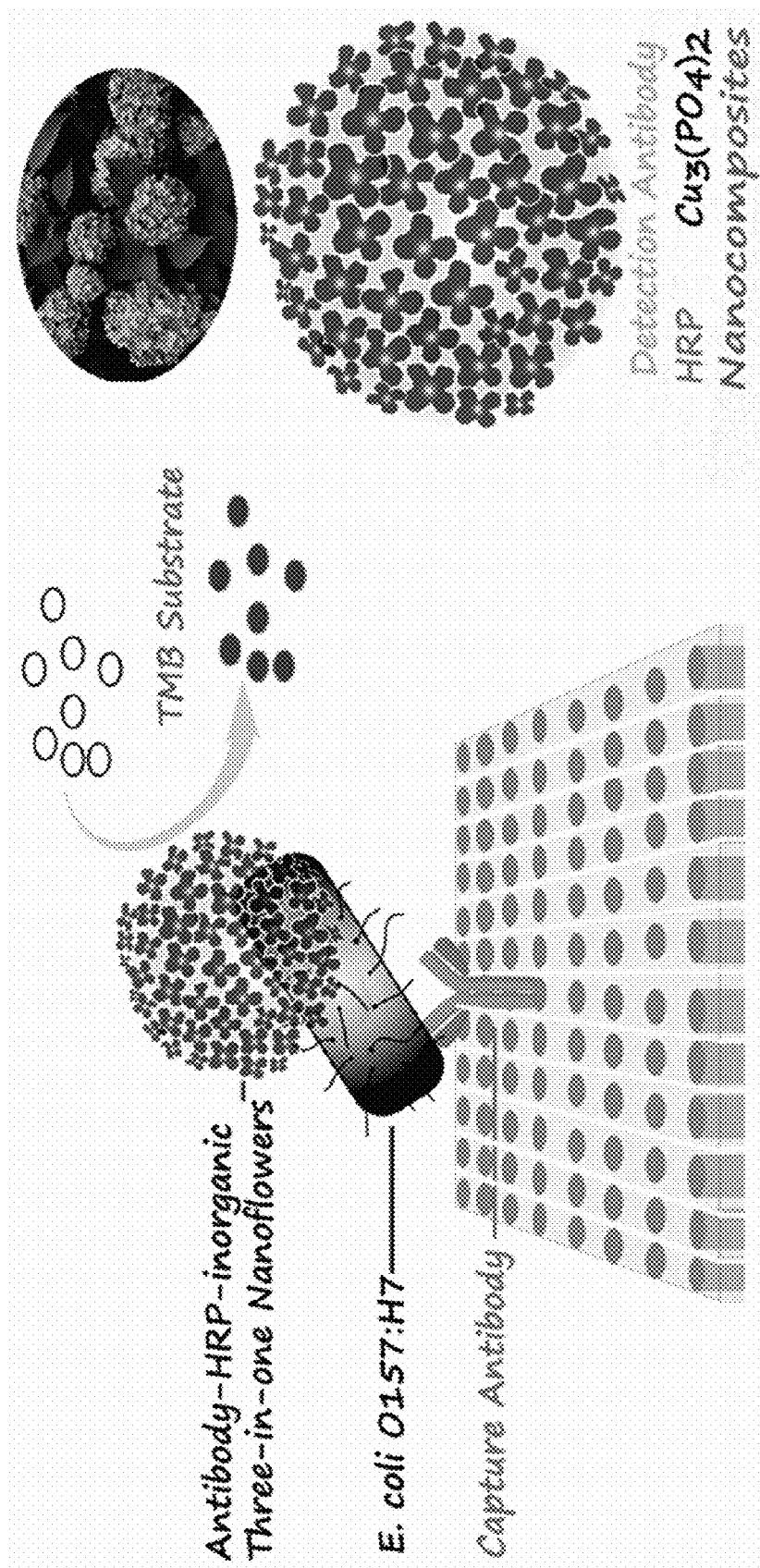
FIG. 20 schematically represents the hydrangea-like antibody-enzyme-inorganic three-in-one nanocomposite-based ultrasensitive ELISA for *E. coli* O157:H7 detection.

In this work, we first coimmobilized the enzyme, antibody, and $Cu_3(PO_4)_2$ into a three-in-one hybrid antibody-protein-inorganic nanoflower. The cooperation of enzyme and antibody conveys dual functions to the nanoflower: the specific capture ability toward the corresponding antigen and the enhanced enzymatic activity and stability for producing an amplified signal. The prepared antibody-enzyme-inorganic three-in-one nanoflower was further applied in ELISA to serve as a novel enzyme-labeled antibody. E. coli O157:H7 is an important foodborne pathogen, which can cause serious infection in low doses. Therefore, we chose E. coli O157:H7 as a model analyte. The enzyme-antibody-inorganic three-in-one nanoflower shows advantages over the commercial enzyme-labeled antibody. First, it is much easier to prepare with no need for any complex covalent modification. Second, it is an aggregate of numbers of antibodies and enzymes, so it has fairly high captive ability and catalytic activity. Furthermore, it has enhanced enzymatic stability compared to their free form due to its unique hierarchical nanostructure. It is highly expected that these three-in-one nanoflowers will ultimately have significant practical applications. The antibody-enzyme-inorganic nanoflower-based ELISA immunoassay procedure for E. coli O157 determination is illustrated in FIG. 20.

2. Experimental Section

2.1 Reagents and Materials

E. coli O157:H7 and other foodborne pathogens such as Salmonella and Listeria monocytogenes were kindly provided by Prof. Zhu at Washington State University. Mouse monoclonal anti-E. coli O157:H7 antibody (capture antibody/Ab1) was purchased from Abcam (Cambridge, Mass.). Goat polyclonal anti-E. coli O157:H7 antibody (detection antibody/Ab2) was purchased from KPL Inc. (Gaithersburg, Md.). Horseradish peroxidase (HRP), bovine serum albumin (BSA), copper(II) sulfate pentahydrate ($CuSO_4.5H_2O$), 3,3′,5,5′-tetramethylbenzidine (TMB) liquid substrate system for ELISA, phosphate-buffered saline (0.01 M phosphate buffer, 0.0027 M potassium chloride and 0.137 M sodium chloride, pH 7.4, at 25° C.), Tween 20, and potassium chloride were purchased from Sigma-Aldrich (USA). ELISA 96-well flat-bottom plates (Corning no. 9018) were purchased from Fisher Scientific (Pittsburgh, Pa.). All aqueous solutions were prepared using ultrapure water (18.2 MΩ cm) as required.

2.2 E. coli O157:H7 Sample Preparation

E. coli O157:H7 EDL933 was obtained from the STEC Center at Michigan State University. The E. coli O157:H7 cultures were activated in Luria-Bertani (LB) broth and washed with 0.01 M PBS, pH 7.0. A portion of washed E. coli O157:H7 suspension was 10-fold serial diluted and plated onto LB agar plates for cell enumeration. The rest of the E. coli O157:H7 suspension was heat treated, 0.5% (v/v) formalin added and mixed, and the mixture stored at −20° C. until analysis.

2.3 Preparation of Antibody-Enzyme-Inorganic Nanoflowers

The antibody-enzyme-inorganic nanoflowers were synthesized according to the one-step coprecipitation method reported by Zare's lab12 with some modifications. Typically, 120 μL of aqueous $CuSO_4$ solution (100 mM) was added to 13.805 mL of $H_2O$, 750 μL of 0.01 M PBS (pH 7.4), and 100 μL of 10% KCl solution containing 150 μL of HRP (1 mg $mL^{-1}$) and 75 μL of Ab2 (2 mg $mL^{-1}$), followed by incubation at 25° C. for 18 h. The scanning electron microscopy (SEM) samples were prepared by dripping a dilute aqueous dispersion of the as-prepared samples directly onto the conductive adhesive. The three-in-one nanoflower precipitate was collected through centrifugation (5000 rpm, 10 min), washed with deionized water, freeze-dried, and stored at −20° C. The nanoflowers were resuspended in PBS (50 μg $mL^{-1}$) by mildly vortexing. Then the solution was separated into small aliquots and stored at −20° C. before use.

2.4 Sandwich Three-in-one Nanoflower-Based ELISA of E. coli O157:H7

A 100 μL amount of 6 μg $mL^{-1}$ Ab1 diluted in 0.05 M carbonate buffer solution (pH 9.6) was added to a 96-well plate and incubated at 4° C. for 12 h. The plate was then aspirated and rinsed with 300 μL of PBST (0.05% Tween 20 in 0.01 M PBS) for each well four times to remove unbound antibodies, and the liquid was completely removed by inverting the plate and blotting it against clean paper towels. Afterward, 300 μL of PBSA (1% BSA in 0.01 M PBS) was added, incubated at 37° C. for 40 min, and washed. Then 100 μL of E. coli O157:H7 suspension at different concentrations was added to each well and incubated at 37° C. for 45 min. After washing four times, 100 μL of 8 μg $mL^{-1}$ HRP-$Ab_2$-$Cu_3(PO_4)_2$ nanocomposite was added to each well and incubated at 37° C. for 40 min. The plate was washed five times to remove unbound HRP-$Ab_2$-$Cu_3(PO_4)_2$ nanocomposite. Finally, 100 μL of TMB liquid substrate system for ELISA was added to each well and incubated at 37° C. for 20 min. The reaction was terminated using 50 μL of 2 N $H_2SO_4$, and the optical density of each well was determined within 30 min, using a Tecan Safire 2 microplate reader (Tecan, Switzerland) set to 450 nm with a wavelength correction of 540 nm.

3. Results and Discussion

3.1 Morphology Characterization of the Three-in-One Nanoflowers

Figure 21A:
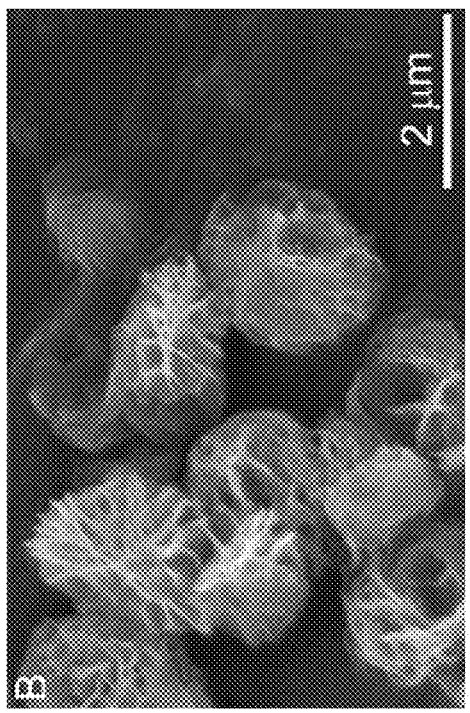
FIGS. 21A-21D are SEM images showing the morphologies of anti-*E. coli* O157:H7 antibody-HRP—$Cu_3(PO_4)_2$ three-in-one nanoflowers with magnifications from low to high.
Figure 21B:
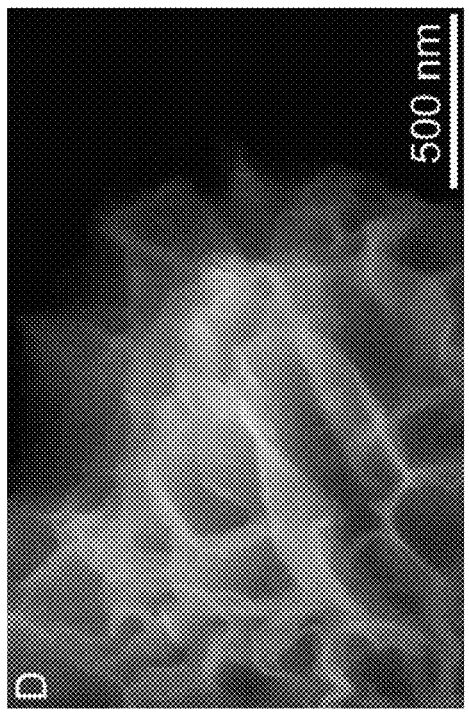
Figure 21C:
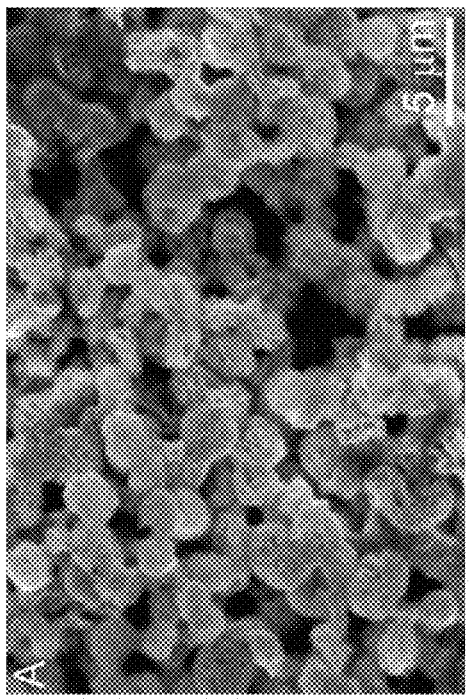
Figure 21D:
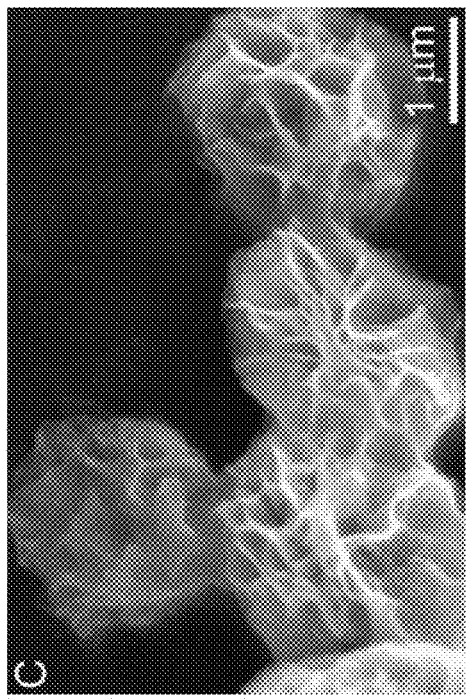

SEM images of the HRP-$Ab_2$-$Cu_3(PO_4)_2$ nanoflowers with the magnifications from low to high are shown in FIGS. 21A-21D. In the low-resolution SEM image, most of the HRP-$Ab_2$-$Cu_3(PO_4)_2$ nanoflowers look like hydrangeas with a uniform size of approximately 2 μm (FIG. 21A). The higher-resolution images of HRP-$Ab_2$-$Cu_3(PO_4)_2$ nanoflowers show that they have hierarchical structures with high surface-to-volume ratios, which really seem like they are assembled from hundreds of nanopetals (FIGS. 21B-21D). As elaborated by Jie Zeng and Younan Xia (Zeng, J., et al., Nat. Nanotechnol. 2012, 7, 415-416), the high surface area of the porous nanoflowers, the cooperative effects of the nanoscale-entrapped protein molecules, and the coordination between the amino acid residues of proteins and $Cu^{2+}$ endow the nanoflowers with enhanced stability and activity.

Figure 22A:
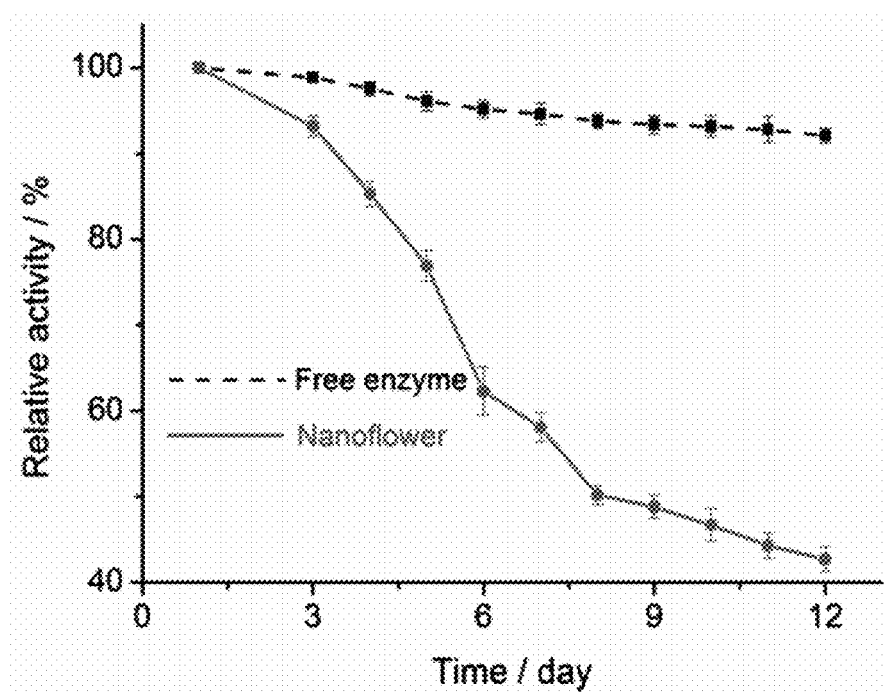
FIGS. 22A and 22B illustrate storage stability of antibody-HRP—$Cu_3(PO_4)_2$ nanoflowers.
Figure 22B:
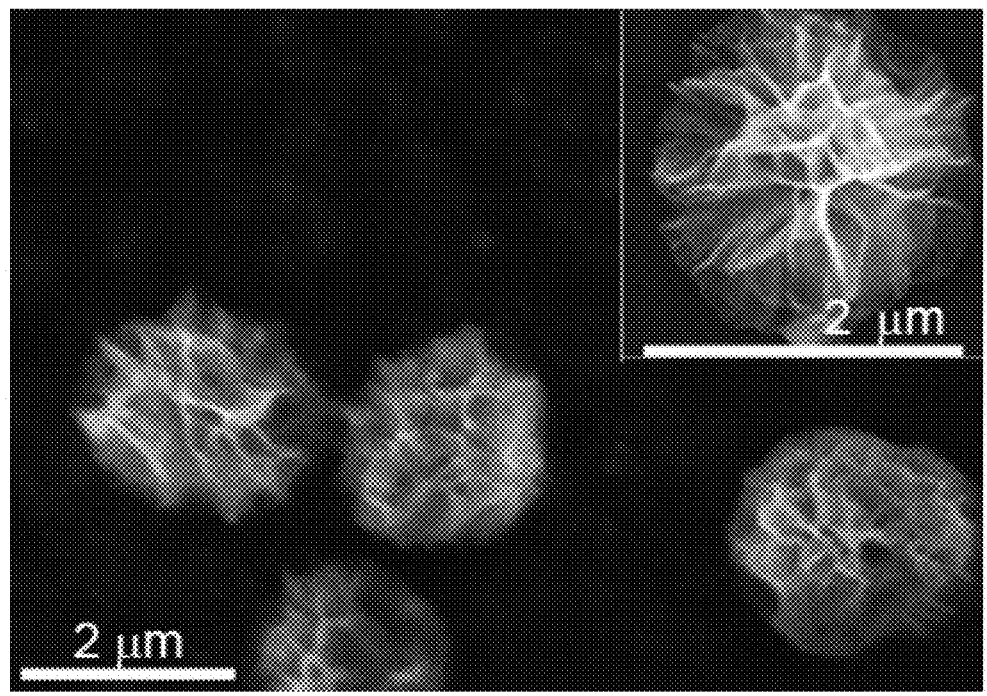

The stability of the antibody-HRP—$Cu_3(PO_4)_2$ nanoflower was further compared with that of the free HRP. The nanoflowers maintained ~93% of their catalytic activity after 10 days of storage in PBS at room temperature while the free HRP only retained ~47% of its original catalytic activity (FIG. 22A). Furthermore, morphologies of the nanoflowers had little change even after being stored in PBS for two months (FIG. 22B). The above results indicated the good stability of the nanoflowers.

Figure 23A:
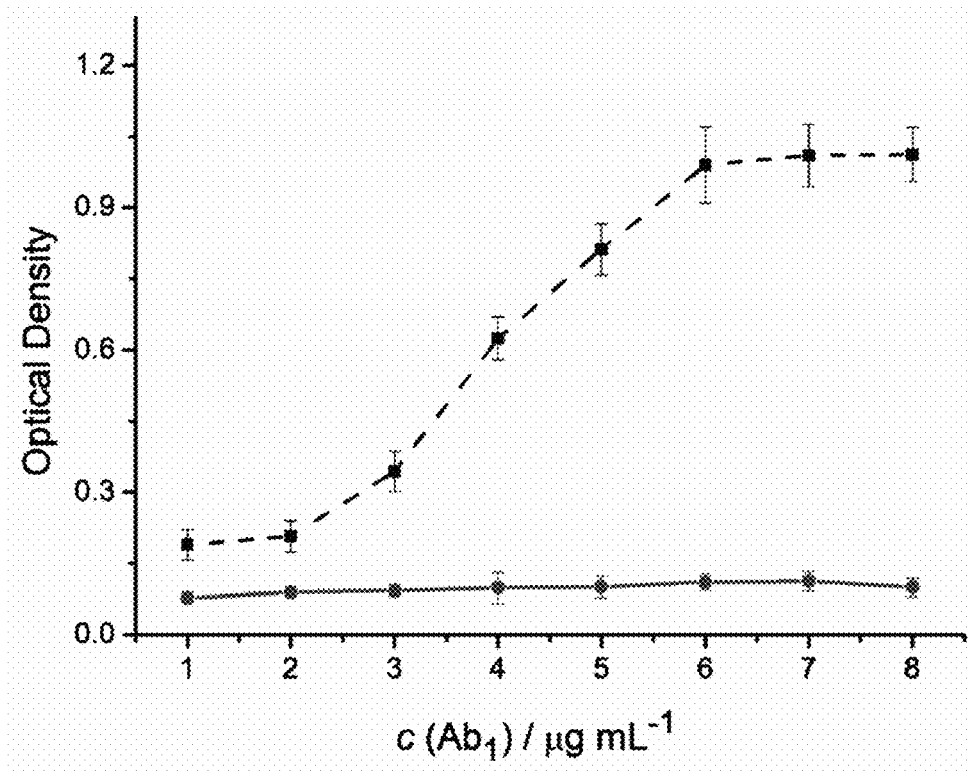
FIGS. 23A-23D graphically illustrate the optimization of ELISA detection conditions.
Figure 23B:
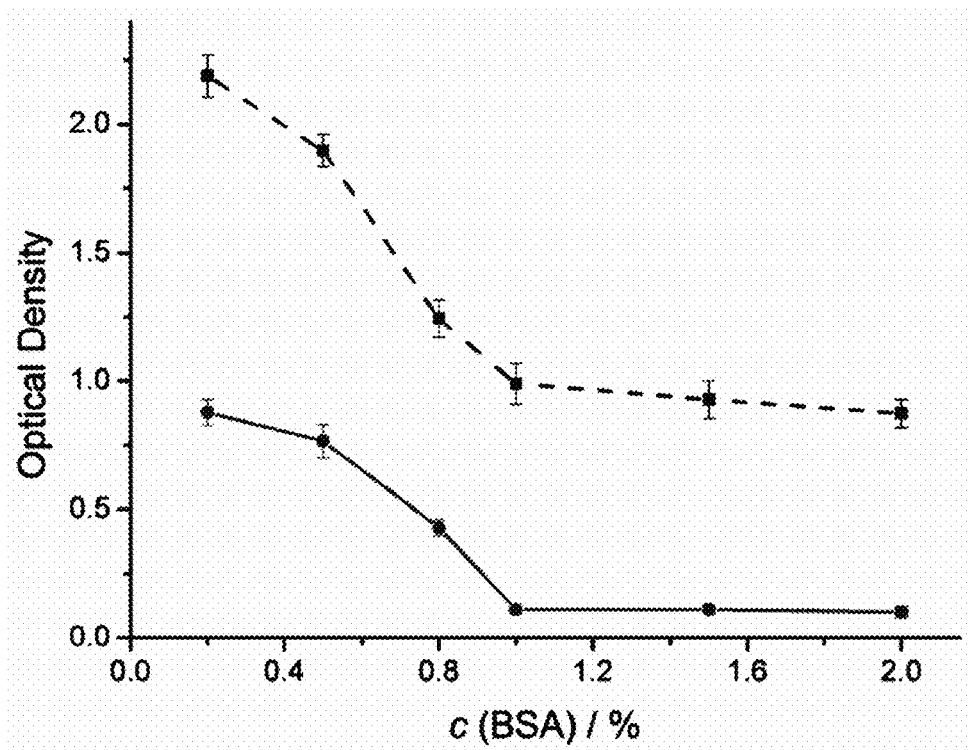
Figure 23C:
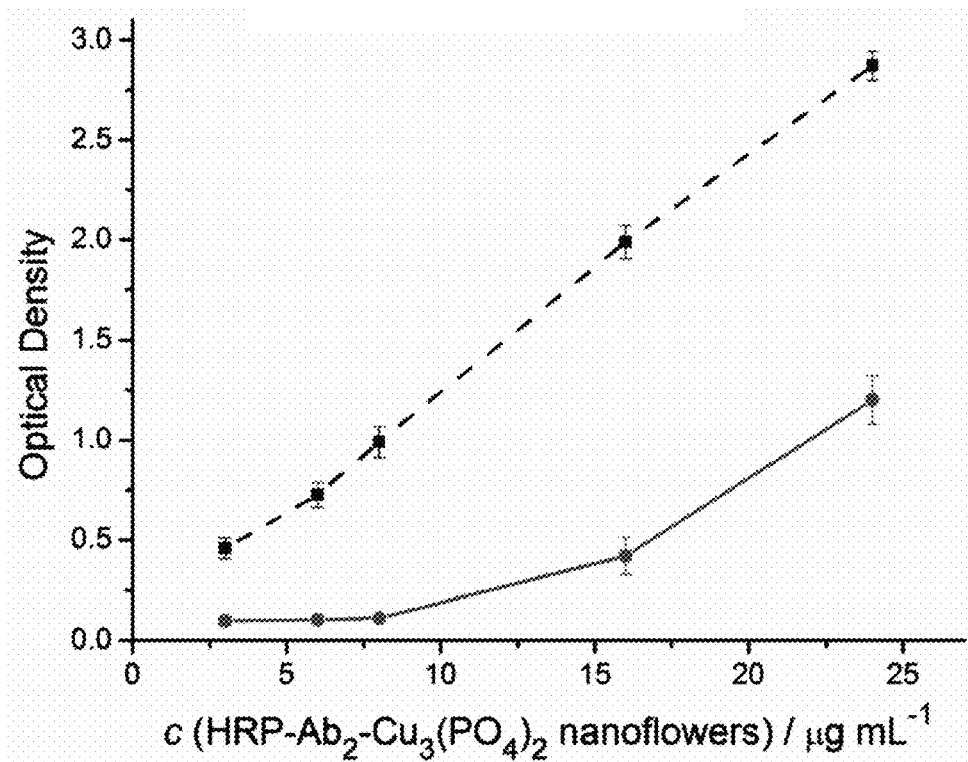
Figure 23D:
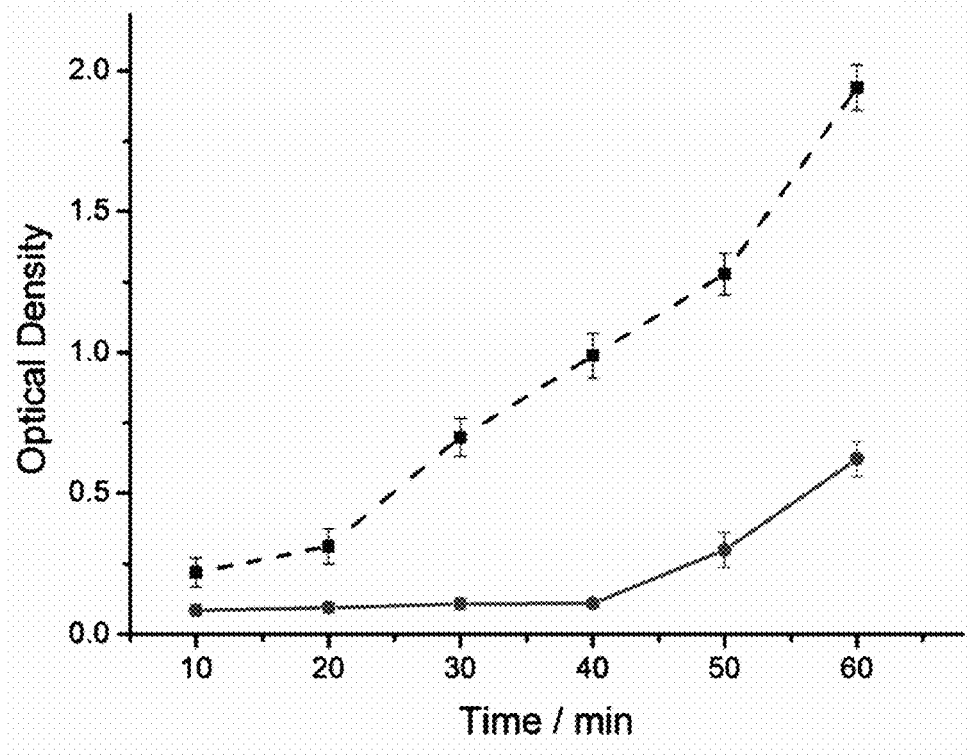

3.2 Optimization of Detection Conditions for Three-in-One Nanoflower-Based ELISA A variety of factors can affect ELISA performance. Herein, the optical densities of the control group (0 CFU $mL^{-1}$ E. coli O157:H7) and experimental group ($1.7 \times 10^6$ CFU $mL^{-1}$ E. coli O157:H7) were investigated simultaneously for evaluating the effects of four factors on detection sensitivity: the concentration of capture antibody, the concentration of blocking agent-BSA, the concentration of detection antibody (HRP-$Ab_2$-$Cu_3(PO_4)_2$ nanoflowers), and the incubation time of detection antibody. As shown in FIG. 23A, with increasing the concentration of $Ab_1$ from 1.0 to 7.0 μg $mL^{-1}$, the OD value of the experimental group kept increasing until 6.0 μg $mL^{-1}$ of $Ab_1$, indicating that 6.0 μg $mL^{-1}$ of $Ab_1$ coating is already sufficient and saturated for antigen binding. Hence, a concentration of 6.0 μg $mL^{-1}$ of $Ab_1$ was chosen to coat the 96-well plate. The concentration of blocking agent-BSA is also an important parameter for ELISA performance. FIG. 23B shows that the OD value of the experimental group decreased with increasing concentration of BSA and tended to level off after 1% BSA, and the OD value of control group showed false-positive results before 1% BSA, which is probably attributed to the fact that insufficient blocking agent might result in nonspecific interaction of the detection antibody. Therefore, 1% BSA was selected as the appropriate concentration of blocking agent. FIG. 23C shows that the concentration of detection antibody is another critical parameter. The OD value of the experimental group increased with increasing concentration of the HRP-$Ab_2$-$Cu_3(PO_4)_2$ nanoflowers, while the OD value of the control group began to yield false-positive results when adding 8 μg $mL^{-1}$ or more of HRP-$Ab_2$-$Cu_3(PO_4)_2$ nanoflowers. Therefore, 8 μg $mL^{-1}$ was selected as an appropriate concentration of HRP-$Ab_2$-$Cu_3(PO_4)_2$ nanoflowers. ELISA performance was also related to the incubation time of detection antibody. As revealed in FIG. 23D, the OD value of the control group produced false positive results after 40 min incubation time of HRP-Ab$_2$-Cu$_3$(PO$_4$)$_2$ nanoflowers. This is because longer incubation time of the antibody may lead to more nonspecific binding. Therefore, the optimal incubation time of detection antibody was 40 min.

3.3 Performance of the Three-in-One Nanoflower-Based ELISA for *E. coli* O157:H7

Figure 24:
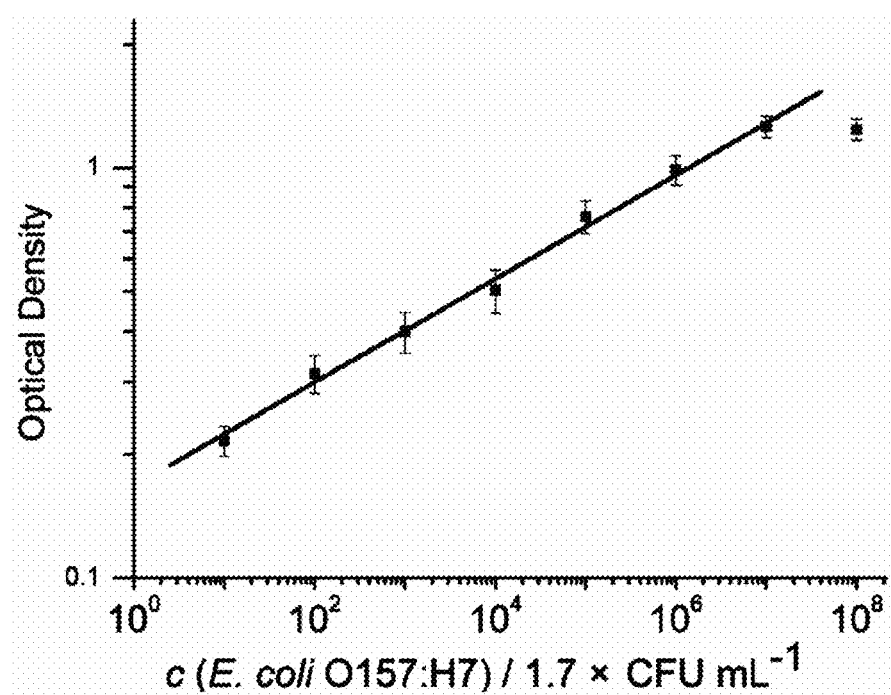
FIG. 24 graphically illustrates *E. coli* O157:H7 as quantified with a sandwich HRP-Ab2-$Cu_3(PO_4)_2$ nanoflower-based ELISA. Mean±standard deviation of three measurements is plotted. The optical density of each well was read at 450 nm with a wavelength correction of 540 nm. Each experiment was repeated three times to obtain the average data value.

Under the above optimized conditions, the three-in-one nanoflower-based ELISA system was used to quantitatively determine the concentrations of the *E. coli* O157:H7. The binding feasibility between antibody-HRP—Cu$_3$(PO$_4$)$_2$ nanoflower and *E. coli* O157:H7 was verified through the SEM images (not shown). From the ELISA quantitative results, the OD value increased with the increasing concentration of *E. coli* O157:H7. The calibration curve between the OD value and the concentration of *E. coli* O157:H7 is shown in FIG. 24, which reveals that the OD increment was highly sensitive to the concentration of *E. coli* O157:H7 and demonstrates that our hydrangea-like antibody-enzyme-inorganic three-in-one nanocomposite-based ELISA could provide a quantitative measurement of *E. coli* O157:H7 over $1.7 \times 10^1$ to $1.7 \times 10^7$ CFU mL$^{-1}$ with an ultrasensitive detection limit of 60 CFU L$^{-1}$. The detection limit is defined as the concentration of the analyte at which the extrapolated linear portion of the calibration graph intersects the baseline of the means of data from blank tests (Compendium of Chemical Terminology, IUPAC). This is better than most of the reported research results for quantitative determination of *E. coli* O157:H7 (TABLE 8) or comparable with the sensitive *E. coli* O157:H7 assay via new and sophisticated technology such as long-range surface plasmon-enhanced fluorescence spectroscopy (LSPFS) (see Huang, C. J., et al., Anal. Chem. 2011, 83, 674-677). These results indicated enhanced action of the antibody-enzyme-inorganic nanoflowers compared with the common HRP-conjugated antibody.

TABLE 8

Comparison of the Performance of Different *E. coli* O157:H7 Assays[a]

| Bacterium | Technique | Linear range (CFU mL$^{-1}$) | LOD (CFU mL$^{-1}$) | Reference |
|---|---|---|---|---|
| *E. coli* O157:H7 | chemiluminescence immunoassay | $4.3 \times 10^3$ to $4.3 \times 10^5$ | $1.2 \times 10^3$ | Zhang, Y., et al., Anal. Chem. 2014, 86, 1115-1122. |
| *E. coli* O157:H7 | LSPFS | $10^1$ to $10^6$ | 10 | Huang, C. J., et al., Anal. Chem. 2011, 83, 674-677. |
| *E. coli* O157:H7 | electrochemical ELISA | $10^3$ to $10^8$ | $10^3$ | Akanda, M. R., et al., Anal. Chem. 2013, 85, 1631-1636. |
| *E. coli* O157:H7 | amperometric immunosensor | $3.6 \times 10^3$ to $3.6 \times 10^6$ | $4.3 \times 10^2$ | Cheng, P., et al., Sens. Actuators, B 2014, 204, 561-567. |
| *E. coli* O157:H7 | electrochemical impedance spectroscopy | $10^3$ to $10^7$ | $10^3$ | Li, Y., et al., Biosens. Bioelectron. 2014, 58, 193-199. |
| *E. coli* O157:H7 | electrochemical biosensor | $10^2$ to $10^5$ | $10^2$ | Hassan, A. R. H. A. A., et al., Nanoparticle Tags. Biosens. Bioelectron. 2015, 67, 511-515. |
| *E. coli* O157:H7 | gold nanoparticle-enhanced ELISA | $10^2$ to $10^8$ | 68 | Shen, Z. Q., et al., Gut Pathog. 2014, 6, 14 10.1186/1757-4749-6-14 |
| *E. coli* O157:H7 | antibody-gold nanoparticle network ELISA | $10^1$ to $10^5$ | 3 | Cho, I. H., et al., Int. J. Food Microbiol. 2013, 164, 70-75. |
| *E. coli* O157:H7 | ConA-HRP-carbon nanotube-based ELISA | $10^2$ to $10^5$ | 100 | Zhang, H., et al., Chem. Commun. 2014, 50, 1848-1850. |
| *E. coli* O157:H7 | three-in-one nanoflower-based ELISA | $1.7 \times 10^1$ to $1.7 \times 10^7$ | 0.06 | this work |

[a]ELISA: enzyme-linked immunosorbent assay; LOD: level of detection; LSPFS: long-range surface plasmon-enhanced fluorescence spectroscopy.

Figure 25A:
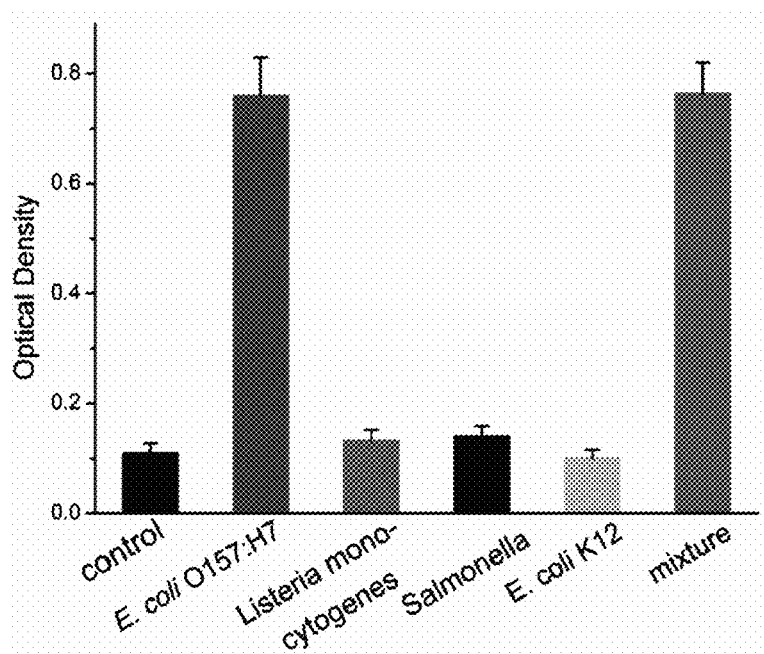
FIGS. 25A and 25B.

Specificity, stability, and recovery are important assessment criteria for the ELISA detection method. To assess the specificity of the nanoflower-based ELISA for *E. coli* O157:H7, we compared its specificity for nonpathogenic generic *E. coli* K12 and other foodborne pathogens such as *Salmonella* and *Listeria monocytogenes*. The OD values for other bacteria are roughly the same with the control group, while *E. coli* O157:H7 or culture mixtures give a high OD value (FIG. 25A). These results suggested that the developed nanoflower-based ELISA for *E. coli* O157:H7 is specific to *E. coli* O157:H7.

Figure 25B:
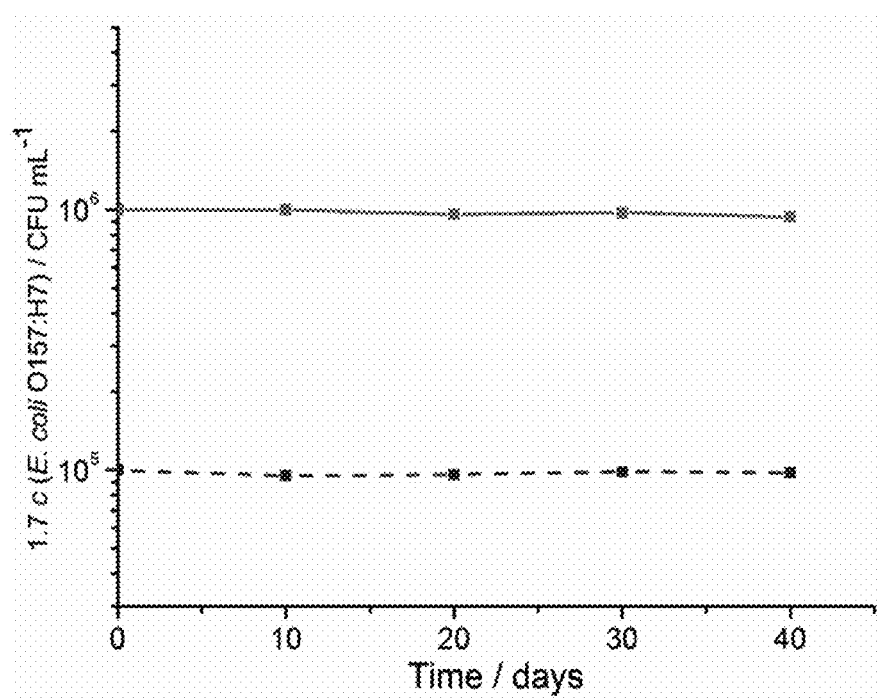

The stability of the three-in-one nanoflower was further tested in the *E. coli* O157:H7 ELISA. Two test samples with different concentrations of *E. coli* O157:H7 ($1.7 \times 10^5$ CFU mL$^{-1}$ and $1.7 \times 10^6$ CFU mL$^{-1}$) were assayed using the same lot of HRP-Ab$_2$-Cu$_3$(PO$_4$)$_2$ nanocomposites over a 40-day period. The ELISA performance shown in FIG. 25B indicated the acceptable stability of the antibody-enzyme-inorganic nanoflowers and its potential to substitute for common existing enzyme-conjugated antibodies in ELISA systems. Recovery experiments are used to determine whether assays are affected by interfering factors. Different concentrations of *E. coli* O157:H7 were spiked into tap water and lake water and then analyzed for recovery. The results showed that recoveries were in the range of 92.9-101.8% (TABLE 9), which confirmed the high accuracy of the nanoflower-based ELISA and its great potential for practical application in the detection of *E. coli* O157:H7 in water.

TABLE 9

Recoveries for *E. coli* O157:H7-Spiked Samples

| Sample | Added (CFU mL$^{-1}$) | Found (CFU mL$^{-1}$) | Recovery (%) |
|---|---|---|---|
| tap water 1 | $1.7 \times 10^2$ | $1.65 \times 10^2$ | 97.6 |
| tap water 2 | $1.7 \times 10^4$ | $1.72 \times 10^4$ | 101.8 |
| tap water 3 | $1.7 \times 10^6$ | $1.63 \times 10^6$ | 96.4 |
| lake water 1 | 0 | not detectable | — |
| lake water 2 | $1.7 \times 10^2$ | $1.58 \times 10^2$ | 92.9 |
| lake water 3 | $1.7 \times 10^4$ | $1.61 \times 10^4$ | 94.7 |

4. Conclusions

For the first time, we developed a hydrangea-like antibody-enzyme-inorganic three-in-one nanocomposite as a novel enzyme-labeled antibody and applied it to ELISA for detection of *E. coli* O157:H7. The antibody-enzyme-inorganic nanoflower is simply synthesized by a one-step coprecipitation method and does not require any organic solvent. It has the function of an antibody to specifically interact with the corresponding antigen and also has enhanced enzymatic activity and stability. The anti-*E. coli* O157:H7 antibody-HRP—$Cu_3(PO_4)_2$ nanocomposite was used to replace the common HRP-conjugated antibody and was applied in the ELISA for *E. coli* O157:H7 determination. The results showed that the three-in-one nanoflower-based *E. coli* O157:H7 ELISA had an ultrasensitive performance with a wide detection range ($1.7 \times 10^1$ to $1.7 \times 10^7$ CFU mL$^{-1}$). The detection limit is far superior to that of commercial ELISA systems. The easy preparation of these nanocomposites and the ultrasensitive detection of *E. coli* O157:H7 show potential application in real samples. Furthermore, the strategy of making antibody-enzyme-inorganic nanoflowers as described in this work can be readily extended to many other hybrid systems. For example, different antibodies could serve as components in nanoflower preparation to expand the use of antibody-enzyme-inorganic nanoflower-based ELISA to the detection of various targets. In addition, enzymes other than HRP could be used in nanoflowers that would not require colorimetric assay but rather an alternative mode of detection depending on the enzyme chosen. The methodology proposed here could potentially replace the common existing enzyme-labeled antibody method in ELISA and will have significant prospects in the practical detection of other pathogenic bacteria or clinically relevant molecules.

Example 5

This Example describes a one-pot bioinspired synthesis of all-inclusive protein-protein nanoflowers for point-of-care bioassay. Showing proof of concept, the nanoflowers were used for successful detection of *E. coli* O157:H7 from milk.

Abstract: Protein-protein conjugates play a vital role in bioassays with their inherent functions of biological recognition and signal amplification. Herein, a one-pot green method for synthesis of all-inclusive protein-protein nanoflowers has been developed. The protein-protein nanoflowers integrate both essential functions of biological recognition and signal amplification, and they were used as ideal signal labels for the sensitive point-of-care detection of *Escherichia coli* O157:H7. Especially noteworthy, the prepared Con A-invertase-CaHPO$_4$ hybrid nanoflowers simultaneously loaded sufficient invertase and enhanced the activity of the immobilized invertase, which fits well with the requirements of signal labels for bioassays. Due to the conversion of sucrose to glucose by invertase, Con A-invertase-CaHPO$_4$ hybrid nanoflowers were successfully used for the reliable point-of-care detection of food pathogens by a personal glucose meter. The presented approach successfully resolved the bottleneck in preparing protein-protein conjugate-based signal labels for bioassays using enzyme-based signal amplification strategies, which holds great promise to develop on-demand protein-protein conjugates for a variety of applications extending from biosensors and biomedicine to energy, environmental monitoring and remediation.

1. Introduction

Proteins play an important role in biosensing due to their fascinating functions of analyte biorecognition and signal amplification. Proteins for recognition (e.g., antibodies) have been widely used in bioassays for their high specific interaction with a variety of target analytes, ranging from small molecules to proteins and even cells. Signal enhancement based on proteins (e.g., enzymes) can afford diverse amplified signal readout via many different enzymatic reactions. Accordingly, protein-protein conjugate-based bioassay techniques, such as Western blotting and enzyme-linked immunosorbent assay (ELISA), are the most popular techniques for bioassay. Therefore, constructing high-performance protein-protein conjugates combining the analyte biorecognition unit and signal amplification unit plays a pivotal role in the commonly used technique. To date, considerable endeavors have been made to develop reliable approaches for the synthesis of protein-protein conjugates and exploration of ideal nanoparticles for immobilizing protein-protein conjugates. The relatively complicated preparation and tedious purification processes often bring inevitable sacrifice in function of the protein-protein conjugates, such as the deactivation of recognition proteins and the activity loss of enzymes. Consequently, to resolve this bottleneck, there is an urgent desire to develop a suitable process to prepare protein-protein conjugates containing the functions of target recognition and signal amplification while retaining high activity of proteins, especially for maintaining the activity of immobilized enzymes. Recently, a facile method has been reported to prepare organic-inorganic hybrid nanoflowers, which uses a kind of protein (enzyme) as the organic component and copper(II) phosphate as the inorganic component. It is inspiring that the as-prepared hybrid nanoflowers presented improved catalytic activity and durability. Spurred on by this facile method, we present a proof-of-concept approach to synthesizing all-inclusive, multifunctional protein-protein nanoflowers capable of biological recognition and signal amplification for point-of-care (POC) detection of food pathogens.

Figure 26:
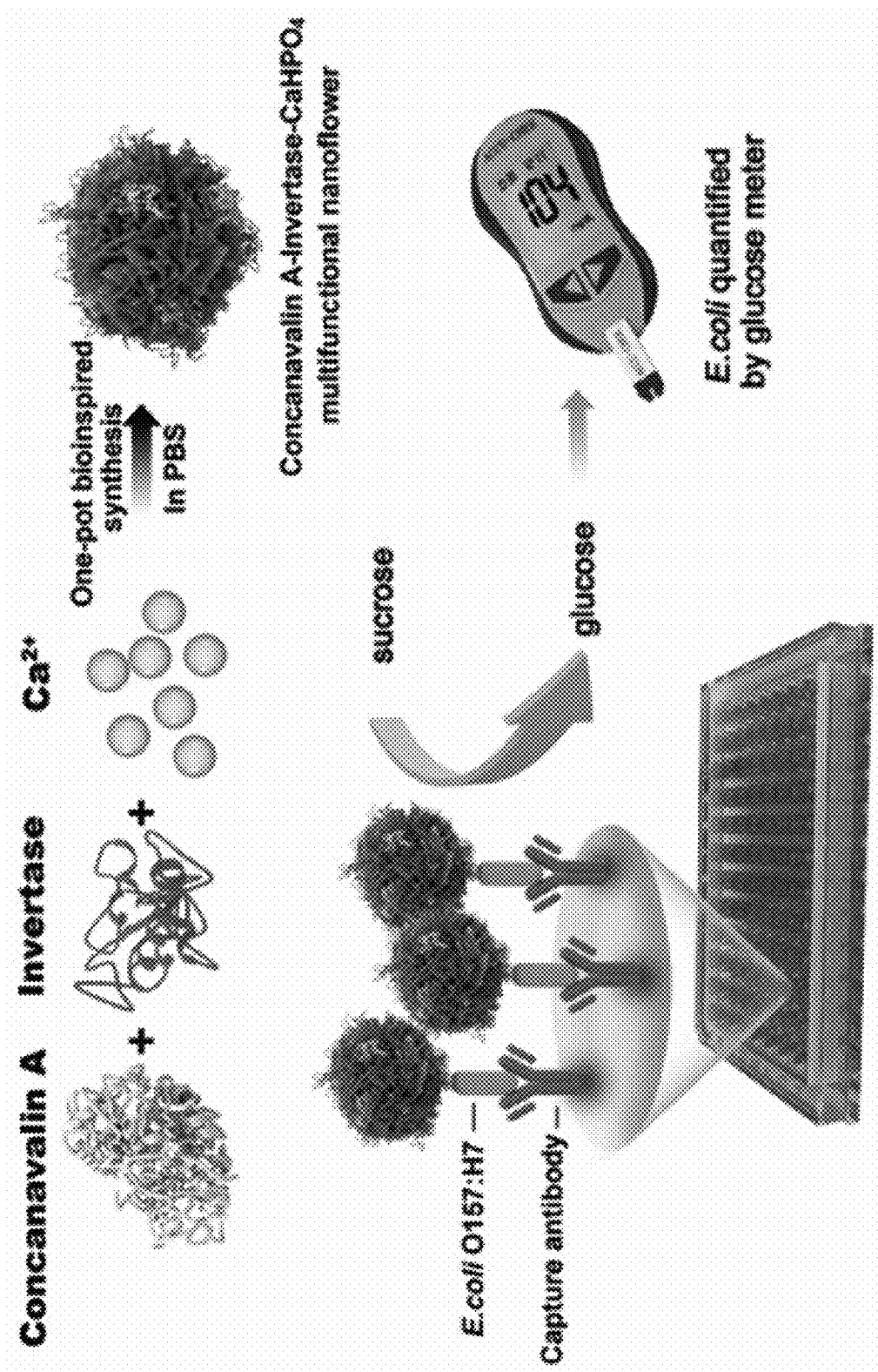
FIG. 26 schematically shows the synthetic process for Con A-invertase-$CaHPO_4$ nanoflowers and glucose meter-based portable immunoassay for detection of *E. coli* O157:H7.
Figure 27A:
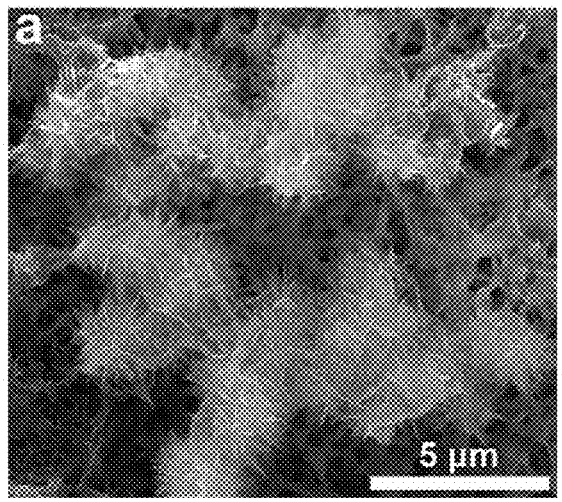
FIGS. 27A-27D: shown are SEM images image of CIC hybrid nanoflowers (FIG. 27A) and TEM images of CIC hybrid nanoflowers (FIGS. 27B and 27C). The XRD pattern of CIC hybrid nanoflowers with the corresponding JCPDS standard (JCPDS 72-0713) are also shown (FIG. 27D).
Figure 27B:
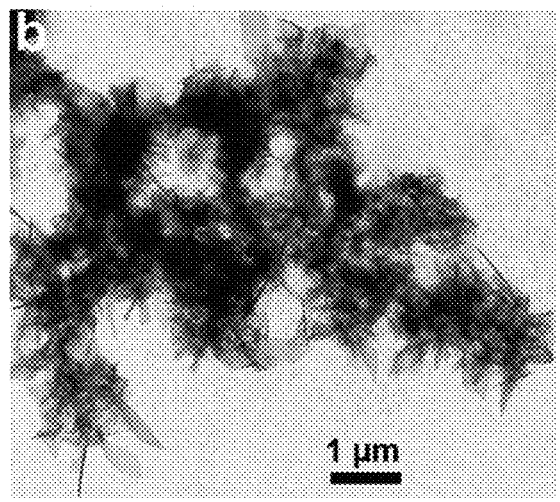
Figure 27C:
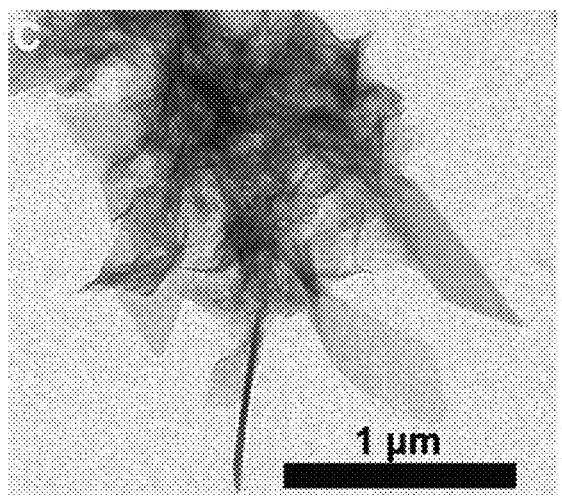
Figure 27D:
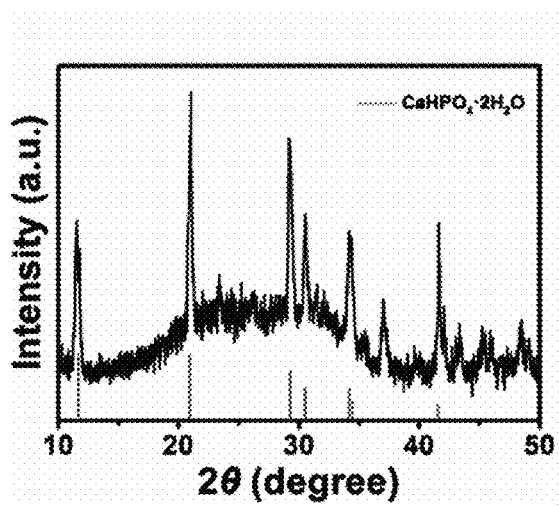
Figure 28A:
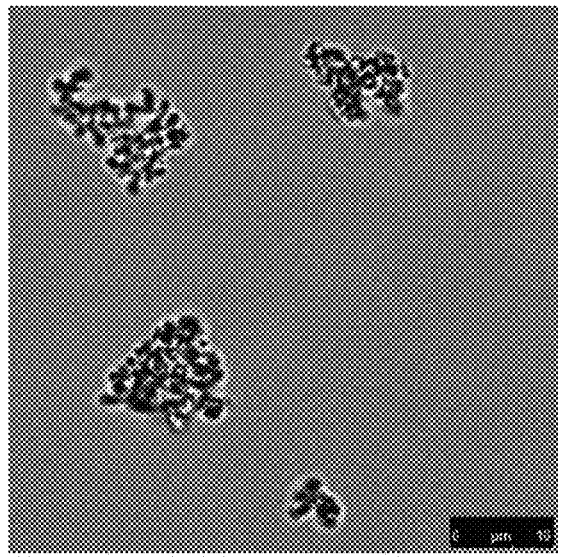
FIGS. 28A-28D illustrate observations of CIC hybrid nanoflowers using confocal fluorescence microscopy.
Figure 28B:
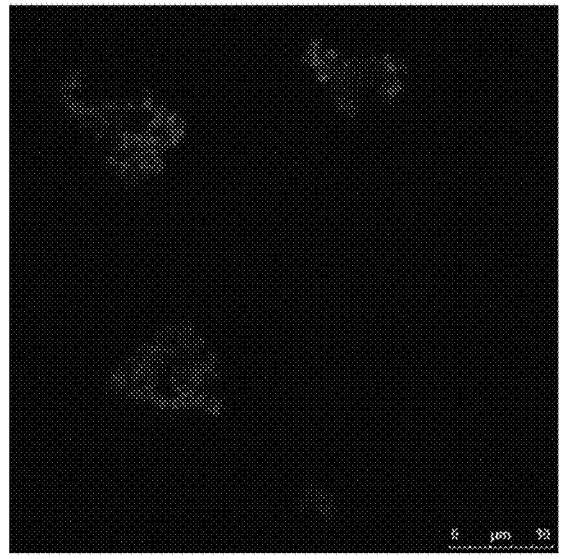
Figure 28C:
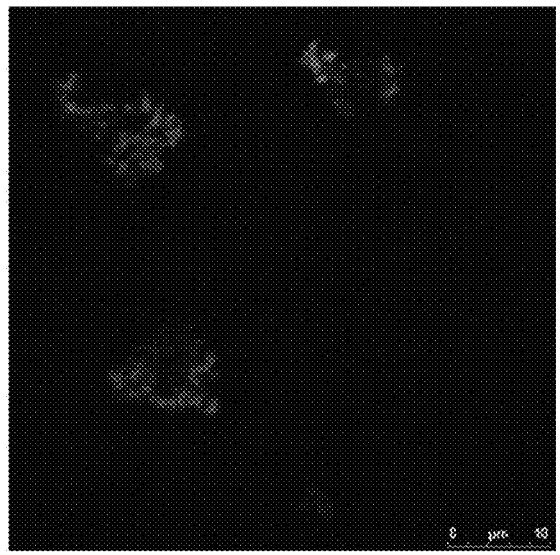
Figure 28D:
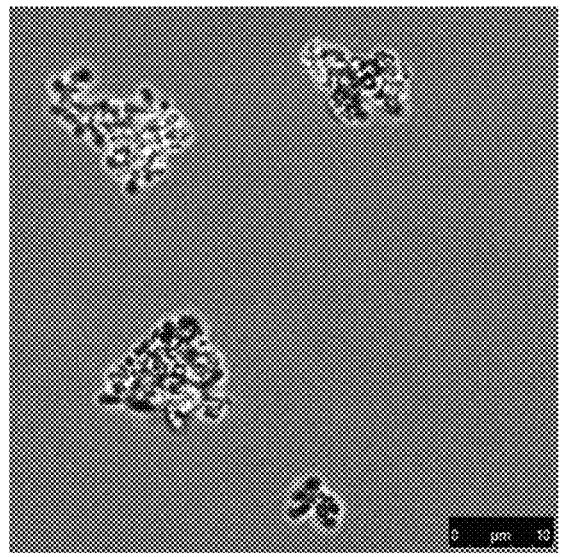
Figure 29A:
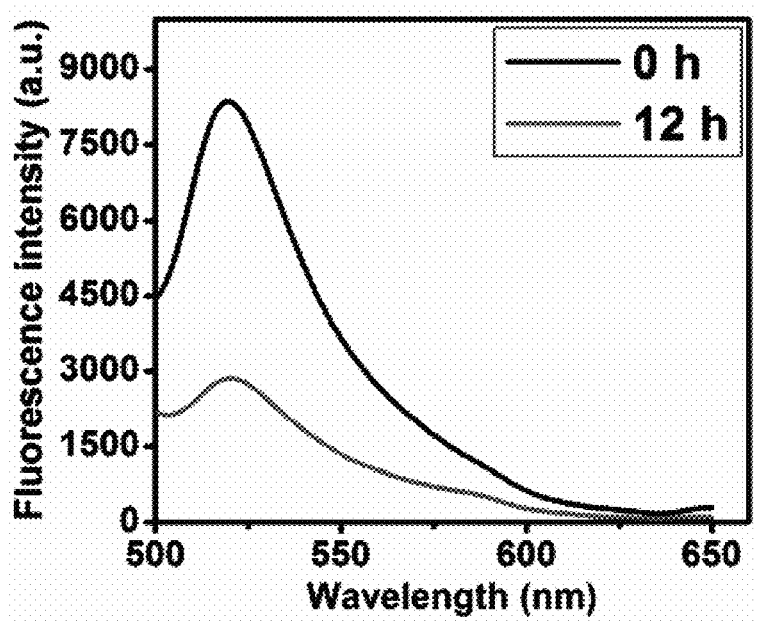
FIGS. 29A and 29B graphically represent fluorescence intensities of free Con A-FITC (FIG. 29A) and free invertase-Cy5 (FIG. 29B) in the supernatant at different reaction times.
Figure 29B:
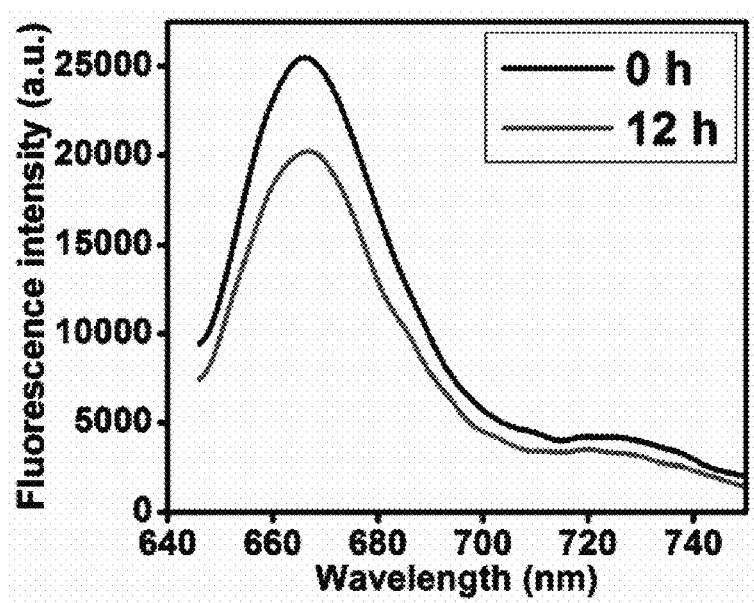

As illustrated by FIG. 26, this one-pot inspired process only involves the simple mixing of concanavalin A (Con A) and invertase with PBS solution containing calcium ions at room temperature. Con A-invertase-CaHPO$_4$ (CIC) nanoflowers have been synthesized successfully, employing this mild one-pot process. Compared with other nanomaterial-based carriers, the innovative features of the developed method include no extreme and harsh conditions, no toxic elements, and a simple purification processes, using only a one-step mild preparation, which significantly simplifies the synthetic process. The activity of the immobilized organic substances (Con A and invertase) can be effectively maintained due to less manipulation during preparation. CaHPO$_4$ supplies a biocompatible site for the immobilization of Con A and invertase. Moreover, several studies have proven that calcium ions can serve as an enhancer to increase the activity of invertase. Con A has high binding affinity to *E. coli* surface O-antigen and was used as the component for *E. coli* O157:H7 recognition. It is known that invertase can specifically hydrolyze sucrose to glucose. Accordingly, invertase serves as the signal output component in the protein-protein nanoflowers by correlation of the biorecognized *E. coli* O157:H7 with the concentration of hydrolyzed glucose, read by a portable personal glucose meter. Overall, the multifunctional protein-protein nanoflowers possess high biorecognition of the analyte and signal amplification by the enhanced enzymatic activity and stability, which are favorable for POC detection of *E. coli* O157:H7.

2. Methods 2.1 Materials and Chemicals

Invertase from baker's yeast, dibasic sodium phosphate ($Na_2HPO_4$), monobasic sodium phosphate ($NaH_2PO_4$), concanavalin A from *Canavalia ensiformis*, calcium chloride anhydrous ($CaCl_2$), and concanavalin A (FITC conjugate) were purchased from Sigma-Aldrich. *E. coli* O157:H7 monoclonal antibody was purchased from KPL Company. *E. coli* O157:H7, *Salmonella* and *Listeria monocytogenes* were provided by School of Food Science in Washington State University. *E. coli* K12 was provided by College of Life Science in Central China Normal University.

2.2 Synthesis and Characterization of Con A-Invertase-$CaHPO_4$ Nanoflowers

To synthesize Con A-Invertase-$CaHPO_4$ (CIC) hybrid nanoflowers, 0.02 mg Con A and 0.18 mg invertase were added to 3 mM PBS (1 mL, pH 6.8). Then, 20 μL 200 mM $CaCl_2$ was dissolved in the PBS solution. The mixture was placed at room temperature and allowed to react for 12 h. The products were obtained by centrifugation at 15000 rpm for 5 min and washing three times with DI water. The synthesized nanoflowers were dried on a filter membrane and then sputter-coated with gold for SEM observation. The synthesized nanoflowers were dried on a carbon grid for TEM observation. For confocal fluorescence microscopy imaging, the synthesized nanoflowers were dried on a glass slide for observation of the distribution of Con A FITC and invertase-Cy5 in CIC.

2.3 Preparation of Invertase-Cy5

Sulfo-cyanine5 NHS ester (Lumiprobe Corporation) was used to label invertase following the manufacturer's recommended protocol.

2.4 Loading Efficiency of Con A and Invertase in Nanoflowers

Due to the negligible molecular weight of FITC (389.39) and Cy5 (616.19) compared with Con A (26 kDa) and invertase (270 kDa), Con A-FITC and invertase-Cy5 were employed to replace the Con A and invertase for synthesizing CIC nanoflowers to determine the loading efficiency of Con A and invertase. A concentration series of 0, 0.001, 0.01, 0.015, and 0.025 mg Con A-FITC added to 1 mL PBS solutions (3 mM) was prepared to establish the calibration curve. 488 nm was used as the fluorescence excitation wavelength for FITC, and 525 nm was used as the fluorescence excitation wavelength for monitoring the fluorescence intensity of the solution with different concentrations. A concentration series of 0, 0.05, 0.1, 0.15, and 0.25 mg invertase-Cy5 added to 1 mL PBS solutions (3 mM) was prepared to establish the calibration curve. 646 nm was used as the fluorescence excitation wavelength for Cy5, and 670 nm was used as the fluorescence excitation wavelength for monitoring the fluorescence intensity of the solutions with different concentrations. The loading efficiency of Con A was calculated in the following manner: based on the calibration curve, 10 μL supernatant from a synthesis was used to measure the fluorescence intensity to calculate the amount of free Con A. The amount of immobilized Con A was defined as Ia=Ta−Fa. Ta stands for total amount of Con A added, and Fa stands for free Con A. Therefore, the loading efficiency of Con A was defined as (Ta−Fa)/Ta. The loading efficiency of invertase was calculated in the same manner.

2.5 Catalytic Studies

The catalytic ability of immobilized invertase and free invertase was calculated by an invertase activity assay kit, and enzyme activity assay was done according to the manufacturer's protocol. 0.05 μg $mL^{-1}$ of immobilized invertase and free invertase were used for all catalytic studies.

2.6 Procedure for Detection of *E. coli* O157:H7 Using Glucose Meter

The procedure for detection of *E. coli* O157:H7 was done according to traditional ELISA. PBST was used to wash 96-well plates three times after every step. Briefly, the 96-well plates were firstly coated with 200 ng $mL^{-1}$ *E. coli O*157: H7 monoclonal antibody (200 μL for each well) at 37° C. for 2 h. Then, the 96-well plates were blocked with 10 mg $mL^{-1}$ BSA (300 μL for each well) at 37° C. for 1 h. Then the antibody-coated plates were stored at 4° C. until use.

To detect *E. coli* O157:H7, standard solutions with different concentrations of *E. coli* O157:H7 or milk samples were incubated in the plate at 37° C. for 1 h. Next, after diluting 10 times, 100 μL synthesized CIC was added to each well at 37° C., incubating for 25 min. After washing three times with PBST and three times with DI water, 100 μL sucrose solution (500 mM, pH 4.5) was added to each well, and the plate was placed at 55° C. for 30 min. Finally, the concentration of glucose produced in each well was determined by the glucose meter.

2.7 Instruments

A glucose meter (ACCU-CHEK Avia) was used to determine the concentration of glucose. SEM images were obtained by a FEI Sirion field emission scanning electron microscope. TEM images were collected by a Philips CM200 UT (Field Emission Instruments, USA). A Rigaku Miniflex 600 was used to perform XRD analysis. Fluorescence images and fluorescence spectra were obtained using a Leica Microsystems Inc. (IL, USA) confocal fluorescence microscope and TECAN multifunctional microplate reader, respectively.

3. Results and Discussion 3.1 Characterization of CIC Hybrid Nanoflowers

Scanning electron microscope (SEM) and transmission electron microscope (TEM) images were obtained to demonstrate the morphology of the CIC hybrid nanoflowers. The SEM image showed the flower-like nanostructure of as-prepared CIC products with a size of ~2 μm (FIG. 27A). This flower structure morphology of CIC is also shown in the TEM image (FIG. 27B). Further observation of the CIC hybrid nanoflowers exhibited nanosheet structures in the petal-like sections (FIG. 27C). The diffraction peaks in X-ray diffraction (XRD) analysis fitted well with $CaHPO_4.2H_2O$ (JCPDS 72-0713) (FIG. 27D), confirming the inorganic component in the hybrid nanoflowers. Moreover, the energy-dispersive X-ray spectroscopy (EDS) analysis also agreed well with $CaHPO_4.2H_2O$ (not shown).

3.2 Encapsulation of Con A and Invertase in the Hybrid Nanoflowers

To confirm that Con A and invertase were successfully immobilized in the CIC hybrid nanoflowers, Con A and invertase were fluorescently labeled with FITC and Cy5, respectively. As expected, FITC-labeled Con A, Cy5-labeled invertase, and their distribution in the CIC was clearly observed by fluorescence confocal microscopy (FIGS. 28A-28D). Meanwhile, the fluorescence intensity of free Con A-FITC and invertase-Cy5 in the supernatant obviously decreased after reaction for 12 h (FIGS. 29A and 29B). These results indicated that Con A and invertase were successfully immobilized in the hybrid nanoflowers. Subsequently, we calculated the loading efficiency of Con A and invertase for determining the amount of Con A and invertase immobilized in CIC. With the optimized 1:9 ratio of Con A:invertase for the preparation of CIC, the loading efficiency of Con A and invertase in the hybrid nanoflowers were calculated to be 80.3% and 27.7%, respectively. Accordingly, the green facile approach afforded a reliable, promising way for the facile synthesis of protein-protein conjugates.

3.3 CIC Catalytic Studies

Figure 30A:
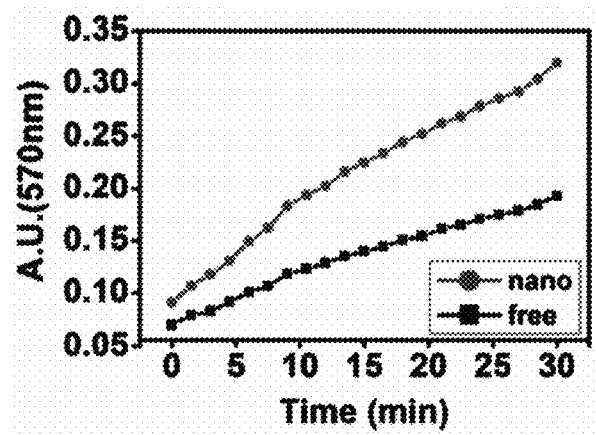
FIGS. 30A-30C graphically illustrate the kinetics of activity of immobilized invertase in CIC nanoflowers and free invertase (FIG. 30A); storage stabilities of immobilized invertase in CIC hybrid nanoflowers and free invertase in PBS at room temperature (FIG. 30B); and stability of CIC hybrid nanoflowers for detection of *E. coli* O157:H7 ($10^3$ CFU mL$^{-1}$) within 30 days (FIG. 30C).
Figure 30B:
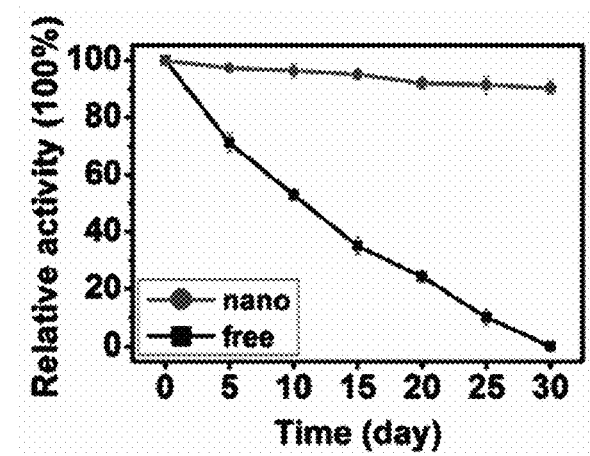
Figure 30C:
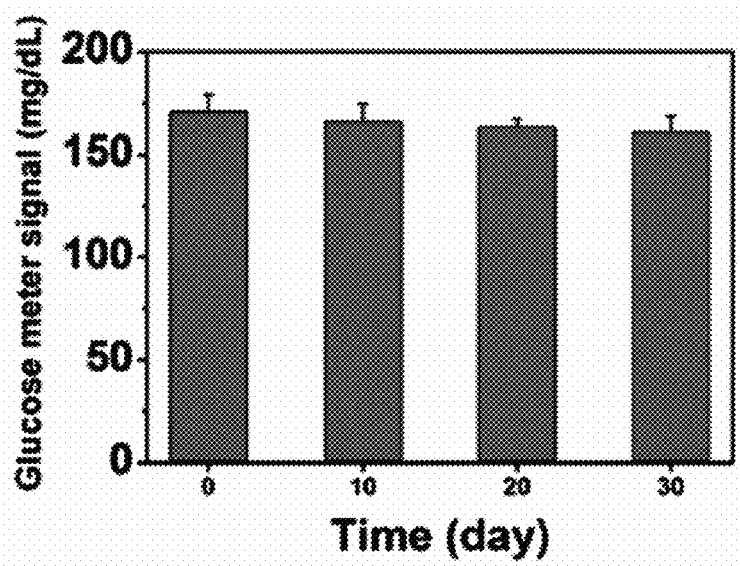

In developing enzyme-based signal labels, the core issue is to simultaneously immobilize a large amount of enzymes while maintaining the enzymatic activity of protein-protein conjugates. Previous results confirmed that CIC hybrid nanoflowers can load a relatively high amount of invertase. The catalytic activity of immobilized invertase and free invertase was then studied and compared. The activities of free invertase and invertase immobilized in the CIC nanoflowers were 7.40 U $mL^{-1}$ and 15.06 U $mL^{-1}$, respectively (FIG. 30A). Previous studies have shown that $Cu^{2+}$ and $Ca^{2+}$ can obviously improve the activity of laccase and α-amylase, respectively, in the corresponding organic-inorganic hybrid nanoflowers (see Ge, J., et al., Nat. Nanotechnol., 2012, 7, 428-432; Wang, L. B., et al., J. Am. Chem. Soc., 2013, 135, 1272-1275). Similarly, we found that there was a 203.5% increase in activity of immobilized invertase in CIC nanoflowers, demonstrating that $Ca^{2+}$ is a good activity enhancer for immobilized invertase in CIC nanoflowers. Moreover, invertase immobilized in the CIC nanoflowers is more stable than free invertase. The free invertase lost all of its initial activity after 30 days of storage in PBS (pH 6.8). In contrast, the invertase immobilized in CIC nanoflowers kept >90% of their initial activity under the same conditions (FIG. 30B). In addition, as shown in FIG. 30C, there was no significant glucose signal change after 30 days of storage, which indicates that Con A in the hybrid nanoflowers still maintained relatively high activity without losing its binding ability during storage. Thus, the obtained all-inclusive CIC hybrid nanoflowers simultaneously realized sufficient invertase loading and good maintenance of the activity of immobilized invertase, which meets the requirements of signal labels for bioassays with enzyme-based signal amplification strategies.

3.4 Optimization for Immunoassay

Figure 31A:
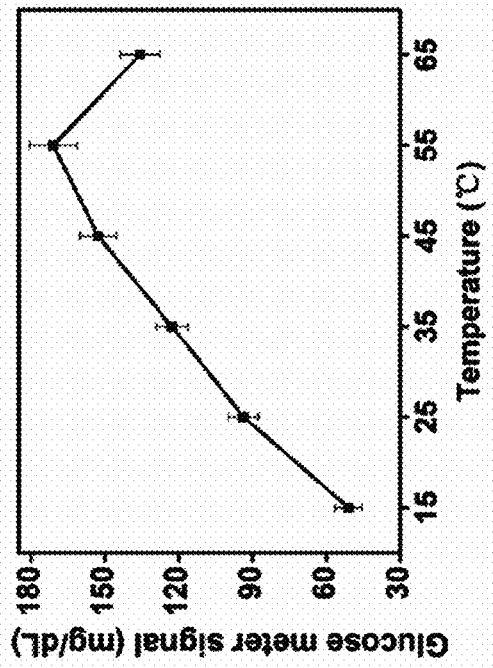
FIGS. 31A-31D illustrate the detection of *E. coli* O157:H7 with different mass ratios between Con A and invertase using a glucose meter (FIG. 31A), at different temperatures (FIG. 31B), pH values (FIG. 31C), and reaction times for CIC to catalyze sucrose (FIG. 31D).
Figure 31B:
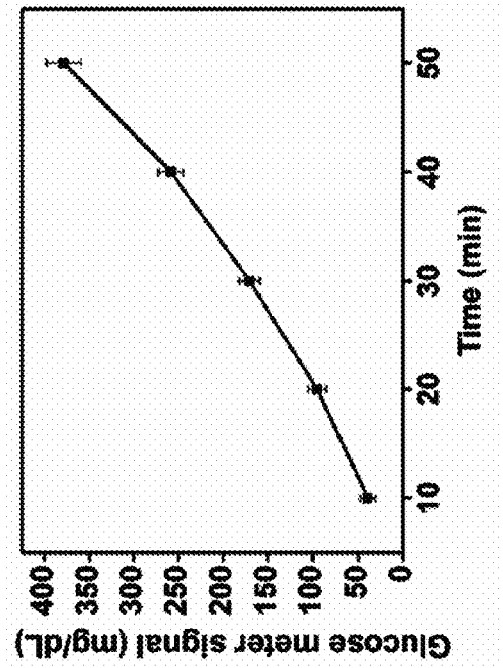
Figure 31C:
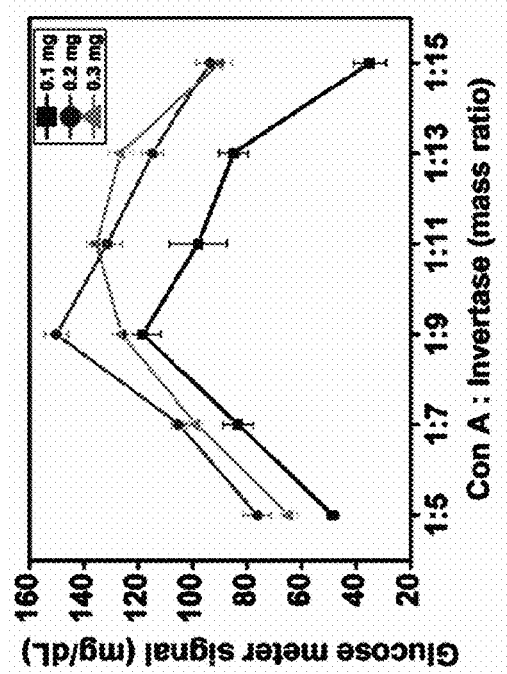
Figure 31D:
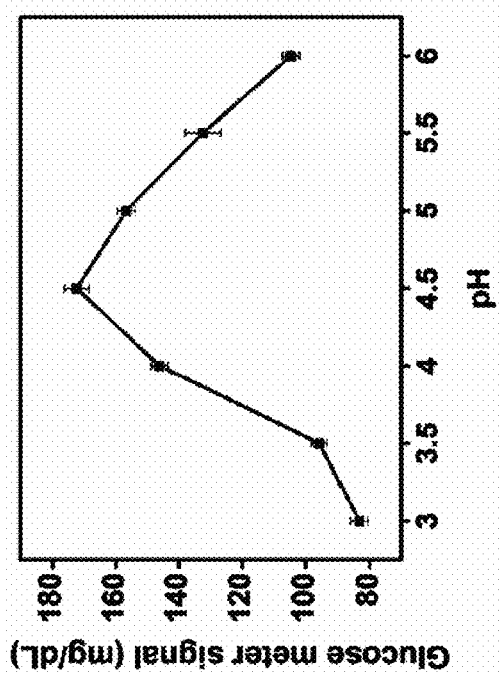

The detection conditions should be optimized for best immunoassay performance. Firstly, the effect of feeding mass ratio between Con A and invertase was studied. The recognition efficiency between CIC and E. coli O157:H7 was influenced by the loading amount of immobilized Con A. The glucose signal was directly determined by the amount of immobilized invertase in hybrid nanoflowers. Therefore, organic components with different mass feeding ratios between Con A and invertase played an important role in detecting E. coli O157:H7. The maximum glucose signal was obtained with the ratio of 1:9 between Con A and invertase for the total organic component (0.2 mg), as shown in FIG. 31A, which were used as the optimized parameters for further measurements. Besides, the effects of temperature, pH value and reaction time were investigated. As shown in FIGS. 31B and 31C, the highest glucose signal was obtained at 55° C. and pH 4.5. Therefore, 55° C. was chosen as the optimized reaction temperature, and pH 4.5 was used as the optimized pH of the sucrose solution. In addition, reaction time with sucrose catalyzed by CIC was also optimized. As shown in FIG. 31D, there was a detectable signal after 10 min, and the amount of glucose produced increased with the reaction time. To ensure a detectable signal for E. coli O157:H7, we chose 30 min as the optimized reaction time.

3.5 Detection of E. coli O157:H7

Figure 32:
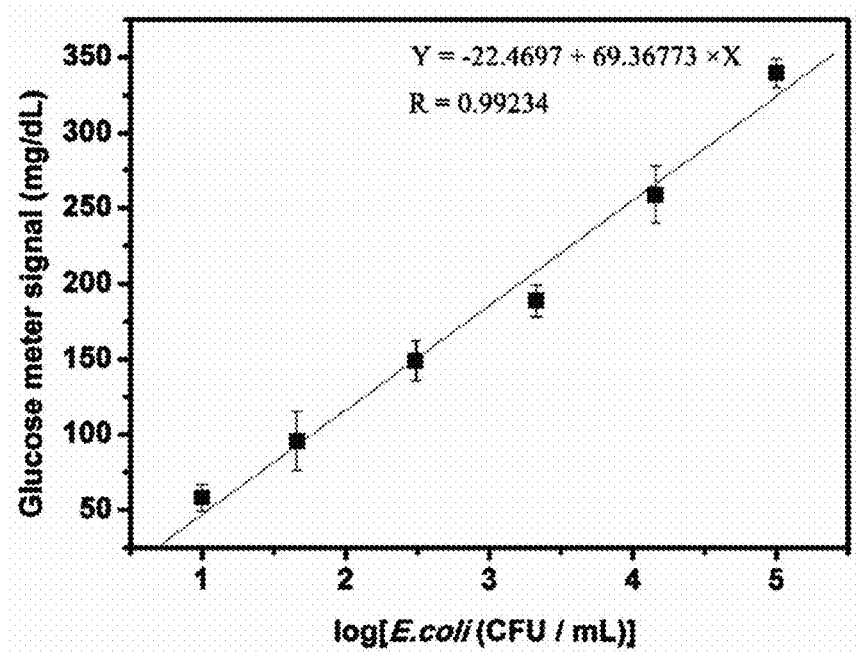
FIG. 32 graphically illustrates the calibration curve for detection of *E. coli* O157:H7 at different concentrations using glucose meter. *E. coli* O157:H7 samples were diluted in PBS.
Figure 33:
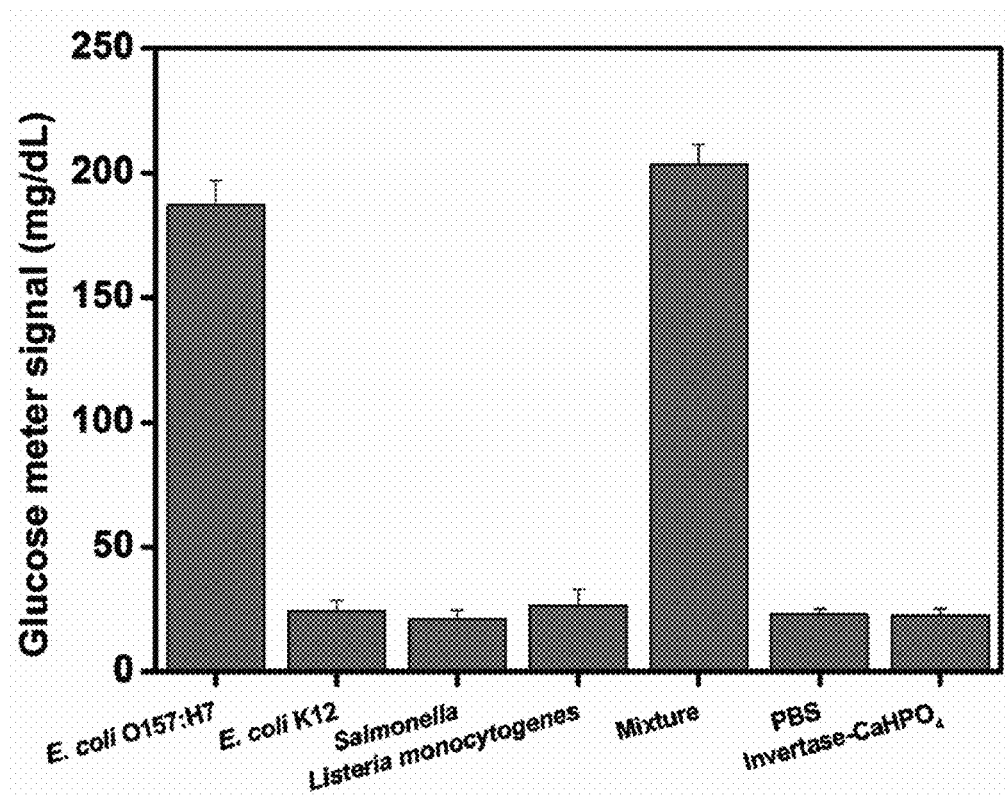
FIG. 33 graphically illustrates the selectivity of the developed method (all bacterial samples were used at concentration of $1\times10^3$ CFU mL$^{-1}$). Mixture: *E. coli* O157:H7, *E. coli* K12, *Salmonella, L. monocytogenes* were mixed at 1:1:1:1.

As depicted in FIG. 26, the detection of E. coli O157:H7 was based on sandwich-type immunoassay. The CIC nanoflowers, as signal tags, played crucial roles in the portable detection of E. coli O157:H7. Firstly, recognition between E. coli O157:H7 and CIC nanoflowers was accomplished by Con A, which could specifically bind to the surface O-antigen of E. coli. Secondly, the amplified signal output was achieved by invertase catalyzing sucrose to glucose, which could be read reliably by a personal glucose meter. Thirdly, the inorganic component of dicalcium phosphate in CIC nanoflowers was responsible for immobilizing the massive Con A and invertase. When CIC hybrid nanoflowers bind to the E. coli O157:H7, glucose is produced after adding the sucrose solution. Therefore, with the portable glucose meter, the linear relationship between the concentration of glucose produced and concentration of E. coli O157:H7 was established. As compared with other methods (TABLE 10), the developed immunosensors exhibit excellent performance for detecting E. coli O157:H7, with the detection sensitivity of $10^1$ CFU $mL^{-1}$, in the linear range of $10^1$ to $10^5$ CFU $mL^{-1}$ (FIG. 32). In addition, E. coli K12, Salmonella and Listeria monocytogenes were used as non-target bacteria to evaluate the selectivity of the present method. Significant glucose signal was yielded in detecting E. coli O157:H7, while very low glucose signals were produced for other non-target bacteria (FIG. 33). Obviously, this method has adequate selectivity. We also synthesized invertase-$CaHPO_4$ hybrid nanoflowers as the control without Con A for E. coli O157:H7 detection. The glucose signal generated was very weak when using invertase-$CaHPO_4$ hybrid nanoflowers as probes, similar to the blank control (PBS) (FIG. 33). This result confirmed that Con A has its recognition area on the surface of nanoflowers to bind to E. coli. For recovery study, milk was obtained without any pretreatment from a local supermarket. E. coli O157:H7 was diluted in the milk at the concentration of $1\times10^2$, $1\times10^3$, and $1\times10^4$ CFU $mL^{-1}$, then 100 μL spiked milk samples were loaded on the ELISA 96-well plate for analysis. Milk sample without spiked E. coli O157:H7 was used as the control. The concentration of E. coli O157:H7 in the milk was determined by the obtained standard curve. Recoveries of E. coli O157:H7 ranged from 93.3±4.4% to 106.6±2.6% (TABLE 11). These results successfully proved the feasibility and reliability of the proposed method, which could be applied for food sample detection.

TABLE 10

Comparison of different methods for E. coli O157:H7 detection

| Methods | Microorganism | Linear range (CFU mL$^{-1}$) | $^b$LOD (CFU mL$^{-1}$) | Total detection time | Ref. |
|---|---|---|---|---|---|
| Isotachophoresis | E. coli O157:H7 | $10^2$-$10^6$ | $10^3$ | 1 h | Borysiak, M. D., et al., Lab Chip, 2015, 15, 1697-1707 |
| Quartz crystal microbalance | E. coli O157:H7 | 0-2.0 × $10^3$ | 400 | 10 min | Dong, Z. M. and G. C. Zhao, Talanta, 2015, 137, 55-61 |
| Lateral flow immunoassay | E. coli O157:H7 | 102-$10^8$ | $10^2$ | 20 min | Jiang, T., et al., Biosens. Bioelectron., 2016, 77, 687-694 |
| $^a$FNP-ELISA | E. coli O157:H7 | 6.8 × $10^2$-6.8 × $10^3$ | 68 | 1 h 50 min | Shen, Z. Q., et al., Gut Pathog., 2014, 6, 14 |
| Chemiluminescence immunoassay | E. coli O157:H7 | 4.3 × $10^3$-4.3 × $10^5$ | 1.2 × $10^3$ | 1 h 50 min | Zhag, Y., et al., Anal. Chem., 2014, 86, 1115-1122 |
| This method | E. coli O157:H7 | 10-$10^5$ | 10 | 1 h 55 min | This work |

$^a$Functional nanoparticle.
$^b$Limit of detection.

TABLE 11

Recoveries of E. coli O157:H7-spiked samples

| Original value (CFU mL$^{-1}$) | E. coli added (CFU mL$^{-1}$) | E. coli found (CFU mL$^{-1}$) | Recovery (%) |
|---|---|---|---|
| 0 | 1 × $10^2$ | (1.06 ± 0.026) × $10^2$ | 106.6 ± 2.6 |
| 0 | 1 × $10^3$ | (0.933 ± 0.044) × $10^3$ | 93.3 ± 4.4 |
| 0 | 1 × $10^4$ | (0.955 ± 0.056) × $10^4$ | 95.5 ± 5.6 |

4. Conclusion

In summary, we presented a facile one-pot process to prepare all-inclusive CIC hybrid nanoflowers with all the necessary functions of biological recognition and signal amplification for immunoassay labels. The application of this kind of protein-protein conjugate, used as signal tags for point-of-care detection of E. coli O157:H7, has also been demonstrated. As expected, this approach can be generally employed to prepare a variety of protein-protein conjugates for various applications, which will make good contributions for pushing the frontier of current research forward in areas such as organic-inorganic hybrid materials, interface and colloid science, molecular recognition, enzyme engineering, analytical sciences, material science and engineering, and biomedical engineering.

Example 6

This Example describes a bioinspired synthesis of all-in-one organic-inorganic hybrid nanoflowers combined with a handheld pH meter for on-site detection of food pathogen.

1. Introduction, Results, and Discussion

Biosensors have received significant investigative attention due to their broad fascinating applications, ranging from biomedical diagnosis to drug screening, food safety and quality control, and environmental monitoring. Vast endeavors have been undertaken to develop various strategies for realizing biosensing goals in a sensitive, selective, speedy, automatic, and accurate manner. In fact, considerable efforts have been attempted to improve the sensitivity of biosensors. The most popular bioassay type, sandwich biosensing relies on a specific biorecognition of model analytes using recognition probes and then transduces and amplifies the signal change of the biorecognition through signal probes. Therefore, achieving new signal amplification strategies becomes one of the core tasks in the development of highly sensitive biosensors. Due to the advantages of high reactivity, selectivity, and specificity toward the substrate and affording readout signals, enzyme-based signal amplification becomes the most commonly used technique for bioassays (such as enzyme linked immunosorbent assay (ELISA) and Western blot). Many contributions have been performed to develop enzyme-based signal probes. The key is to load a large amount of enzymes and simultaneously maintain the enzyme activity. To date, considerable efforts have been made to explore ideal nanoparticles for enzyme immobilization. There are often two ways to immobilize enzymes by nanoparticles: one is physical adsorption and the other is chemical covalent immobilization. For physical immobilization, the easy leaching of the enzyme remains an obstacle. For chemical immobilization, the complicated immobilization process and necessary chemical immobilization reaction result in activity loss for the immobilized enzymes. Recently, a new type of organic-inorganic hybrid nanoflower was prepared using a mild bioinspired method similar to biomineralization. Using enzymes as the organic component, the enzyme-inorganic hybrid nanoflowers exhibited enhanced catalytic activity, stability, and durability. This bioinspired strategy of creating protein-inorganic nanoflowers has provided us with the blueprint of other hybrid systems. According to recent developments, the protein-inorganic nanoflowers can be a promising tool in biomedical fields and biocatalytical processes. However, current studies have been restricted to only one type of protein-enzyme. Naturally, we believe that it is possible to prepare a new type of signal tag integrating a biorecognition unit (recognition protein) as the second protein component into the enzyme-inorganic hybrid nanoflowers. Toward this end, a new bioinspired strategy was proposed to prepare an all-in-one organic-inorganic nanoflower integrating biorecognition unit, signal amplification unit, and carrier unit within a one pot reaction for the portable sensitive detection of a food pathogen: Escherichia coli (E. coli) O157:H7.

Figure 34:
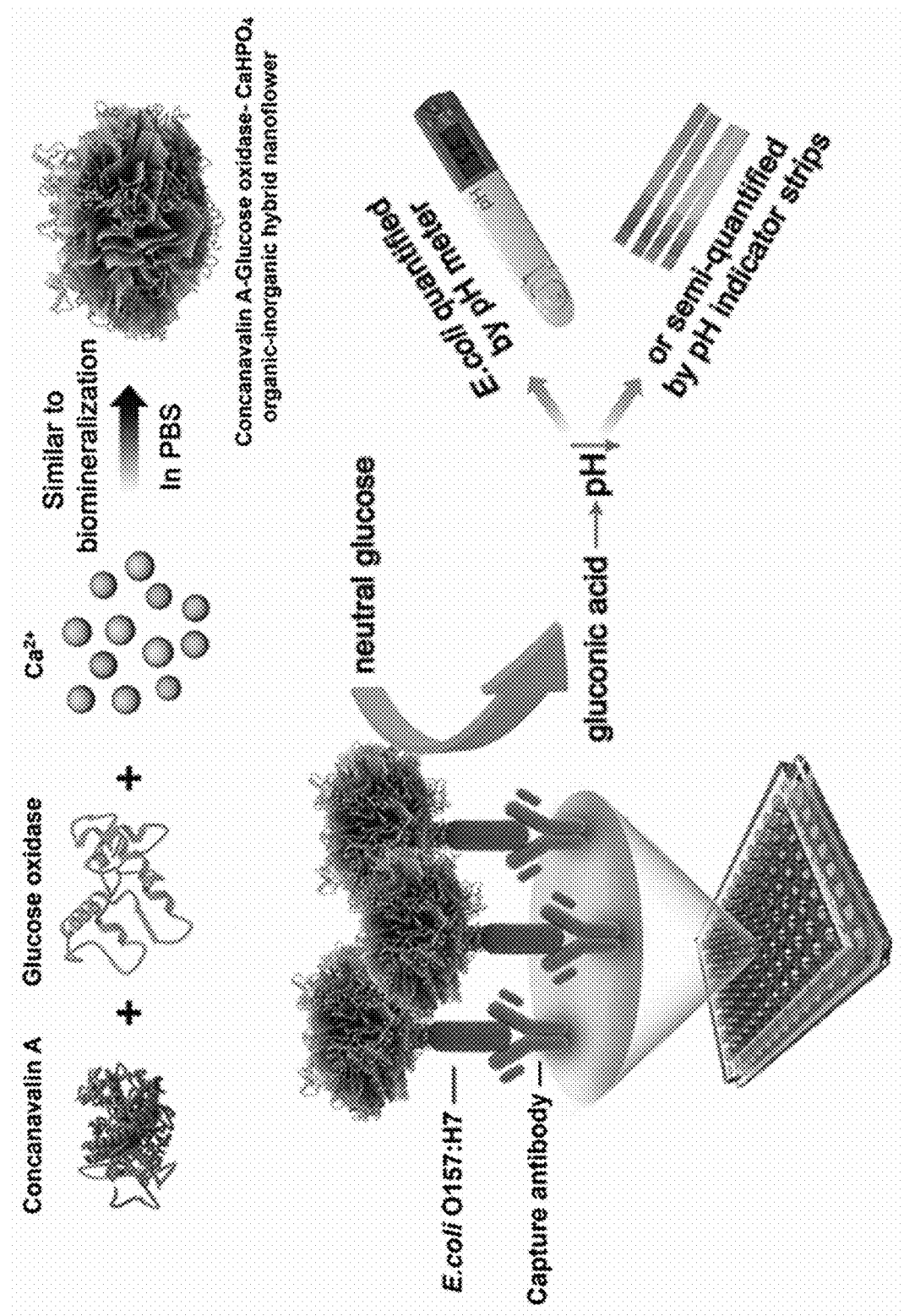
FIG. 34 schematically illustrates and exemplary synthetic process for Con A-GOx-CaHPO$_4$ organic-inorganic hybrid nanoflowers and the corresponding scheme for immunoassay of *E. coli* O157:H7.

As indicated in FIG. 34 and inspired by the biomineralization process, concanavalin A (Con A) and glucose oxidase (GOx) are placed into a calcium ion solution for a given time at room temperature. Using this mild one-pot process, Con A-GOx-CaHPO$_4$ (CGC) nanoflowers have now been prepared successfully. Biocompatible CaHPO$_4$ plays a critical role in the immobilization of Con A and GOx. It is notable to observe that this approach does not require any toxic elements, extreme harsh conditions, or complicated purification processes. Therefore, the organic substance (Con A and GOx) involved in the preparation is subjected to less manipulation compared to other conventional methods to maintain the activity of the immobilized recognition protein and enzyme. Con A was selected as the recognition unit due to its high affinity to lipopolysaccharides O-antigen of *E. coli*, which has been used for the sensitive detection of *E. coli* O157:H7. Specifically, GOx can efficiently convert glucose to gluconic acid resulting in a decrease in the pH. GOx serves as the signal amplification unit and correlates the biorecognition process of *E. coli* O157:H7 with the corresponding change in pH revealed by a portable pH meter or a pH indicator strip. It is noted that the introduction of Con A and GOx rendered the nanoflowers to possess a dual functions: the specific capture ability toward the corresponding analyst and the enhanced enzymatic activity and stability for producing signal amplification. Therefore, a simple but potentially powerful amplification biosensing technology with excellent simplicity, portability, sensitivity, and adaptability was developed based on the prepared all-in-one CGC organic-inorganic hybrid nanoflowers.

Figure 35A:
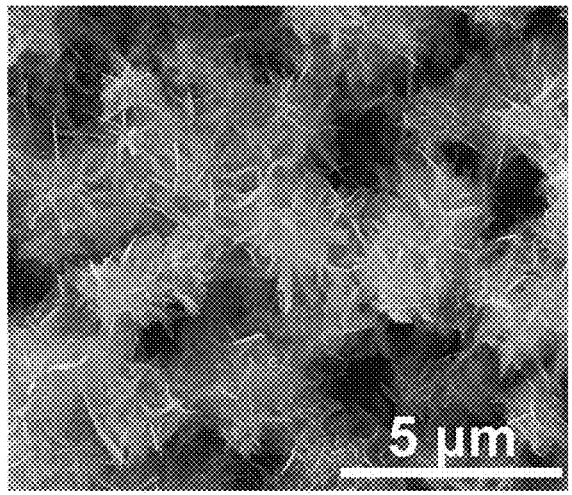
FIGS. 35A-35D.
Figure 35B:
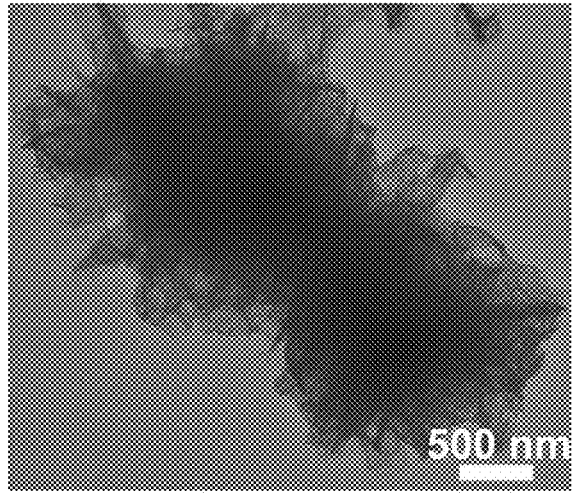
Figure 35C:
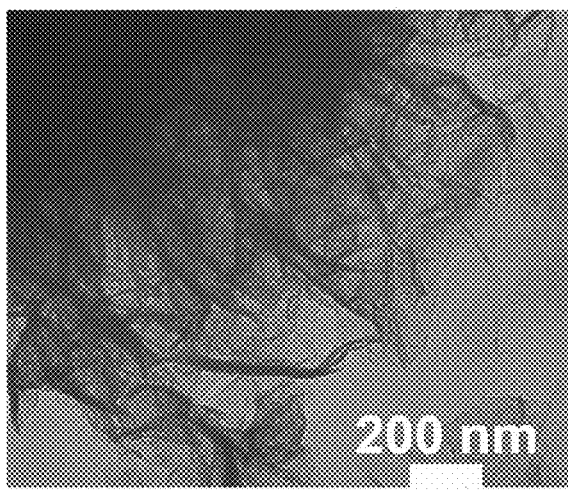
Figure 35D:
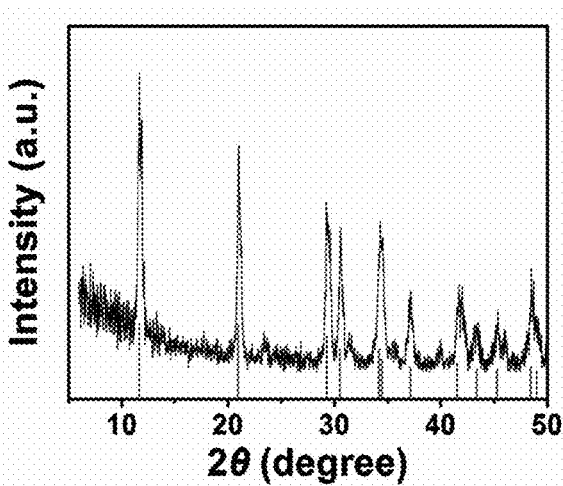
Figure 36A:
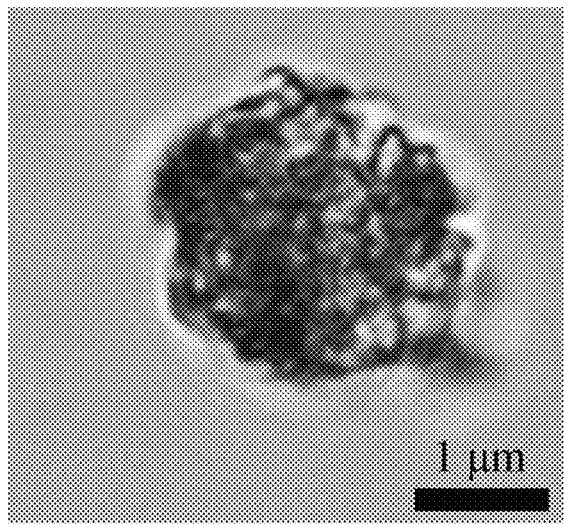
FIGS. 36A-36D illustrates confocal fluorescence microscopy images of Con A-GOx-CaHPO$_4$ hybrid nanoflowers.
Figure 36B:
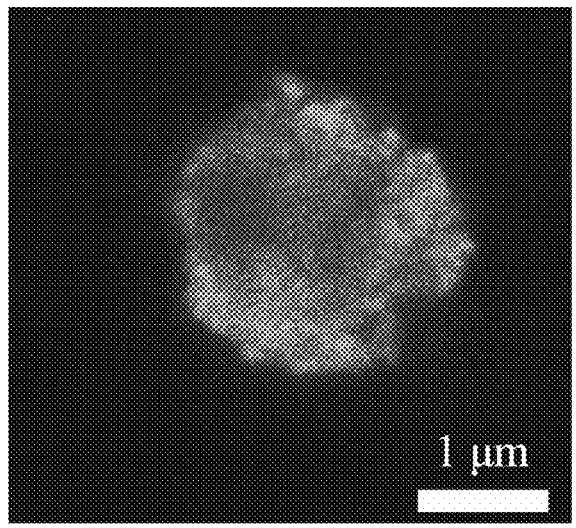
Figure 36C:
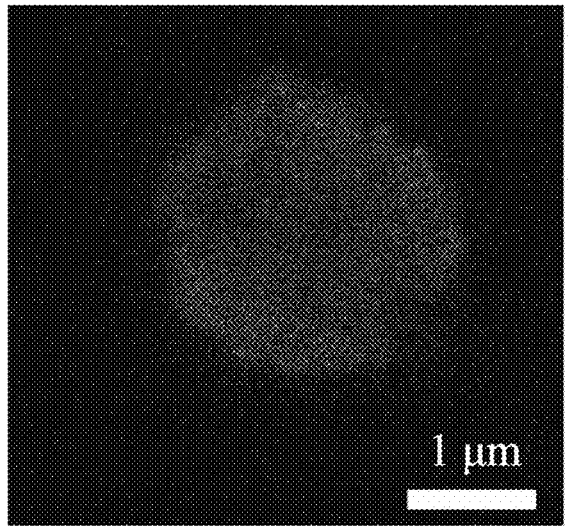
Figure 36D:
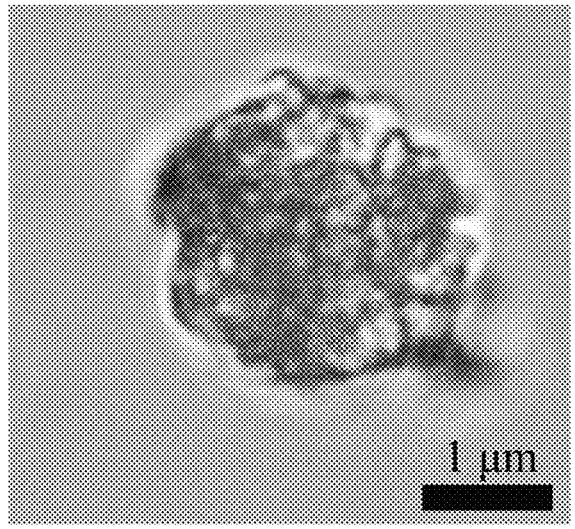

To investigate the morphology of this hybrid, scanning electron microscope (SEM) and transmission electron microscope (TEM) images were collected. As illustrated by the SEM image in FIG. 35A, the CGC hybrid products showed the flower-like nanostructure with an average size of ≈2±0.5 μm. The TEM image further revealed the flower morphology with a petal-like structure (FIG. 35B). Close observation of the structure of the CGC hybrid suggested that the petal-like sections with a light color were composed of nanosheet structures (FIG. 35C). An X-ray powder diffraction (XRD) analysis was performed to illustrate the inorganic component of the CGC hybrid nanoflowers (FIG. 35D). All of the diffraction peaks agreed well with the feature peaks of $CaHPO_4 \cdot 2H_2O$ (JCPDS 72-0713). Energy dispersive X-ray spectroscopy data were also in accord with the component of $CaHPO_4 \cdot 2H_2O$ (not shown).

To verify that GOx and Con A were both immobilized on the hybrid nanoflowers, GOx and Con A were fluorescently labelled with Cyanine5 (Cy5) and Fluorescein isothiocyanate (FITC), respectively, to prepare the CGC nanoflowers. The red dots and green dots in the fluorescence confocal microscopy images represented the distribution of the Cy5 labelled GOx and FITC labelled Con A, respectively, in the hybrid nanoflowers (FIGS. 36A-36D). These results revealed the successful immobilization of GOx and Con A in the CGC hybrid nanoflowers. Besides, we did two experiments to confirm that the immobilized Con A molecules have binding site exposed on the surface of the nanoflowers indirectly. For the first experiment, we prepared GOx-$CaHPO_4$ hybrid nanoflowers without Con A as the control probes for detecting *E. coli* O157:H7. No significant pH change was observed using the GOx-$CaHPO_4$ hybrid nanoflowers as probes to detect *E. coli* O157:H7 (not shown). On the contrary, there was significant pH change by using ConA-GOx-$CaHPO_4$ hybrid nanoflowers as signal labels. This result revealed that the immobilized Con A molecules could recognize *E. coli* O157:H7, which indirectly proved that the immobilized Con A molecules have its binding site exposed on the surface of the ConA-GOx-$CaHPO_4$ hybrid nanoflowers. For the second one, the Con A can bind to horseradish peroxidase (HRP) as a glycoprotein and then catalyze the conversion of chromogenic substrate 3,3',5,5'-tetramethylbenzidine (TMB) into blue products in the presence of hydrogen peroxide (see Paradkar, V. M., et al., Biotechnol. Prog. 1991, 7, 330). We prepared ConA-GOx-$CaHPO_4$ hybrid nanoflowers and GOx-$NaH_2PO_4$ hybrid nanoflowers for possible binding to HRP. ConA-GOx-$CaHPO_4$ hybrid nanoflowers catalyzed TMB into obvious dark blue products in the presence of hydrogen peroxide, while only producing a slight color change for GOx-$CaHPO_4$ hybrid nanoflowers (not shown). This may due to the nonspecific adsorption of HRP on the GOx-$CaHPO_4$. This result further indirectly confirmed that Con A molecules have its binding site exposed on the surface of the ConA-GOx-$CaHPO_4$ hybrid nanoflowers. Accordingly, with a 12:1 mass feeding ratio of GOx:Con A, the immobilization efficiency of GOx and Con A in the CGC nanoflowers was calculated to be 52.2% and 80.6%, respectively. This result indicated that the bioinspired approach afforded a facile way for the efficient immobilization of the biorecognition protein and enzyme, which holds great potential for biomedical applications.

For enzyme-based signal amplification strategies in bioassays, the key is to load a large amount of enzymes and simultaneously maintain the enzyme activity. Previous results confirmed that the bioinspired approach allowed to immobilize a relatively high amount of GOx. Then, the activity of the immobilized GOx in the CGC nanoflowers was carefully investigated and the result was depicted in FIG. 37A. The activity of the immobilized GOx in the CGC nanoflowers and the free GOx was calculated to be 8.93 and 11.55 U $mL^{-1}$, respectively. Previous studies demonstrated that an α-amylase hybrid nanoflower and a laccase hybrid nanoflower exhibited enhanced enzymatic activity with the help of $Cu^{2+}$ and $Ca^{2+}$ activators in $Cu_3(PO_4)_2$ and $CaHPO_4$, respectively (see Ge, J., et al., Nat. Nanotechnol. 2012, 7, 428; Wang, L. B., et al., J. Am. Chem. Soc. 2013, 135, 1272). However, the GOx does not require any metal ion activators; thus, there is a slight decrease in the enzymatic activity may due to the mass-transfer limitations in the solid supports. Although there is 22.7% decrease in the activity of the immobilized GOx, the storage stability of the immobilized GOx in the CGC nanoflowers has improved significantly compared with that of the free GOx. As depicted in FIG. 37B, the free GOx lost more than 70% of its initial activity when it was stored in a phosphate buffered saline (PBS) solution (pH 6.8) at room temperature after one month, whereas the immobilized GOx in the CGC nanoflowers retained most of its initial activity (>90%) under the same conditions. Furthermore, as shown in FIG. 37C, after 30 d storage, there was no significant pH value change, which indicated that Con A still maintained high activity in the hybrid nanoflowers, and the CGC hybrid nanoflowers could be used without losing binding ability. These may be attributed to the biocompatible interface for the GOx immobilization rendered by the biocompatible $CaHPO_4$.

As depicted by FIG. 34, the readout signal was generated by the resulting decrease in the pH originating from the GOx-catalysis of glucose into gluconic acid after the sandwich immunoreaction of *E. coli* O157:H7. GOx can oxidize glucose into gluconic acid and $2H_2O_2$ with the help of oxygen. One challenge in the detection is that the generated $2H_2O_2$ will inhibit the activity of the GOx. To enhance the catalytic reaction rate and reduce the reaction time, catalase was also added to the glucose solution to remove $2H_2O_2$. The reaction time was reduced by half with the addition of catalase. Thereafter, to achieve a good detection performance of *E. coli* O157:H7, the detection conditions were optimized. The optimal conditions were determined as follows: 0.3 mg of organic components with a mass ratio of 1:12 for Con A:GOx, 35° C. as the reaction temperature and 90 min as the reaction time. Under the optimal conditions, the developed immunosensors retained an excellent detection performance of *E. coli* O157:H7 with the linear range of $10^1$-$10^6$ CFU $mL^{-1}$, and the detection sensitivity reached as low as 10 CFU $mL^{-1}$ (FIG. 38). As compared in TABLE 12, the fabricated immunosensors enhancing by CGC hybrid nanoflowers showed better performance for the detection of E. coli O157:H7. The selectivity of the present method was evaluated by using E. coli O157:H7, and Salmonella, Listeria monocytogenes as nontarget bacteria at the same concentration of $1\times10^4$ CFU $mL^{-1}$. E. coli O157:H7 yielded significant pH decreasing, while other nontarget bacteria only produced negligible pH decreasing (not shown). This indicated that the method showed good selectivity. Interestingly, it was observed that the detection of E. coli O157:H7 can also be semiquantified by observing the visible color changes of commercial pH indicator strip. Finally, the reliability and feasibility of the proposed immunoassay method has been successfully proved by the good detection performance of E. coli O157:H7 in real samples (TABLES 13 and 14).

In summary, an innovatively bioinspired method has been developed for the green synthesis of multifunctional all-in-one organic-inorganic hybrid nanoflowers integrating the functions of biorecognition and signal amplification. Employing the as-prepared all-in-one hybrid nanoflowers as signal tags, a simple but potentially powerful amplification biosensing technology with excellent simplicity, portability, sensitivity, and adaptability has been achieved. As expected, this study may increase scientific understanding and technological developments on the bioinspired process for the synthesis of highly innovative all-in-one organic-inorganic hybrid nanostructures, and further establish signal amplification principles for a variety of bioassay applications.

TABLE 12

Comparison of the performance of different methods for detection of E. coli O157:H7.

| Bacterium | Technique | Linear range [CFU per mL] | LOD[a] [CFU per mL] | Reference |
| --- | --- | --- | --- | --- |
| E. coli O157:H7 | Electrochemical impedance spectroscopy | $10^3$-$10^7$ | $10^3$ | Li, et al., Biosens. Bioelectron. 2014, 58, 193 |
| E. coli O157:H7 | Photoluminescent late flow immunoassay | $10^2$-$10^5$ | 10 | Morales-Narvaez et al., Anal. Chem. 2015, 87, 8573 |
| E. coli O157:H7 | Gold nanoparticle based immunoassay | $10^2$-$10^5$ | 148 | Hassan, et al., Biosens. Bioelectron. 2015, 67, 511 |
| E. coli O157:H7 | SERS[b]-based immunoassay | $10^1$-$10^5$; $10^1$-$10^4$; —; — | 4; 8; 70; 10 | Temur, et al., Anal. Bioanal. Chem. 2010, 397, 1595; Guven et al., Analyst 2011, 136, 740; Lin et al., Small 2014, 10, 4700; Cho et al., Biosens. Bioelectron. 2015, 64, 171 |
| E. coli O157:H7 | ELISA | $10^5$-$10^8$ | $10^4$ | Feng, et al., Food Agric. Immunol. 2013, 24, 481 |
| E. coli O157:H7 | ELISA | $10^3$-$10^8$ | $10^3$ | Akanda, et al., Anal. Chem. 2013, 85, 1631 |
| E. coli O157:H7 | ELISA | $10^2$-$10^5$ | $10^2$ | Zhang, et al., Chem. Commun. 2014, 50, 1848 |
| E. coli O157:H7 | ELISA | $10^2$-$10^8$ | 68 | Shen, et al., Gut Pathog. 2014, 6, 14 |
| E. coli O157:H7 | This method | 10-$10^6$ | 10 | This work |

[a]Limit of detection;
[b]Surface-enhanced Raman scattering.

TABLE 13

Recoveries of E. coli O157:H7 - spiked real samples.

| Original value (CFU/mL) | E. coli added (CFU/mL) | E. coli found (CFU/mL) | Recovery (%) |
| --- | --- | --- | --- |
| 0 | $1 \times 10^2$ | $(1.07 \pm 0.072) \times 10^2$ | $107.2 \pm 7.2$ |
| 0 | $1 \times 10^3$ | $(0.961 \pm 0.038) \times 10^3$ | $96.1 \pm 3.8$ |
| 0 | $1 \times 10^4$ | $(1.096 \pm 0.062) \times 10^4$ | $109.6 \pm 6.2$ |
| 0 | $1 \times 10^5$ | $(0.955 \pm 0.081) \times 10^5$ | $95.5 \pm 8.1$ |

TABLE 14

Detection of E. coli O157:H7 in artificially contaminated green tea samples.

| E. coli O157:H7 (CFU/mL) | P/N value from proposed ELISA[a] | Culturing method |
| --- | --- | --- |
| 100 | >3 (+) | + |
| 10 | >3 (+) | + |
| 1 | >3 (+) | + |

"+" symbol means positive result.
[a]the sample was considered positive if the ratio (P/N) of ΔpH value in the test well to that of the negative control well was ≥3.

2. Experimental Section
2.1 Chemicals and Materials

GOx from *Aspergillus niger*, Con A from *Canavalia ensiformis*, Con A FITC conjugate, calcium chloride anhydrous ($CaCl_2$), sodium phosphate monobasic ($NaH_2PO_4$, >99%), sodium phosphate dibasic ($NaH_2PO_4$, >99%), were obtained from Sigma-Aldrich. The E. coli O157:H7, Salmonella and Listeria monocytogenes were kindly provided by School of Food Science in Washington State University. Monoclonal antibody to E. coli O157:H7 was obtained from KPL Company. Sulfo-Cyanine5 N-hydroxysuccinimide (NETS) ester was purchased from Lumiprobe Corporation. All chemical reagents were used as received without further purification. All aqueous solutions were prepared using deionized (DI) water with a resistivity of 18.2 MΩ cm.

2.2 Synthesis and Characterization of Con A-GOx-CaHPO$_4$ Hybrid Nanoflowers

The synthesis of Con A-GOx-CaHPO$_4$ hybrid nanoflowers was carried out in a 1.5 mL eppendorf tube. In a typical synthesis, 0.2769 mg GOx and 0.0231 mg Con A were dissolved in 1 mL buffer solution ($3\times10^{-3}$ M PBS, pH 6.8). Then 20 μL $200\times10^{-3}$ M $CaCl_2$ was added to the buffer solution. The mixture in the tube was left to react at room temperature for 12 h. The products were purified by three repeated steps with centrifuging at 10000 rpm for 5 min and then washing with DI water. For SEM observation, the suspension of the prepared nanoflowers was filtered and dried on a membrane (pore size: 0.1 μm) and sputter coated with gold. For TEM observation, a drop of the suspension of the prepared nanoflowers was added to a carbon grid and dried at room temperature. For fluorescence confocal microscopy imaging, a drop of the suspension of the prepared nanoflowers was added to a glass slide and dried at room temperature before fluorescence observation.

2.3 Synthesis of GOx-Cy5 Conjugate

Labeling of GOx with Sulfo-Cy5 NHS ester was according to the Lumiprobe Corporation recommended protocol. Briefly, 10 mg GOx was dissolved in the 900 μL 0.1 M sodium bicarbonate solution. 0.30 mg Sulfo-Cyanine5 NHS ester was dissolved in 100 μL Dimethylformamide (DMF). Then the Sulfo-Cyanine5 NETS ester solution was added to the glucose oxidase solution and vortexed well. After keeping at 4° C. overnight, GOx-Cy5 conjugate was purified by Nanosep centrifugal devices with 3000 molecular weight cutoff ultrafiltration membranes.

2.4 Encapsulation Efficiency and Distribution of GOx and Con A in Hybrid Nanoflowers To calculate the encapsulation efficiency and ascertain distribution of GOx and Con A in the prepared hybrid nanoflowers, Cy5 labelled GOx and FITC labelled Con A were introduced to replace the GOx and Con A for the synthesis of hybrid nanoflowers. Because the molecular weight of Cy5 and FITC is small and could be negligible compared with GOx and Con A, the encapsulation efficiency of GOx-Cy5 and Con A-FITC could be deemed as the encapsulation efficiency of GOx and Con A, respectively.

To establish the calibration curve for the concentration of GOx, 0, 0.05, 0.1, 0.15, and 0.3 mg mL$^{-1}$ GOx-Cy5 dissolved in PBS solutions (1 mL, 3×10$^{-3}$ M) were prepared. The excitation for Cy5 was 646 nm and the fluorescence intensity of the emission at 670 nm was monitored for the solution with different concentrations. The standard curve was Y=−760.74628+86721.17618×X (R=0.996). To establish the calibration curve for the concentration of Con A, 0, 0.001, 0.01, 0.015, and 0.025 mg mL$^{-1}$ Con A-FITC dissolved in PBS solutions (1 mL, 3×10$^{-3}$ M) were prepared. The excitation for FITC was 488 nm and the fluorescence intensity of the emission at 525 nm was monitored for each solution. The corresponding standard curve was Y=354.41921+214474×X (R=0.999). The amount of non-immobilized GOx was determined in the following manner: The fluorescence intensity of the emission of 10 μL supernatant solution after centrifuged was taken to determine the amount of free GOx based on the calibration curve. The amount of encapsulated GOx could be defined as $E=T_g-F_g$, where $T_g$ and $F_g$ stand for total amount of GOx introduced and free GOx, respectively. Thereafter, the encapsulation efficiency of GOx could be defined as $(T_g-F_g)/T_g$. The encapsulation efficiency of Con A could be measured by the same manner.

2.5 HRP Binding

According to procedure described above, CGC hybrid nanoflowers and GOx-CaHPO$_4$ hybrid nanoflowers were prepared to bind to HRP. For GOx-CaHPO$_4$ hybrid nanoflowers, 0.3 mg GOx was used to prepare the nanoflowers. After adding 100 μL 10 μg mL$^{-1}$ HRP to the prepared two kinds of hybrid nanoflowers for binding 10 min at 37° C., the hybrid nanoflowers were washed with distilled water three times to remove unbonded HRP. Then 10 μL obtained CGC hybrid nanoflowers were added to 300 μL TMB Liquid Substrate System (Sigma).

2.6 Catalytic Studies

The activity of GOx was evaluated using glucose oxidase activity assay kit (Sigma-Aldrich). All procedures were in accordance with the manufacturer's protocol. The concentrations of free GOx and immobilized GOx were both kept at 0.1 μg mL$^{-1}$ for all catalytic studies.

2.7 Optimized Procedure for E. coli O157:H7 Detection—Effect of Amount Ratio Between GOx and Con A in Organic Component The concentration of E. coli O157:H7 used for all the optimized procedures was 10$^4$ CFU mL$^{-1}$. The amount of GOx immobilized on CGC hybrid nanoflowers determined the yield of gluconic acid, thereby determining the change of pH value. The amount of Con A affected the binding efficiency of CGC hybrid nanoflowers for E. coli O157:H7. Hence, organic component added with different amount ratio between GOx and Con A directly influenced the performance of hybrid nanoflower for detecting E. coli O157:H7. It was observed that the total organic component (0.3 mg) with the amount ratio of 12:1 between GOx and Con A resulted in the maximum pH value change and was used as the optimized parameters for further measurements.

2.8 Optimized Procedure for E. coli O157:H7 Detection—Effect of Temperature

The activity of GOx may be affected by reaction temperature. The effect of different temperature ranging from 20 to 40° C. was investigated. The maximum pH value change was obtained at 35° C. and, therefore, 35° C. was chosen as optimized reaction temperature.

2.9 Optimized Procedure for E. coli 0157: H7 Detection—Effect of Reaction Time with Glucose The effect of reaction time with glucose catalyzed by CGC within 2 h was investigated. The glucose could be catalyzed by GOx to produce gluconic acid which causes pH value decrease. With the reaction time increasing, it was observed that the pH value decreased sharply within the first 75 min, then the pH value decreased slightly in the rest of 45 min. To obtain the best results, 90 min was chosen as optimized reaction time.

2.10 Procedure for E. coli O157:H7 Detection Using pH Meter 200 ng mL$^{-1}$ monoclonal antibody to E. coli O157:H7 was added to the 96-well plate, 200 μL for each well. The 96-well plate was placed at 37° C. for 2 h. Then the 96-well plate was washed with phosphate buffered saline with Tween 20 (PBST) for three times. 10 mg mL$^{-1}$ bovine serum albumin (BSA) was used to block nonspecific binding site on the plate, and the plate was incubated at 37° C. for 1 h. After 96-well plate was washed with PBST for three times, 200 μL E. coli O157:H7 with different concentration was added to the 96-well plate incubating at 37° C. for 1 h, then the 96-well plate was washed with PBST for three times. After that, the synthesized CGC was diluted ten times and pipette 100 μL CGC to each well. The plate was incubated at 37° C. for 25 min and then washed with PBST for three times and thereafter DI water (pH 7.0) for three times. 100 μL solution containing 500×10$^{-3}$ M glucose and 10 μg mL$^{-1}$ catalase was added to each well, the reaction was allowed to proceed for 90 min at 35° C. Finally, the pH meter was used to measure the pH value of solution in each well.

2.11 Real Sample Studies

For recovery study, the milk was purchased from a local supermarket without any pretreatment and E. coli O157:H7 was analyzed by standard culture and colony counting method. Then the E. coli O157:H7 was spiked into milk at the concentration of 1×10$^2$, 1×10$^3$, 1×10$^4$, and 1×10$^5$ CFU mL$^{-1}$. Recoveries of E. coli O157:H7 was in the range of 95.5%±8.1%-109.6%±6.2% (TABLE 13). For real positive sample study, the *E. coli* O157:H7 was detected in artificially contaminated green tea samples after 8 h enrichment and procedure performed as previously described with a little modification. (Haes, A. J., et al., J. Am. Chem. Soc. 2005, 127, 2264) Briefly, 2.5 g green tea was added to 22.5 mL hot sterile water (90-100° C.) for 30 min, then the obtained tea solution was filtered. 100 µL tea solution was dissolved in 900 µL PBS for determination. 1 mL tea solution was dissolved in 9 mL EC (*Escherichia coli*) broth for culture at 37° C. for 8 h. The resulting culture medium was centrifuged at 7000 rpm for 5 min. The collected pellet was dissolved in 100 µL PBS for determination. Compared with standard culture of 24-94 h enrichment process, the proposed method was fast and 1 CFU *E. coli* O157:H7 from 2.5 g green tea sample could be detected.

2.12 Instruments

The brand of pH meter used in this work was HORIBA (Model B-713). Transmission electron microscopy images were obtained by Philips CM200 UT (Field Emission Instruments, USA). FEI Sirion field emission scanning electron microscope was used for SEM imaging. XRD characterization was carried out by Rigaku Miniflex 600. Fluorescence spectrum and fluorescence imagine was collected using TECAN XFluor multifunctional microplate reader and fluorescence confocal microscopy (Leica Microsystems Inc., IL, USA), respectively.

Example 7

This Example describes a smart phone-based immunosensor coupled with nanoflower signal amplification for rapid detection of *Salmonella enteritidis* in dairy foods and water.

Abstract: *Salmonella* is a standout amongst the most foodborne pathogens causing harmful disease. To protect consumers from food poisoning due to *Salmonella* infection, it is important to develop a quick, simple, reliable and sensitive method, which can detect *Salmonella* in foods at low concentration in a timely manner. We have effectively established a novel magnetic nano biosensor with high sensitivity for the visual and quantitative detection of *S. enteritidis* from milk, cheese and water. Milk, cheese and water samples inoculated with different concentrations of *S. enteritidis* have been tested using anti *S. enteritidis* streptavidin magnetic beads and biotin labeled antibody as capture platform and coupled with nanocomposite (detecting antibody-HRP enzyme and inorganic nanoflower), where the signal amplification based on HRP enzyme which is enhanced by the action of nanoflower and produce visual color easily detected by the smartphone device in a very low concentration range. The developed assay was able to detect *S. enteritidis* in tap water, milk and cheese, with a detection limit of 1.0 CFU/mL and 1.0 CFU/g, respectively. Recoveries percentages of spiked milk, cheese and tap water samples with $10^2$, $10^3$ and $10^4$ CFU/mL from live *Salmonella* were 98.2, 96.1 and 95.4 (in milk), 94.3, 98.6 and 99.5 (in cheese) and 95.8, 101.2 and 97.8 (in water) using designed device, respectively. The effective application of this innovation in milk and cheese indicates the possibility of its application in various food products.

1. Introduction

*Salmonella* is one of the major foodborne pathogens that cause food poisoning and affects human health, causing fever, abdominal cramps, vomiting, diarrhea and weakness. Humans are usually infected from eating undercooked poultry meat, milk and eggs, fresh produce or foods cross-contaminated with *Salmonella*.

Different techniques have been developed to detect the presence of low levels of *Salmonella* in foods. Conventional methods for *Salmonella* detection involved different steps of pre-enrichment, selective enrichment and selective plating, which is time consuming, tedious and arduous. Other methods such as PCR and ELISA are developed for *Salmonella* detection but these methods require costly hardware and considerable technical expertise to perform and furthermore lack of specificity and sensitivity. The improvement of new systems with quicker reaction time, better affectability and selectivity and no requirement for pre-enrichment remains a test of research intrigue.

Biosensors have demonstrated awesome potential for quick detection of foodborne pathogens. Additionally, nanotechnology shows an extraordinary chance to develop quick, accurate and cost-effective diagnostics for the detection of food borne pathogens. The nanomaterials are characterized by their small size (1-100 nm) and large surface area, resulting in enhanced surface reactivity, improved electrical conductivity and enhanced magnetic properties, among others. Above all, adjustments of the nanostructures' surface can change significantly some of their properties. Numerous nanoparticles have been developed to detect particular molecular targets in biodiagnostic applications, including pathogen detection. Among them, gold nanoparticles, silver nanoparticles, alloy nanoparticles, inorganic nanoflower nanoparticles and magnetic nanoparticles.

Magnetic nanoparticles connected to antibodies have been utilized for the immunomagnetic separation of nucleic acids, proteins, viruses and bacteria. Immunomagnetic separation (IMS) has been used to successfully isolate or enrich of target organisms from complex matrices in food, clinical, and environmental samples. IMS reduces the total assay time and provides higher sensitivity for pathogen detection in complex food or environmental samples. Recently, protein-inorganic hybrid nanoflowers made of protein and $Cu_3(PO_4)_2$ have attracted much consideration since being initially described by Richard Zare and co-workers. The antibody-enzyme-inorganic nanoflower showed incredibly improved catalytic activity and stability.

In recent years, smartphone-based portable and low-cost devices have been used in biosensing and point of care diagnostics. Smartphone, a multifunctional platform with good memory system and high-quality camera lenses, now not only work as a communication tool, but also as a sensing platform for research studying or detection with signal output. It is more accessible and cheaper than other huge laboratory instrument, without limitations among users. Researchers recently approved the possibility of using smartphones in bioanalytical sciences including a smartphone colorimetric reader.

We therefore constructed a smartphone-based immunosensor coupled with nanoflower signal amplification for rapid detection of *Salmonella enteritidis* in dairy foods and water. We first conjugate the streptavidin magnetic beads and biotin labeled antibody then combine them with the prepared enzyme-inorganic nanoflower composite. The combination of the magnetic-antibody and the nanocomposite facilitates the specific capture of the antigen, i.e., pathogenic bacteria, and enhances the enzymatic activity and stability for producing an amplified signal that could be detected and quantified by the developed smartphone-based device. Our data indicated that this approach resulted in a highly sensitive detection method, which is minimally affected by other components in the food.

2. Experimental Section 2.1 Reagents and Materials

*Salmonella enteritidis* PT30 was from American Tissue Culture Collection (ATCC, Manassas, Va.). Mouse monoclonal anti-*Salmonella Enteritidis* antibody was purchased from Abcam (Cambridge, Mass.). Goat polyclonal biotin-labeled anti-*Salmonella* antibody was purchased from KPL Inc. (Gaithersburg, Md.). Streptavidin magnetic beads were purchased from ThermoFisher Scientific Inc. (Eugene, Oreg., USA). Horseradish peroxidase (HRP), dibasic sodium phosphate ($Na_2HPO_4$), monobasic sodium phosphate ($NaH_2PO_4$), calcium chloride anhydrous ($CaCl_2$), 3,3',5,5'-tetramethylbenzidine (TMB) liquid substrate system for ELISA, bovine serum albumin (BSA), phosphate-buffered saline (PBS, 0.01 M phosphate buffer, 0.0027 M potassium chloride and 0.137 M sodium chloride, pH 7.4, at 25° C.), Tween 20 and Greiner 96-well V-bottom plates were purchased from Sigma-Aldrich (St. Louis, Mo., USA).

2.2 Methods 2.2.1 *S. enteritidis* Preparation

*S. enteritidis* PT30 (ATCC BAA-1045) was maintained at −80° C. in Trypticase Soy Broth (Becton, Dickinson and Company, Sparks, Md.) supplied with 0.6% Yeast Extract (Fisher Scientific, Fair Lawn, N.J.) (TSBYE) and 15% (v/v) glycerol. Bacteria were first activated in TSBYE at 37° C. for 8 h statically, 1:1000 transferred to TSBYE, and incubated at 37° C. statically for additional 14 h. The overnight culture was washed once and re-suspend in sterile PBS (pH7.4). The resulting bacterial suspension was serially diluted to appropriate concentrations for live cell experiment. For the dead cell experiment, the bacterial suspension was heat-inactivated in boiling water for 30 min followed by the addition of formalin (J. T. Baker, Phillipsburg, N.J.) to a final concentration of 0.5% (v/v).

2.2.2 Preparation of Magnetic-Antibody and Antibody-Enzyme-Inorganic Nanoflowers To synthesize streptavidin magnetic beads-biotin labeled antibody conjugate, Goat polyclonal biotin-labeled anti-*Salmonella* antibody (1 μg/mL) was added to streptavidin magnetic beads (50 μg/ml) at a ratio of 1:1, mixed thoroughly and then incubated at room temperature for 2 h in a shaker incubator (Barnstead/Lab-Line Instrument, USA).

To synthesize antibody-enzyme-inorganic nanoflowers, 15 μL of 200 mM $NaH_2PO_4$, 15 μL 200 mM $Na_2HPO_4$, 29.5 μL HRP (10 mg/ml), 5 μL of monoclonal anti-*S. enteritidis* antibody were added to 920 μL distill water. Then, 20 μL of 200 mM $CaCl_2$ was added to the solution, which was mixed and incubated at room temperature for 12 h. The products (synthesized nanoflowers) were obtained by centrifugation at 10000 rpm for 5 min and washing twice with distilled water.

The synthesized nanoflowers were dried on a filter membrane (pore size: 0.1 μm) and then sputter coated with gold for SEM observation. For TEM observation, the synthesized nanoflowers were dried on a carbon grid at room temperature.

2.2.3 Sandwich Magnetic-Antibody and Three-in-One Nanoflower-Based ELISA of *S. enteritidis*

On a 96 well plate that is fitted firmly over a 96 well plate magnetic separator, add 50 μL of conjugated streptavidin magnetic beads and biotin labeled anti-*Salmonella* antibody followed by addition of 200 μL of PBSA (1% BSA in 0.01 M PBS) and incubated at 37° C. for 1.5 h. The corresponding wells of plate on its 96 well plate magnetic separator were aspirated and washed with 300 μL of PB ST (0.05% Tween 20 in 0.01 M PBS) four to five times to remove unbounded antibodies. Then 50 μL of *S. enteritidis* PT30 diluted in PBS at different concentrations was added to each well and incubated at 37° C. for 1 h, then followed by washing four to five times. Afterwards, 50 μL of antibody-enzyme-inorganic nanoflowers diluted five times was added to each well and incubated at 37° C. for 40 min. The plate was washed five times with PBST to remove unbound HRP-$Ab_2$-inorganic nanoflower. Finally, 50 μL of TMB liquid substrate system for ELISA was added to each well and incubated at 37° C. for 15 min. The magnetic-antibody and the antibody-enzyme-inorganic nanoflower based ELISA immunoassay steps for *S. enteritidis* detection are delineated in FIG. 39.

2.2.4 Detection Using a Smartphone Microplate Reader

The signal was read by using a home-built smartphone microplate reader. In this smartphone microplate reader, uniform illumination light from a backlight panel was used as the light source. Compared to a conventional laboratory microplate reader, which uses a scanning mechanism to read signals from well to well, the smartphone reader uses an area image detector (i.e., a CMOS sensor) to capture light signals from a whole microplate. Thus, to increase the accuracy, all stray light between microplate wells needs to be blocked. Two aperture arrays (one beneath the microplate and the other above the microplate) were used. Due to the aperture arrays and the limitation of the viewing angle of the smartphone camera, most of the wells are blocked in the captured image. A prism array was used to deviate the light ray path from each well. The details of the design and fabrication of the smartphone microplate reader can be found in our previous work (see Wang, L. J., et al., 2016. Anal. Chem. 88, 8302-8308, incorporated herein by reference in its entirety). An App was used to control the image capture parameters (ISO 350, exposure time of 0.035 s, redGain: 4, greenGain: 1.75536 and blueGain: 1.39785). To analyze the results, the RGB value of each well was obtained by using the software ImageJ and absorbance values were then calculated. To compare the results, a Tecan Safire 2 microplate reader (Tecan, Switzerland) set to 450 nm with a wavelength of 650 nm (OD results) was also used.

2.2.5 Preparation of Milk, Cheese and Water Samples

Fat free milk and soft cheese samples were purchased from a local retail market and analyzed by a standard culturing method (International Organization for Standardization, 2007) for the presence of *S. enteritidis*, and only negative samples were selected to be spiked by bacteria. 10 mL of *S. enteritidis* free milk and water samples were added to 90 mL of sterile PBS and from which we prepared different bacterial concentrations. 10 g of *S. enteritidis* free cheese samples were homogenized with 90 mL of 2% sterile sodium citrate solution in a stomacher 400 circulator (Seward, UK) for 3 min until the product was thoroughly dispersed to prepare $10^{-1}$ dilution, then used as a diluent to prepare different bacterial concentrations. Then, the magnetic-antibody with the nanoflower composite was conducted as previously described to calculate the detectable amount of *S. enteritidis*.

2.2.6 Spike and Recovery Protocol

Spike and recovery experiment is an important method for validating and assessing the accuracy of an analytical technique for particular sample types. This experiment was performed by spiking of above prepared milk, cheese and tap water with $10^2$, $10^3$ and $10^4$ CFU/mL heat killed or live *S. enteritidis*, then the spiked samples were evaluated under the same above-mentioned condition. After that, the recovery % of bacteria from milk, cheese and tap water samples was obtained according to the calibration curve results.

3. Results and Discussion

3.1 Characterization of Nanoflowers

Figure 40A:
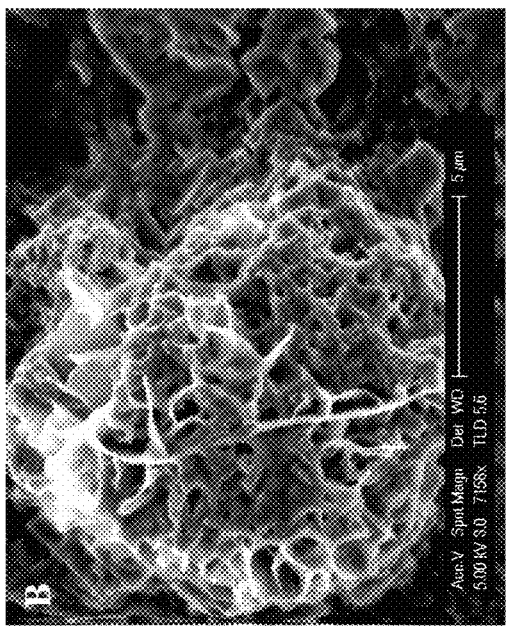
FIGS. 40A-40D are electronic microscopic images for anti *S. enteritidis* antibody HRP Cu$_3$(PO$_4$)$_2$ three-in-one nanoflowers, showing the morphologies of with magnifications by SEM (FIGS. 40A and 40B) and TEM images (FIGS. 40C and 40D).
Figure 40B:
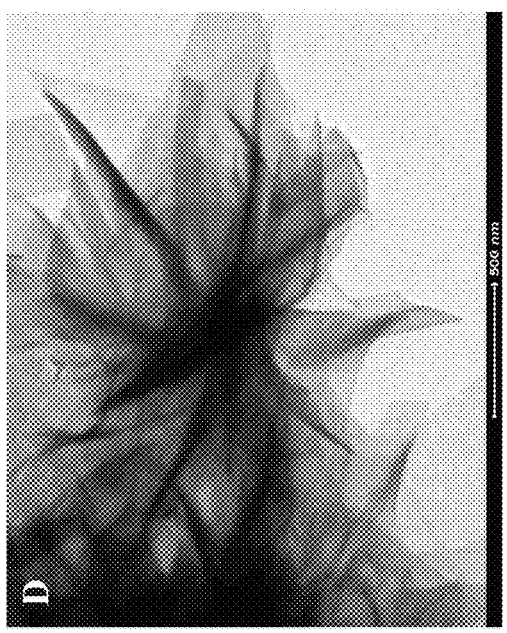
Figure 40C:
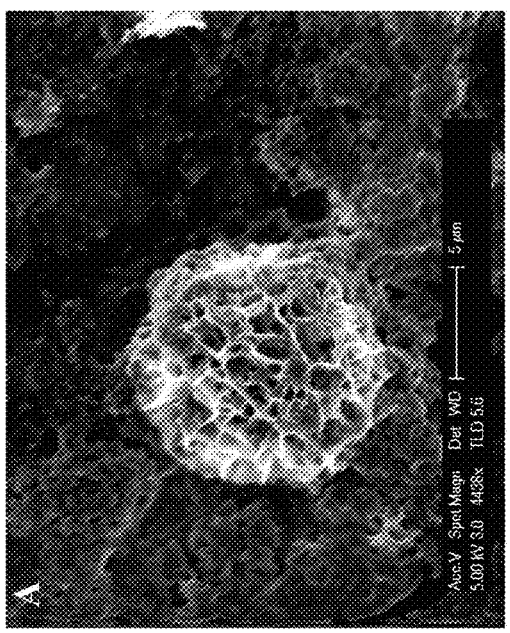
Figure 40D:

Scanning electron microscope (SEM) and transmission electron microscope (TEM) images were obtained to demonstrate the morphology of the nanoflowers (FIGS. 40A-40D). The SEM picture with a magnification power from low to high demonstrated flower-like nanostructure having hierarchical structures with high surface-to-volume ratios with a size around 5 µm (FIGS. 40A and 40B). TEM observation showed nanosheet structures in the petal-like sections (FIGS. 40C and 40D).

Figure 41A:
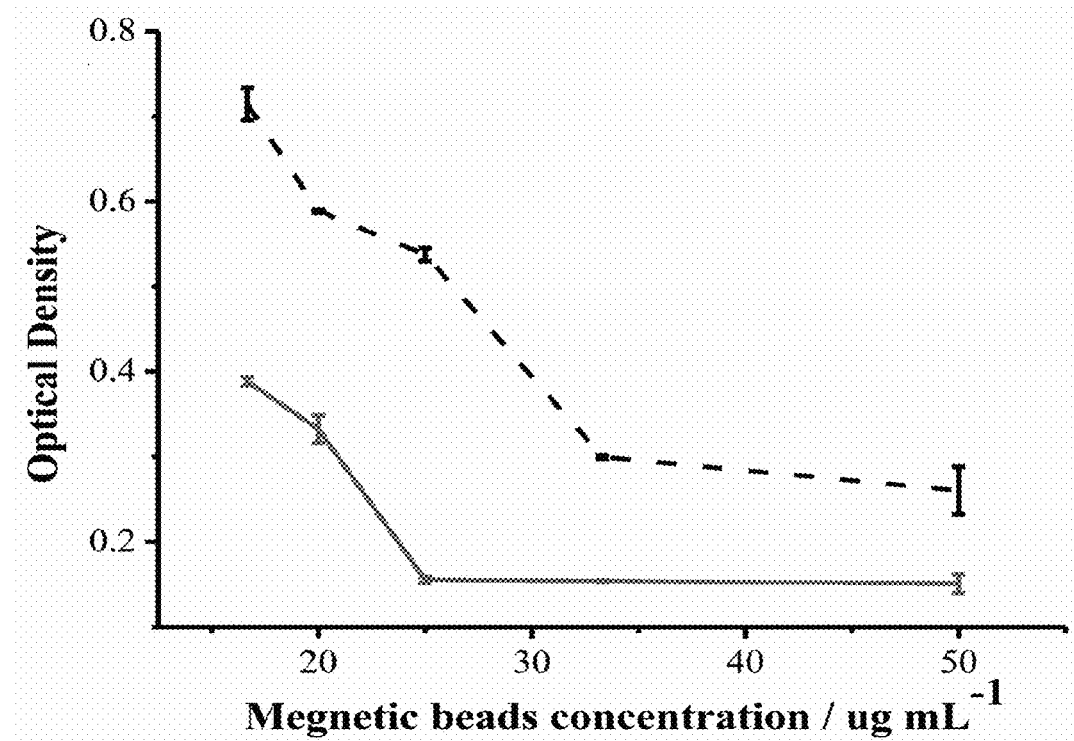
FIGS. 41A-41D graphically illustrate the optimization of ELISA detection conditions.
Figure 41B:
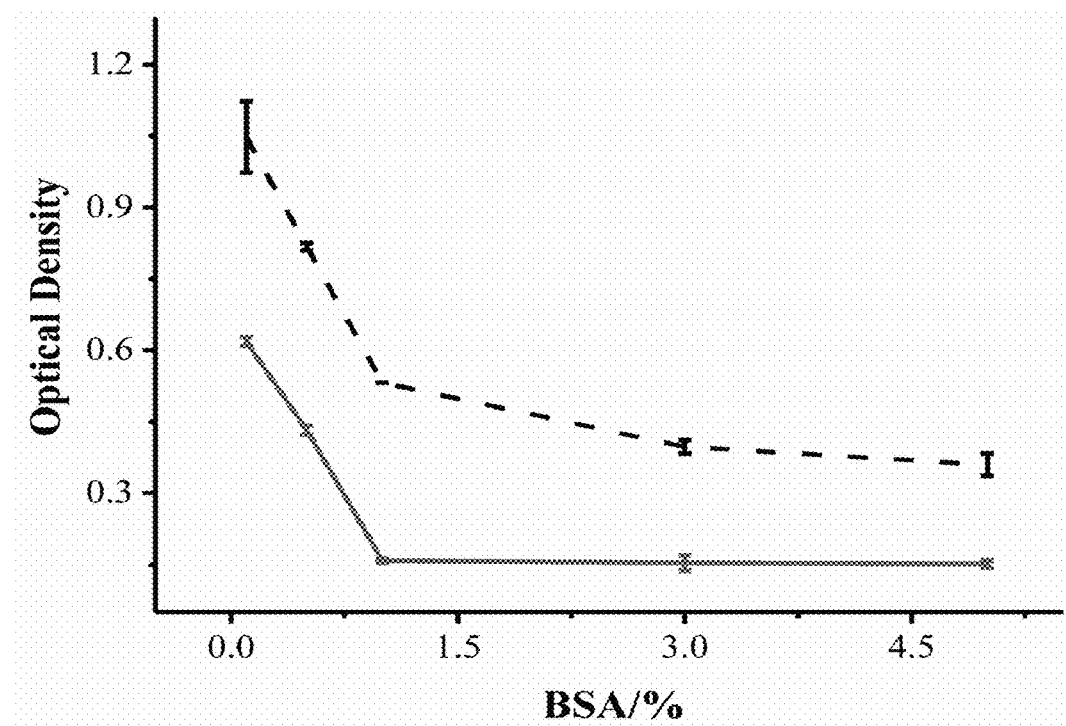
Figure 41C:
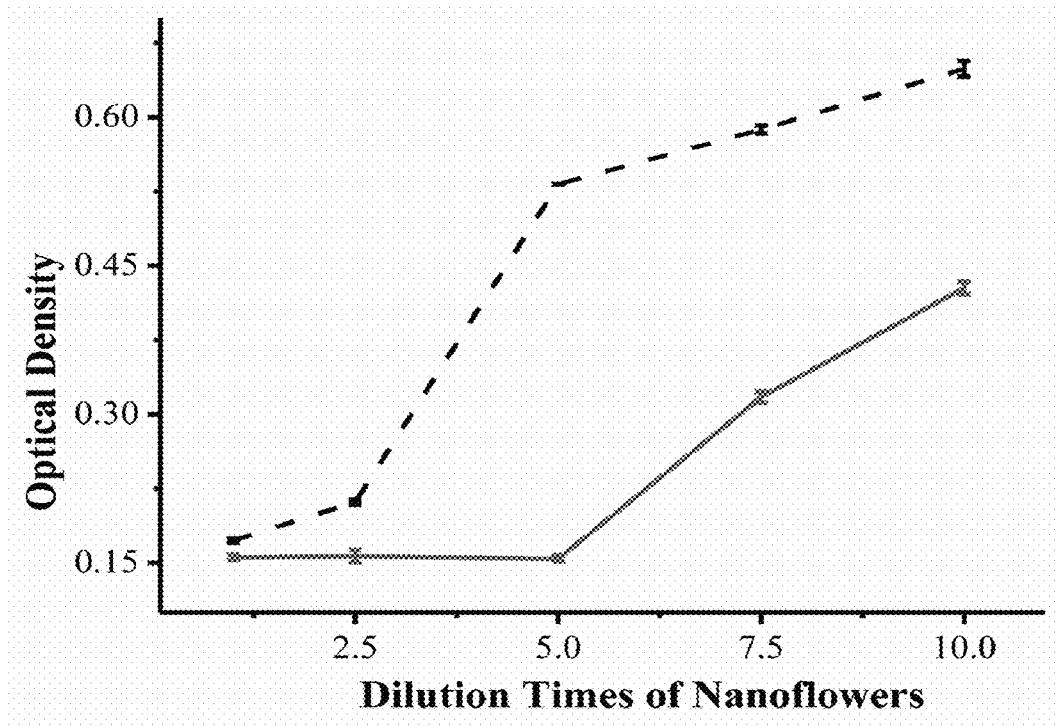
Figure 41D:
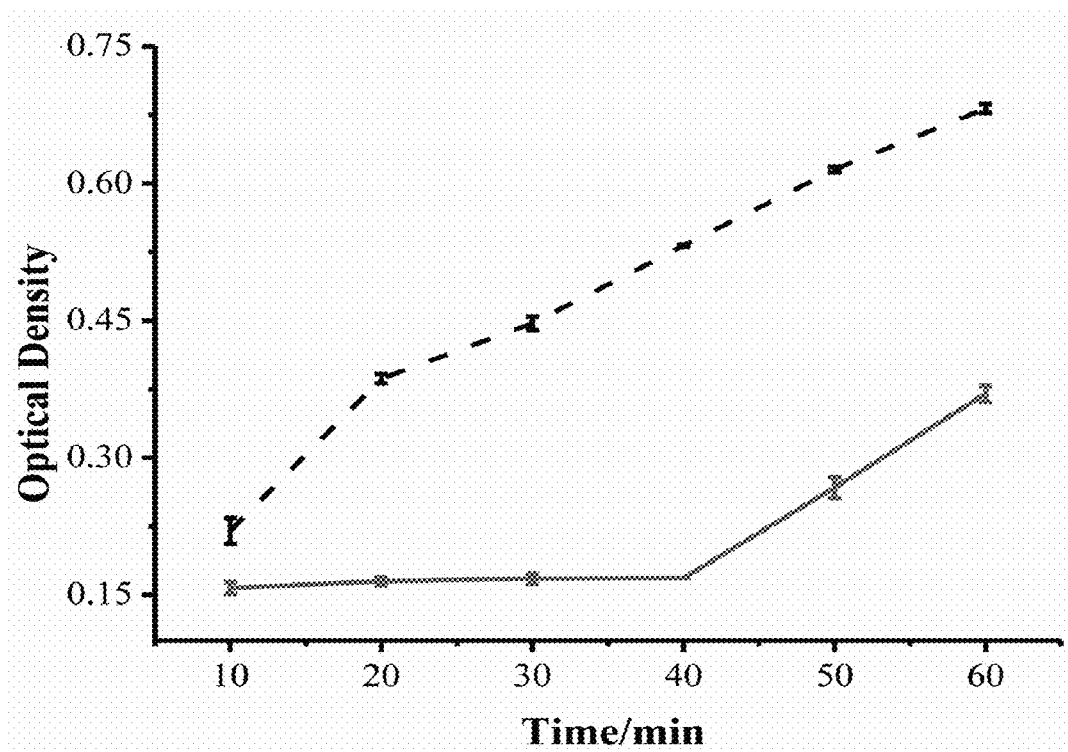

3.2 Optimization of Detection Conditions for the Developed Sandwich-Based ELISA Different factors can influence ELISA performance. Herein, the optical densities of the control group (0 CFU/mL *S. enteritidis*) and experimental group ($1 \times 10^3$ CFU/mL *S. enteritidis*) were examined at the same time for assessing the impacts of four components on detection sensitivity: the concentration of streptavidin magnetic beads, the concentration of blocking agent-BSA, the dilution factor of the nanoflowers (HRP-$Ab_2$-$Cu_3(PO_4)_2$ nanoflowers), and the incubation time of detection antibody. As presented in FIG. 41A, the OD value of the tested group goes down with increasing the concentration of magnetic beads and tended to level off after 33.3 µg/mL, and the OD of the control group showed false-positive results before 25 µg/mL magnetic beads concentration. Therefore, 25 µg/mL magnetic beads were selected as the appropriate concentration. The concentration of blocking agent-BSA is also an essential parameter for ELISA performance. FIG. 41B shows that the OD value of the tested group goes down with increasing concentration of BSA and tended to level off after 1% BSA, and the OD value of control group showed false-positive results before 1% BSA, which is probably attributed to the fact that insufficient blocking agent might result in nonspecific interaction of the detection antibody. Therefore, 1% BSA was chosen as the proper concentration of blocking agent. FIG. 41C indicated that the dilution factor of detection antibody is another essential parameter. The OD value of the tested group increased with increasing the dilution times of nanoflowers, while the OD value of the control group began to give false-positive results after 5 times dilution of nanoflowers or more. Therefore, 5 times dilution of detection antibody was selected as a proper dilution factor. Additionally, ELISA performance could be affected by the incubation time of detection antibody. As showed in FIG. 41D, the OD value of the control group gave false positive results following 40 min incubation time of HRP-$Ab_2$-$Cu_3(PO_4)_2$ nanoflowers. This is because the longer the incubation time of the antibody, the higher nonspecific binding.

Therefore, 40 minutes of incubation time of detection antibody was selected as the ideal incubation time.

3.3 Colorimetric Detection of *S. enteritidis*

Figure 39:
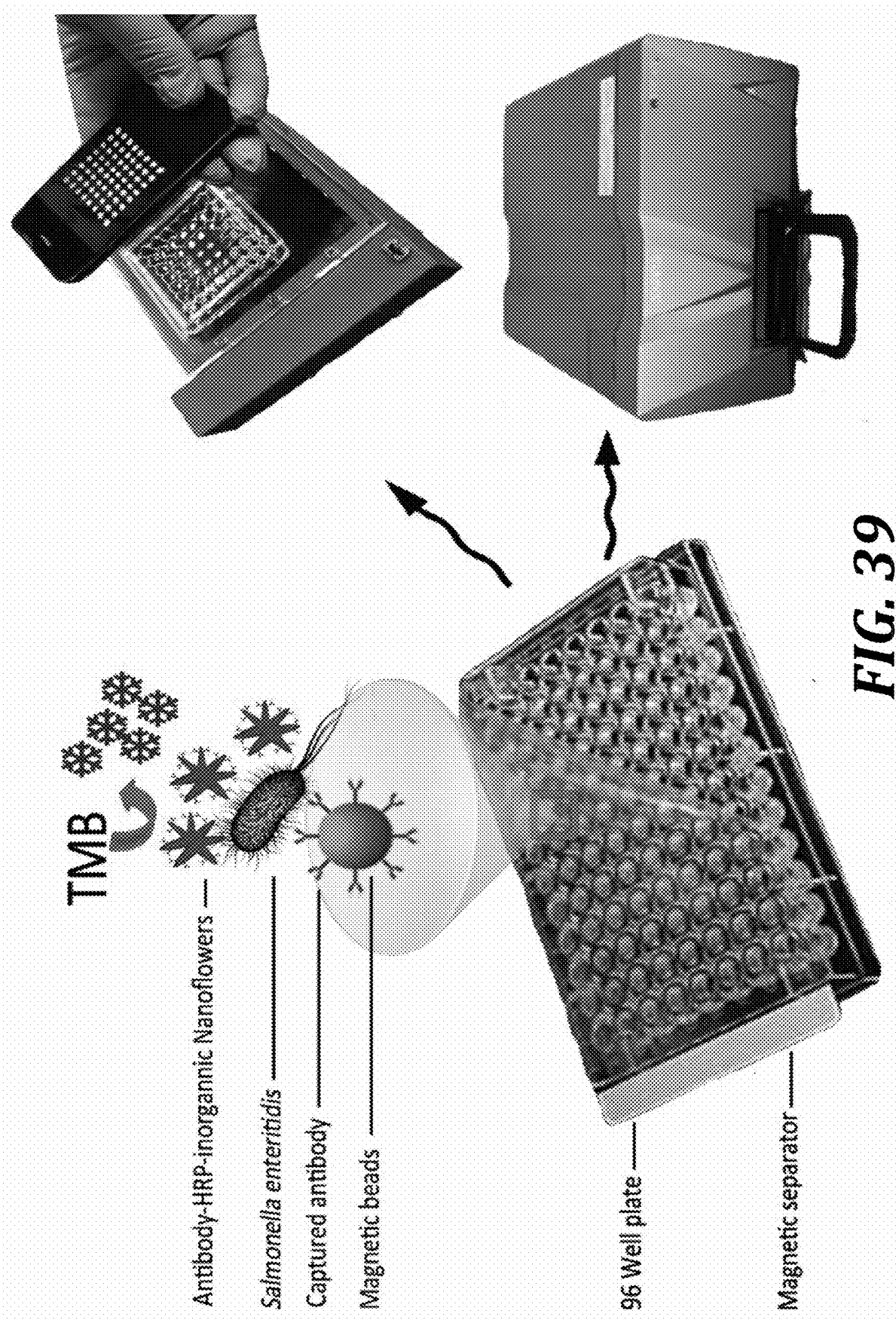
FIG. 39 schematically illustrates an exemplary assay system that is based on conjugation of magnetic beads antibody and enzyme-antibody-inorganic nanoflowers for ultrasensitive detection of *Salmonella enteritidis*.
Figure 42A:
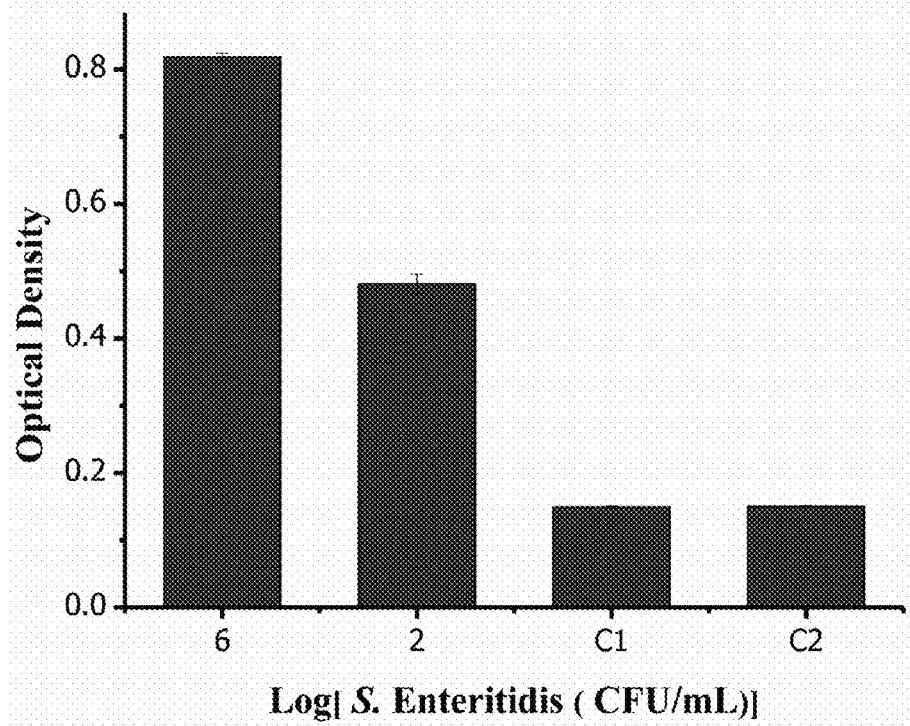
FIGS. 42A and 42B graphically illustrate a test of two different concentrations of *S. enteritidis* ($10^6$ CFU/mL, $10^2$ CFU/mL), C1 (control without nanoflower) and C2 (control without *S. enteritidis*) using the reader (FIG. 42A) and the smart phone (FIG. 42B). Each experiment was repeated three times to obtain the average data value.
Figure 42B:
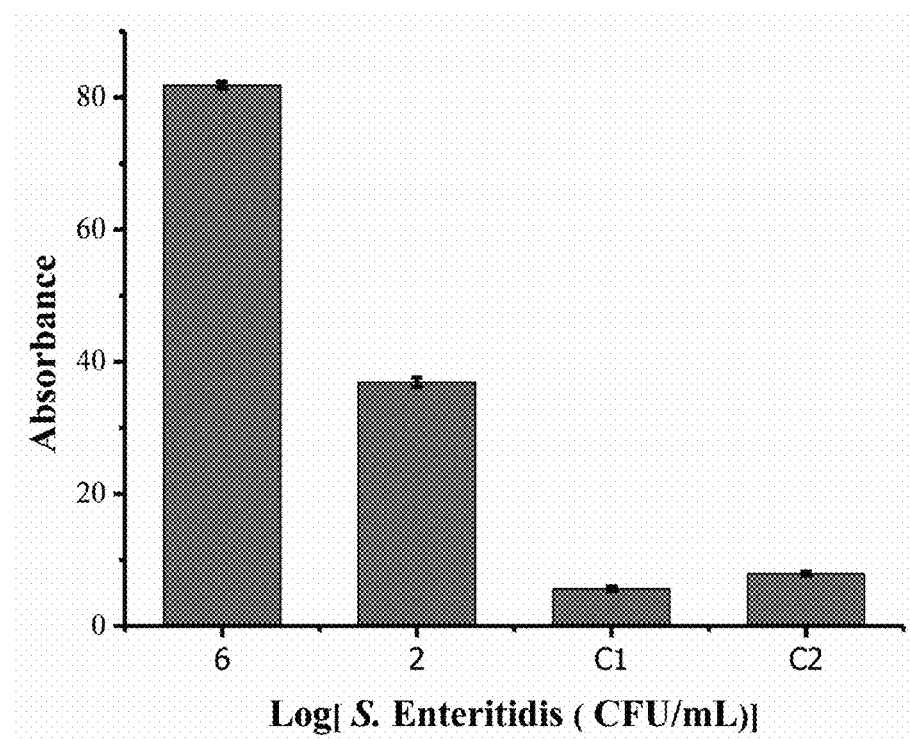
Figure 43A:
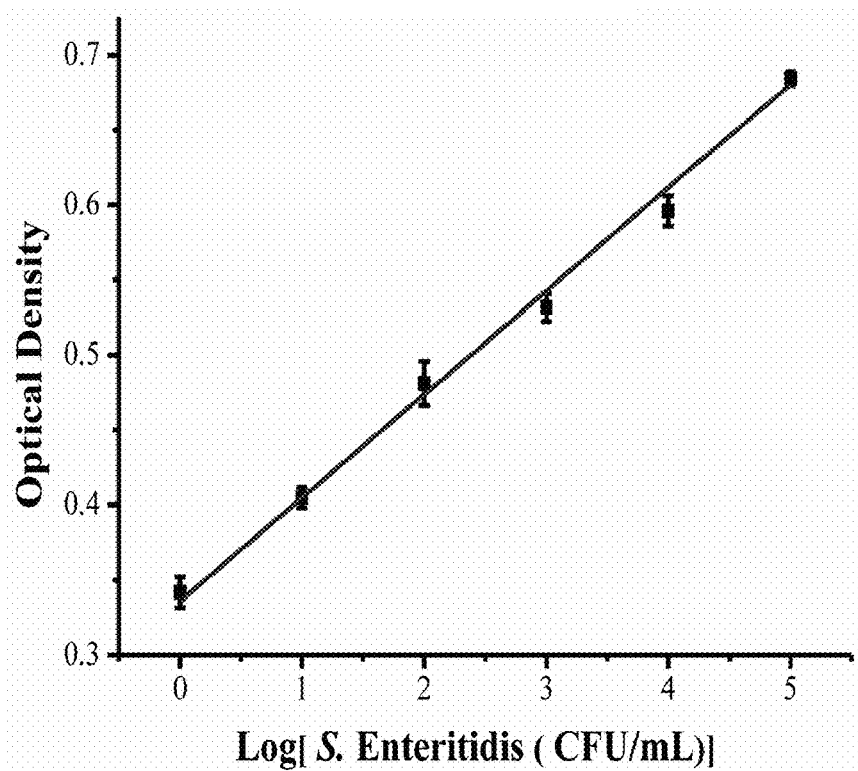
FIGS. 43A and 43B graphically illustrate calibration curves for heat killed *S. enteritidis* detection using the reader (FIG. 43A) and the smart phone (FIG. 43B). Each experiment was repeated three times to obtain the average data value.
Figure 43B:
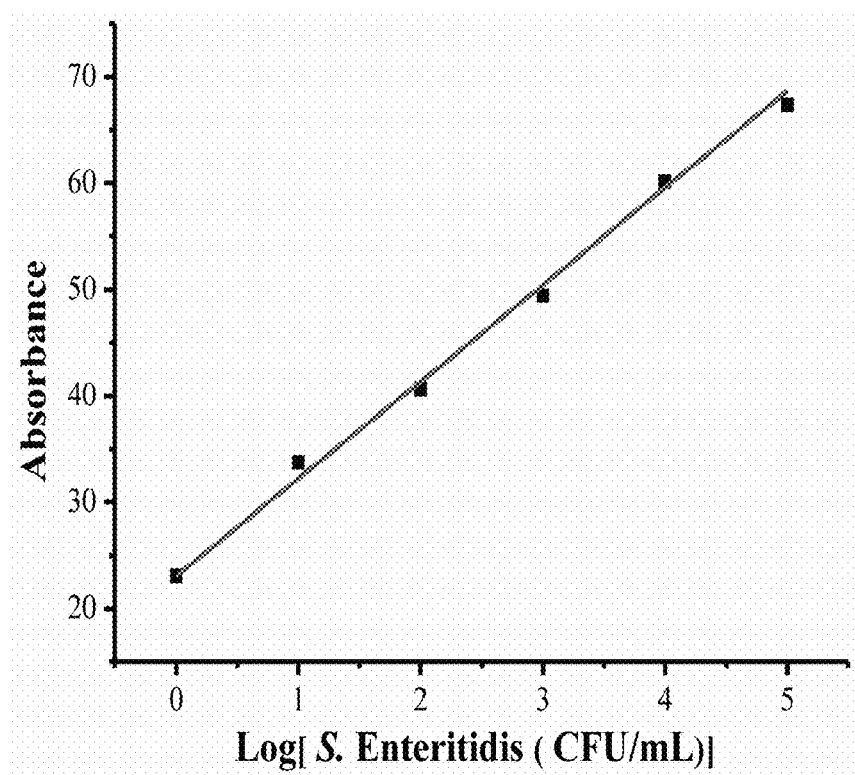
Figure 44A:
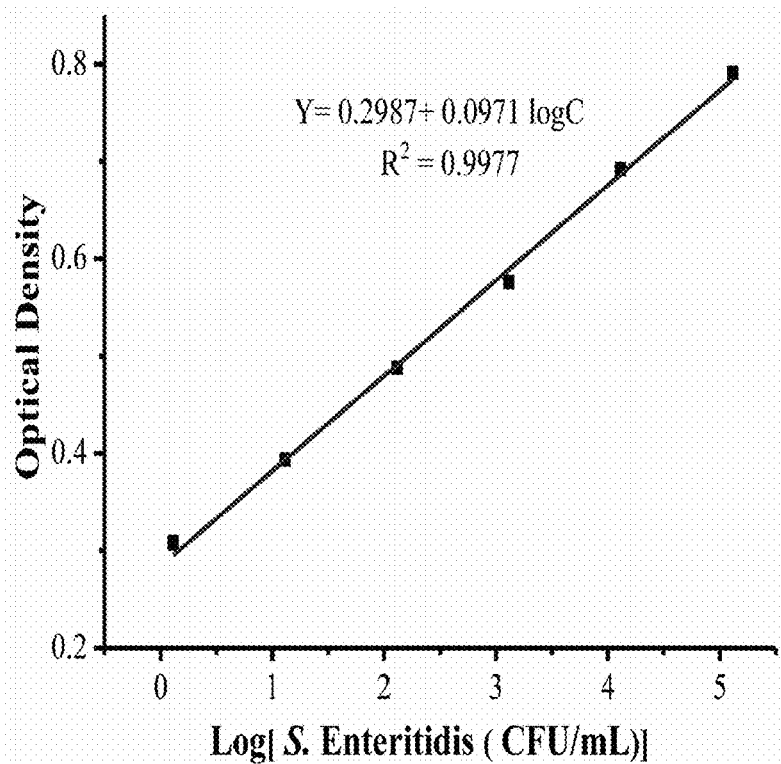
FIGS. 44A and 44B graphically illustrate linear calibration curves for viable *S. enteritidis* detection using the reader (FIG. 44A) and the smart phone (FIG. 44B). Each experiment was repeated three times to obtain the average data value.
Figure 44B:
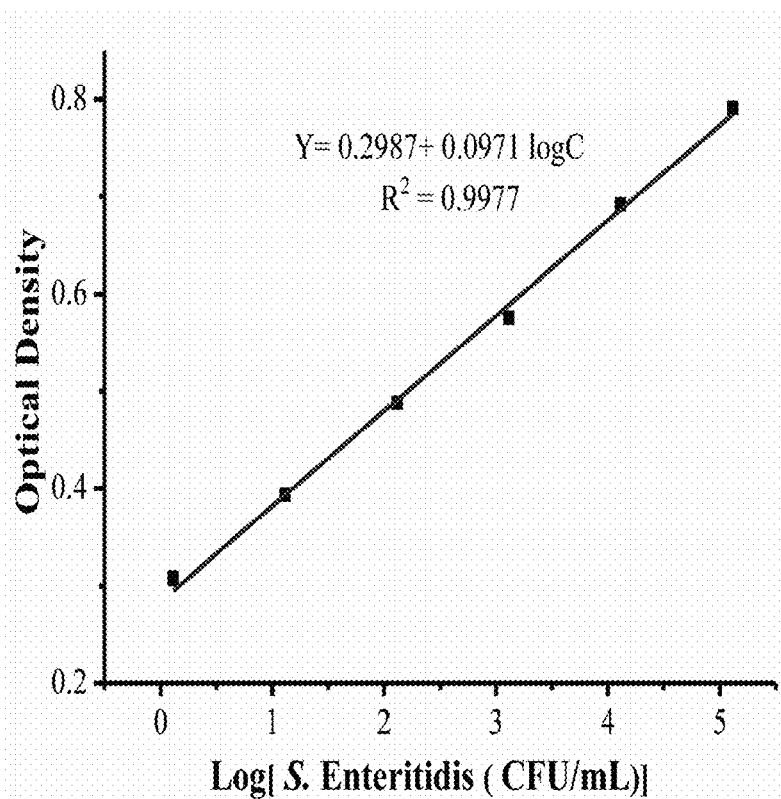

Using the above optimized conditions, the novel magnetic-antibody and the three in one nanocomposite based ELISA system was used to quantitatively determine the concentrations of *S. enteritidis* PT30 as illustrated in FIG. 39. The color intensity increased with increasing the concentration of *S. enteritidis*, while no color observed in any of the controls either in the control without nanoflowers (C1) or a control without *S. enteritidis* (C2) (not shown). Additionally, both OD value from a microplate reader (FIG. 42A) and absorbance value from the smart phone device (FIG. 42D) are increased with increasing the concentration of *S. enteritidis*, with a similar ratio. The calibration curve between the OD value and the concentration of heat killed *S. enteritidis* (FIG. 43A) as well as between the absorbance and the concentration of heat killed *S. enteritidis* (FIG. 43B) showed a linear regression; the OD and the absorbance increment were highly sensitive to the concentration of *S. enteritidis*. Similar results were obtained for live *Salmonella* cells (FIGS. 44A and 44B). These data collectively demonstrated that our new magnetic-antibody and the three in one nanocomposite based ELISA could provide a quantitative measurement of *S. enteritidis* from 1 to $10^6$ CFU/mL with a detection limit of 1 CFU/mL. Data obtained from a Smartphone device used in this study are parallel with that from microplate reader with similar sensitivity and linearity (FIGS. 43A-44B), indicated that the smart phone is considered a novel new device that could be used for rapid, sensitive and infield detection of *S. enteritidis*. Our presented results are more sensitive than most of reported methods for quantitative determination of *S. enteritidis* (TABLE 15).

TABLE 15

Comparison of the performance of different detection methods for *Salmonella*.

| Bacterium | Technique | LOD* (CFU mL$^{-1}$) | Reference |
|---|---|---|---|
| *S. Enteritidis* | Immunomagnetic separation-bacteriophage | <$10^4$ | Favrin, S. J., et al., 2003. Int. J. Food Microbiol. 85, 63-71 |
| *Salmonella* | Immunosensor based quartz crystal microbalance | $10^4$ | Wong, Y. Y., et al., 2002. Biosens. Bioelectron. 17, 676-684 |
| *S. Enteritidis* | Immunochemical using surface plasmon resonance biosensor | $1.7 \times 10^3$ | Bokken, G. C., et al., 2003. FEMS Microbiol Lett. 22, 75-82. |
| *Salmonella* | Surface plasmon resonance immunosensor | $10^2$ | Oh, B. K., et al., 2004. Biosens. Bioelectron. 19, 1497-1504 |
| *Salmonella* | FRET-based optical fiber biosensor | $10^5$ | Ko, S., Grant, S. A., 2006. Biosens. Bioelectron. 21, 1283-1290 |
| *S. Enteritidis* | Surface plasmon resonance biosensor | 23 | Waswa, J. W., et al., 2006. J. Food Process Engin. 29, 373-385 |
| *Salmonella* | phage-based magnetoelastic biosensors | $5 \times 10^2$ | Li, S., et al., 2010. Biosens. Bioelectron. 26, 1313-1319 |
| *Salmonella* | Electrochemical biosensor | 3 | Ma, X., et al., 2014. J. Microbiol. Methods. 98, 94-98. |

TABLE 15-continued

Comparison of the performance of different detection methods for *Salmonella*.

| Bacterium | Technique | LOD* (CFU mL$^{-1}$) | Reference |
|---|---|---|---|
| *Salmonella* | A microfluidic nano-biosensor | $10^3$ | Kim, G., et al., 2015. Biosens. Bioelectron. 67, 243-247 |
| *S. Enteritidis* | Magnetic-nanocomposite based ELISA | 1 | This work |

*LOD = Limit of detection

Additionally, our results indicated the new developed magnetic-antibody and the antibody-protein-inorganic nanoflower is more sensitive compared to the common protein-conjugated antibody method.

The reproducibility of the developed magnetic nanobiosensor was evaluated by inter-assay coefficients of variation (CVs) and it was shown acceptable reproducibility and precision of the proposed magnetic nanobiosensor. The nanocomposite (antibody-protein-inorganic nanoflowers) could be stored at 4° C. for up to two weeks with an acceptable stability. Over 70% and 50% of the initial response remained after one week and two weeks, respectively.

Recovery experiments were performed using artificially spiked food samples to determine whether assays are interfered by food matrix. Different concentrations of *S. enteritidis* (dead or live cells) were spiked into milk, cheese or tap water, mixed and analyzed for recovery. TABLE 16 shows that the recovery percentages of the heat killed *S. enteritidis* from analyzed samples were in the range from 90.4 to 101.3 for the reader and 94.2 to 101.2 for the smart phone. The recoveries of live *S. enteritidis* from the spiked samples were ranged from 91.2 to 102.1 for the reader and 94.3 to 101.2 for the smartphone (TABLE 17). These high recovery rates demonstrate that this technology is a promising detection method for determination of *S. enteritidis* in food samples.

TABLE 16

Recoveries of heat killed *Salmonella enteritidis* in spiked samples by the developed methods.

| | Original | Spiked | Measured concentration (CFU/mL) | | Recovery (%) | |
|---|---|---|---|---|---|---|
| Samples | Value (CFU/mL) | Concentration (CFU/mL) | Reader | Smart phone | Reader | Smart phone |
| Milk | 0 | $10^2$ | $1.013 \times 1.10^2$ | $0.984 \times 10^2$ | 101.3 | 98.4 |
| Milk | 0 | $10^3$ | $0.959 \times 10^3$ | $0.964 \times 10^3$ | 95.9 | 96.4 |
| Milk | 0 | $10^4$ | $0.963 \times 10^4$ | $0.942 \times 10^4$ | 96.3 | 94.2 |
| Cheese | 0 | $10^2$ | $0.966 \times 10^2$ | $0.973 \times 10^2$ | 96.6 | 97.3 |
| Cheese | 0 | $10^3$ | $0.995 \times 10^3$ | $0.996 \times 10^3$ | 99.5 | 99.6 |
| Cheese | 0 | $10^4$ | $0.904 \times 10^4$ | $0.956 \times 10^4$ | 90.4 | 95.6 |
| Water | 0 | $10^2$ | $1.011 \times 10^2$ | $0.977 \times 10^2$ | 101.1 | 97.7 |
| Water | 0 | $10^3$ | $0.986 \times 10^3$ | $1.012 \times 10^3$ | 98.6 | 101.2 |
| Water | 0 | $10^4$ | $0.958 \times 10^4$ | $0.963 \times 10^4$ | 95.8 | 96.3 |

TABLE 17

Recoveries of live *Salmonella enteritidis* cells in spiked samples by the developed methods.

| | Original | Spiked | Measured concentration (CFU/mL) | | Recovery (%) | |
|---|---|---|---|---|---|---|
| Samples | Value (CFU/mL) | Concentration (CFU/mL) | Reader | Smart phone | Reader | Smart phone |
| Milk | 0 | $1.3 \times 10^2$ | $0.974 \times 10^2$ | $0.982 \times 10^2$ | 97.4 | 98.2 |
| Milk | 0 | $1.3 \times 10^3$ | $0.986 \times 10^3$ | $0.961 \times 10^3$ | 98.6 | 96.1 |
| Milk | 0 | $1.3 \times 10^4$ | $0.977 \times 10^4$ | $0.954 \times 10^4$ | 97.7 | 95.4 |
| Cheese | 0 | $1.3 \times 10^2$ | $1.021 \times 10^2$ | $0.943 \times 10^2$ | 102.1 | 94.3 |
| Cheese | 0 | $1.3 \times 10^3$ | $0.912 \times 10^3$ | $0.986 \times 10^3$ | 91.2 | 98.6 |
| Cheese | 0 | $1.3 \times 10^4$ | $0.960 \times 10^4$ | $0.995 \times 10^4$ | 96.0 | 99.5 |
| Water | 0 | $1.3 \times 10^2$ | $0.933 \times 10^2$ | $0.958 \times 10^2$ | 93.3 | 95.8 |
| Water | 0 | $1.3 \times 10^3$ | $0.931 \times 10^3$ | $1.012 \times 10^3$ | 93.1 | 101.2 |
| Water | 0 | $1.3 \times 10^4$ | $0.929 \times 10^4$ | $0.978 \times 10^4$ | 92.9 | 97.8 |

4. Conclusion

The combination of the magnetic-antibody and the HRP-antibody-inorganic nanoflower based ELISA realized the highly sensitive detection of *S. enteritidis* in food and water sample without enrichment. In addition, smart phone device gives similar accuracy and sensitivity compared to the normal microplate reader, providing convenient and promising tool to detect foodborne pathogens onsite without using expensive microplate reader.

While illustrative embodiments have been illustrated and described, it will be appreciated that various changes can be made therein without departing from the spirit and scope of the invention.

The embodiments of the invention in which an exclusive property or privilege is claimed are defined as follows:

1. An antigen detection reagent, comprising an antigen-binding molecule and a reporter component conjugated to an inorganic nanoflower component,
    wherein:
    the inorganic nanoflower component comprises $Cu_3(PO_4)_2$, $Mn_3(PO_4)_2$, or $CaHPO_4$;
    the reporter component is a reporter enzyme; and
    the reporter component is configured to cooperate with the antigen-binding molecule to provide an amplified signal.

2. The antigen detection reagent of claim 1, wherein the reporter enzyme is horseradish peroxidase (HRP), invertase, glucose oxidase (GOx), or alkaline phosphatase (AP).

\* \* \* \* \*